United States Patent
Inazawa et al.

(10) Patent No.: US 10,876,115 B2
(45) Date of Patent: Dec. 29, 2020

(54) METHOD FOR ASSAYING MICRORNA, CANCER THERAPEUTIC AGENT, AND MEDICAL COMPOSITION CONTAINING SAME FOR CANCER THERAPY

(71) Applicant: National University Corporation Tokyo Medical and Dental University, Tokyo (JP)

(72) Inventors: Johji Inazawa, Tokyo (JP); Jun Inoue, Tokyo (JP); Shinsuke Yamamoto, Tokyo (JP); Tatsuyuki Kawano, Tokyo (JP); Ken-ichi Kozaki, Tokyo (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 0 days.

(21) Appl. No.: 16/241,269

(22) Filed: Jan. 7, 2019

(65) Prior Publication Data

US 2019/0367915 A1    Dec. 5, 2019

Related U.S. Application Data

(60) Continuation of application No. 15/976,460, filed on May 10, 2018, now abandoned, which is a division of application No. 14/767,372, filed as application No. PCT/JP2014/053594 on Feb. 17, 2014, now Pat. No. 9,994,843.

(30) Foreign Application Priority Data

Feb. 15, 2013 (JP) .................. 2013-027399

(51) Int. Cl.
| | |
|---|---|
| C12N 15/113 | (2010.01) |
| A61K 31/713 | (2006.01) |
| G01N 33/50 | (2006.01) |
| A61K 33/24 | (2019.01) |
| A61K 45/06 | (2006.01) |
| A61K 33/243 | (2019.01) |
| A61K 48/00 | (2006.01) |
| A61K 31/7088 | (2006.01) |

(52) U.S. Cl.
CPC ........ *C12N 15/113* (2013.01); *A61K 31/7088* (2013.01); *A61K 31/713* (2013.01); *A61K 33/24* (2013.01); *A61K 33/243* (2019.01); *A61K 45/06* (2013.01); *A61K 48/00* (2013.01); *G01N 33/5011* (2013.01); *C12N 2310/14* (2013.01); *C12N 2310/141* (2013.01); *C12N 2320/30* (2013.01); *C12N 2320/31* (2013.01)

(58) Field of Classification Search
None
See application file for complete search history.

(56) References Cited

U.S. PATENT DOCUMENTS

| | | |
|---|---|---|
| 2006/0167066 A1 | 7/2006 | Cohen et al. |
| 2009/0238896 A1 | 9/2009 | Hernando |
| 2010/0305188 A1 | 12/2010 | Nakano et al. |
| 2011/0130341 A1 | 6/2011 | Suzuki et al. |
| 2012/0269883 A1 | 10/2012 | Gunaratne |
| 2015/0216892 A1 | 8/2015 | Thibonnier |
| 2016/0362689 A1* | 12/2016 | Shi .................. C12N 15/113 |

FOREIGN PATENT DOCUMENTS

| | | |
|---|---|---|
| EP | 2 088 208 A1 | 8/2009 |
| EP | 2 208 499 A1 | 7/2010 |
| JP | 2008-519606 A | 6/2008 |
| JP | 2012-184230 A | 9/2012 |
| JP | 2013-28575 A | 2/2013 |
| WO | 2006/137941 A2 | 12/2006 |
| WO | 2009/036332 A1 | 3/2009 |
| WO | 2009/044899 A1 | 4/2009 |
| WO | 2009/136501 A1 | 11/2009 |
| WO | 2011/111715 A1 | 9/2011 |
| WO | 2011/125245 A1 | 10/2011 |

(Continued)

OTHER PUBLICATIONS

Abstract Supplement, Diseases of the Esophagus, 2010, vol. 23, Supplement, pp. 35A and 1A; http://onlinelibrary.wiley.com/doi/10.1111/j.1442-2050.2010.01101.x/abstract (Sep. 9, 2010).

Boulikas, et al., "Recent clinical trials using cisplatin, carboplatin and their combination chemotherapy drugs (Review)", Oncology Reports, Mar. 1, 2004, vol. 11, No. 3, pp. 559-595 (37 pages).

Chou, et al., "Quantitative analysis of dose-effect relationships: the combined effects of multiple drugs or enzyme inhibitors", Advances in Enzyme Regulation, Pergamon Press, Jan. 1, 1984, vol. 22, pp. 27-55 (29 pages).

Communication dated Sep. 30, 2016, issued by the European Patent Office in corresponding European Application No. 14751787.4.

(Continued)

*Primary Examiner* — Sean McGarry
(74) *Attorney, Agent, or Firm* — Sughrue Mion, PLLC

(57) ABSTRACT

The present inventors have found microRNAs which are strongly associated with stabilization of NRF2 in tumors, and an object of the present invention is to provide means for utilizing such miRNAs for the diagnosis and treatment of cancer. The inventors conducted screening of 470 microRNAs in a microRNA library by use of HeLa cells. As a result, 8 miRNAs each exhibiting a large decrease in miRNA activity as compared with a control miRNA, and 8 miRNAs each exhibiting a large increase in miRNA activity as compared with a control miRNA, were identified. The inventors have found that the NRF2 activation in the living body, in particular tumor cells, can be detected by use of the thus-identified miRNAs, whereby malignancy of a tumor, or the like can be differentiated. The inventors have also found that a nucleic acid including a miRNA sequence associated with reduction in the aforementioned ARE activity can be used as a cancer therapeutic agent.

20 Claims, 14 Drawing Sheets

Specification includes a Sequence Listing.

(56) References Cited

FOREIGN PATENT DOCUMENTS

| WO | 2012/121178 A1 | 9/2012 |
|---|---|---|
| WO | 2012/174282 A2 | 12/2012 |

OTHER PUBLICATIONS

Graeser, et al., "Nrf2-dependent gene expression is affected by the proartherogenic apoE4 genotype-studies in targeted gene replacement mice", J Mol Med. May 9, 2011, vol. 89, No. 10, pp. 1027-1035 (9 pages).

International Preliminary Report on Patentability dated Aug. 20, 2015, which issued during the prosecution of Applicant's PCT/JP2014/053594.

International Search Report dated Mar. 18, 2014, which issued during the prosecution of Applicant's PCT/JP2014/053594.

Izumiya, et al., "Functional screening using a microRNA virus library and microarrays : a new high-throughput assay to identify tumor-suppressive microRNAs", Carcinogenesis Advance Access, Jun. 4, 2010, pp. 1-26, 1-14 (40 pages).

Li, et al., "Distinct microRNA expression profiles in acute myeloid leukemia with common translocations", Proceedings of the National Academy of Sciences, Oct. 7, 2008, vol. 105, No. 40, pp. 15535-15540 (6 pages).

Meike Vogler et al., "Small Molecule XIAP Inhibitors Enhance TRAIL-Induced Apoptosis and Antitumor Activity in Preclinical Models of Pancreatic Carcinoma", Cancer Research 69: (6). Mar. 15, 2009. DOI: 10.1158/0008-6472.CAN-08-2436.

Mueller, et al., "miRNA Expression profiling in melanocytes and melanoma cell lines reveals in miRNAs associated with formation and progression of malignant melanoma", Journal of Investigative Dermatology, Jul. 1, 2009, vol. 129, pp. 1740-1751 (12 pages).

Narasimhan, et al., "Identification of Novel microRNAs in Post-Transcriptional Control of Nrf2 Expression and Redox Homeostasis in Neuronal, SH-SY5Y Cells", PLOS ONE, Dec. 7, 2012, vol. 7, No. 12, pp. 1-16 (16 pages).

Östling, et al., "Systematic Analysis of MicroRNAs targeting the androgen receptor in prostate cancer cells", Cancer Research, Mar. 1, 2011, vol. 71, No. 5, pp. 1956-1967 (13 pages).

Shinsuke Yamamoto et al., "Cell Death and Survival: The Impact of miRNA-Based Molecular Diagnostics and Treatment of NRF2-Stabilized Tumors", Molecular Cancer Research; 12(1) Jan. 2014, (12 pages total); Published Online First Dec. 4, 2013; DOI: 10.1158/1541-7786.MCR-13/0246-T.

Singh, et al., "RNAi-Mediated silencing of nuclear factor erythroid-2-related factor 2 gene expression in non-small cell lung cancer inhibits tumor growth and increases efficacy of chemotherapy", Cancer Research, Oct. 1, 2008, vol. 68, No. 19, pp. 7975-7984 (10 pages).

Singh, et al., "MicroRNA-93 regulates NRF2 expression and is associated with breast carcinogenesis", Carcinogenesis, Mar. 14, 2013, vol. 34, No. 5, pp. 1165-1172 (8 pages).

Tsutomu Ohta et al., "Loss of Keap1 Function Activates Nrf2 and Provides Advantages for Lung Cancer Cell Growth", Cancer Research, 2006; 68: (5). Mar. 1, 2008, pp. 1303-1309.

Yamamoto, et al., "The impact of miRNA-Based Molecular Diagnostics and Treatment of NRF2-Stabilized Tumors", Molecular Cancer Research, Jan. 12, 2014, vol. 12, No. 1, pp. 1-15 (15 pages).

Yang, et al., "MiR-28 regulates Nrf2 expression through a Keap1-independent mechanism", Breast Cancer Research and Treatment, Jun. 3, 2011, vol. 129, No. 3, pp. 983-991 (9 pages).

Yoichiro Mitsuishi et al., "Nrf2 Redirects Glucose and Glutamine into Anabolic Pathways in Metabolic Reprogramming", Cell Press, Cancer Cell, Jul. 10, 2012, 22(1): 66-79.

Zijun Xie et al., "Salivary MicroRNAs as Promising Biomarkers for Detection of Esophageal Cancer", PLOS One, vol. 8, Issue 4, Apr. 2013, e57502, pp. 1-11.

Stewart, et. al. "Degradation of Transcription Factor Nrf2 via the Ubiquitin-Proteasome Pathway and Stabilization by Cadmium," The Journal of Biological Chemistry, vol. 278, No. 4, Issue of Jan. 24, 2003, pp. 2396-2402.

Hur, et. al. "A Small-Molecule Inducer of the Antioxidant Response Element," Chemistry & Biology, vol. 17, May 28, 2010, pp. 537-547.

Lister, et al. "Nrf2 is overexpressed in pancreatic cancer: Implications for cell proliferation and therapy," Molecular Cancer, 2011, vol. 10, No. 37; (13 pages) http://www.molecular-cancer.com/content/10/1/37.

Hong, et. al. "Specific Patterns of Electrophile Adduction Trigger Keap1 Ubiquitination and Nrf2 Activation," The Journal of Biological Chemistry, vol. 280, No. 36, Issue of Sep. 9, 2005, pp. 31768-31776.

* cited by examiner

[Fig. 1]
a
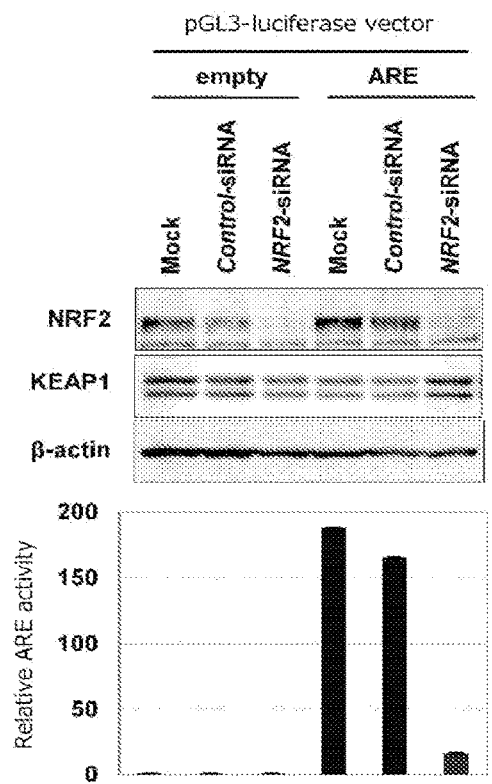
b
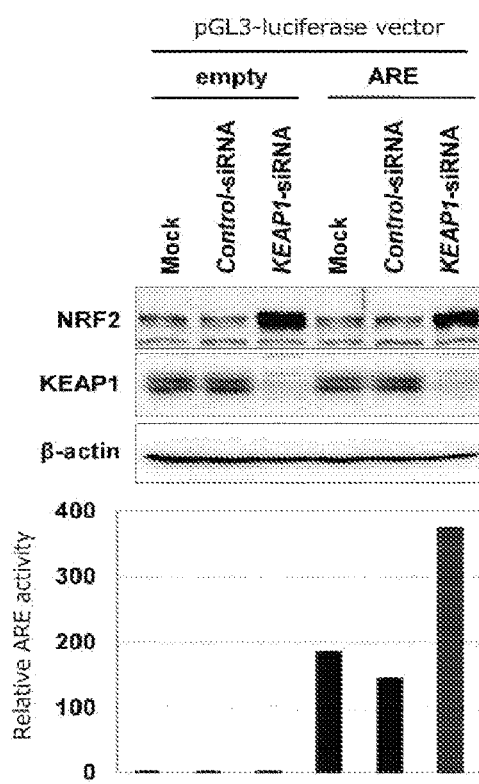

[Fig. 2-1]
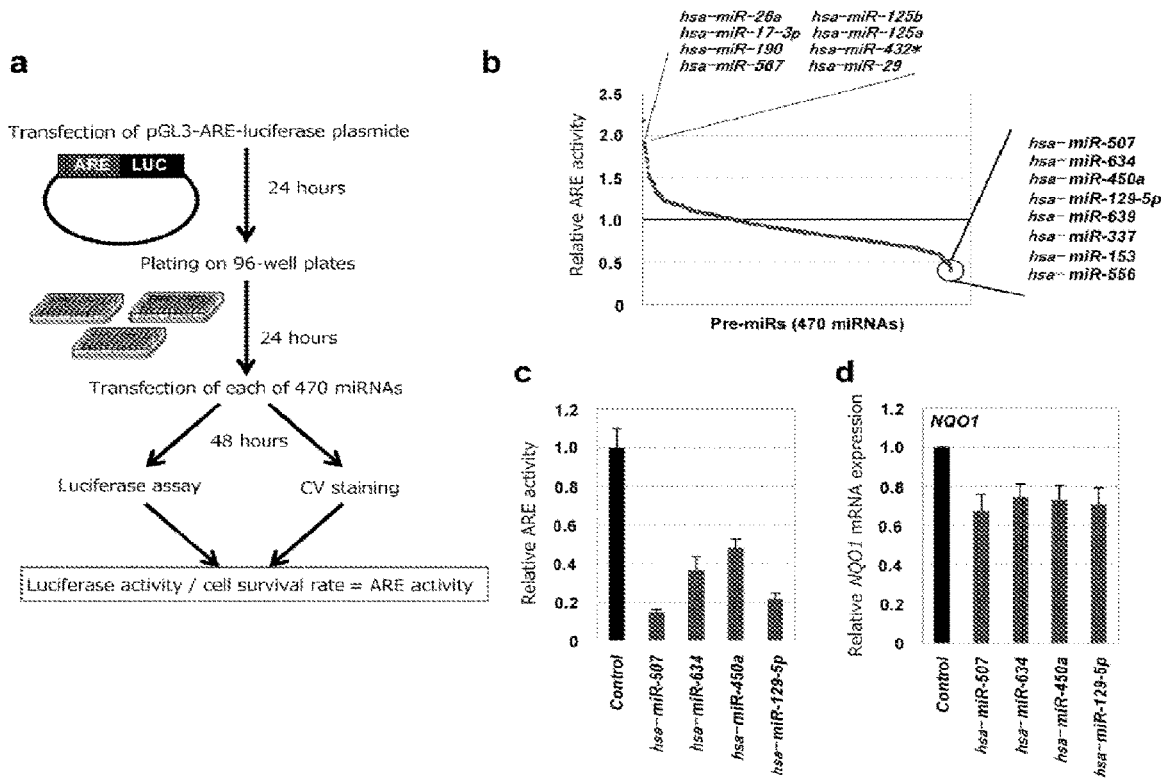

[Fig. 2-2]
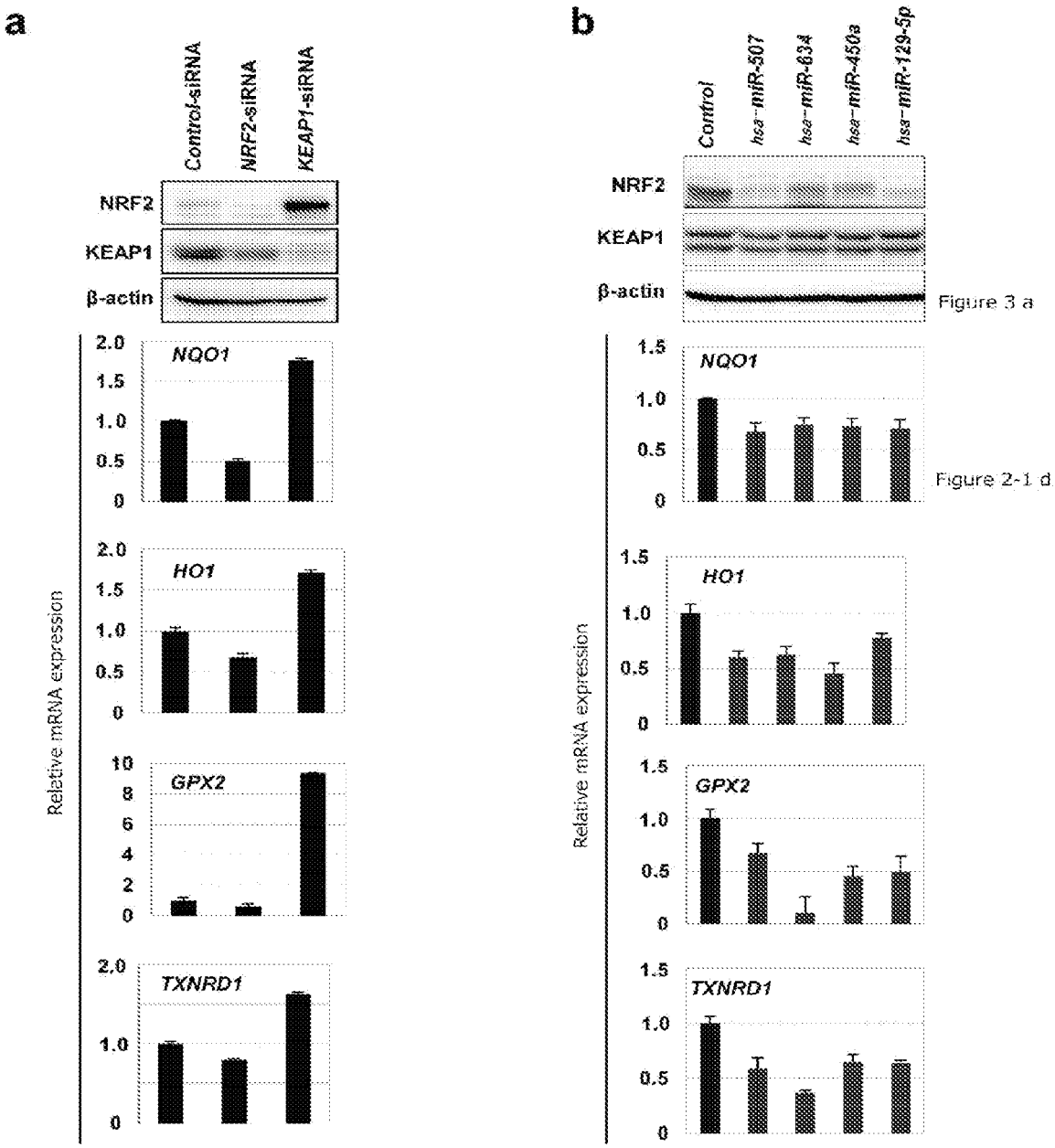

[Fig. 3]
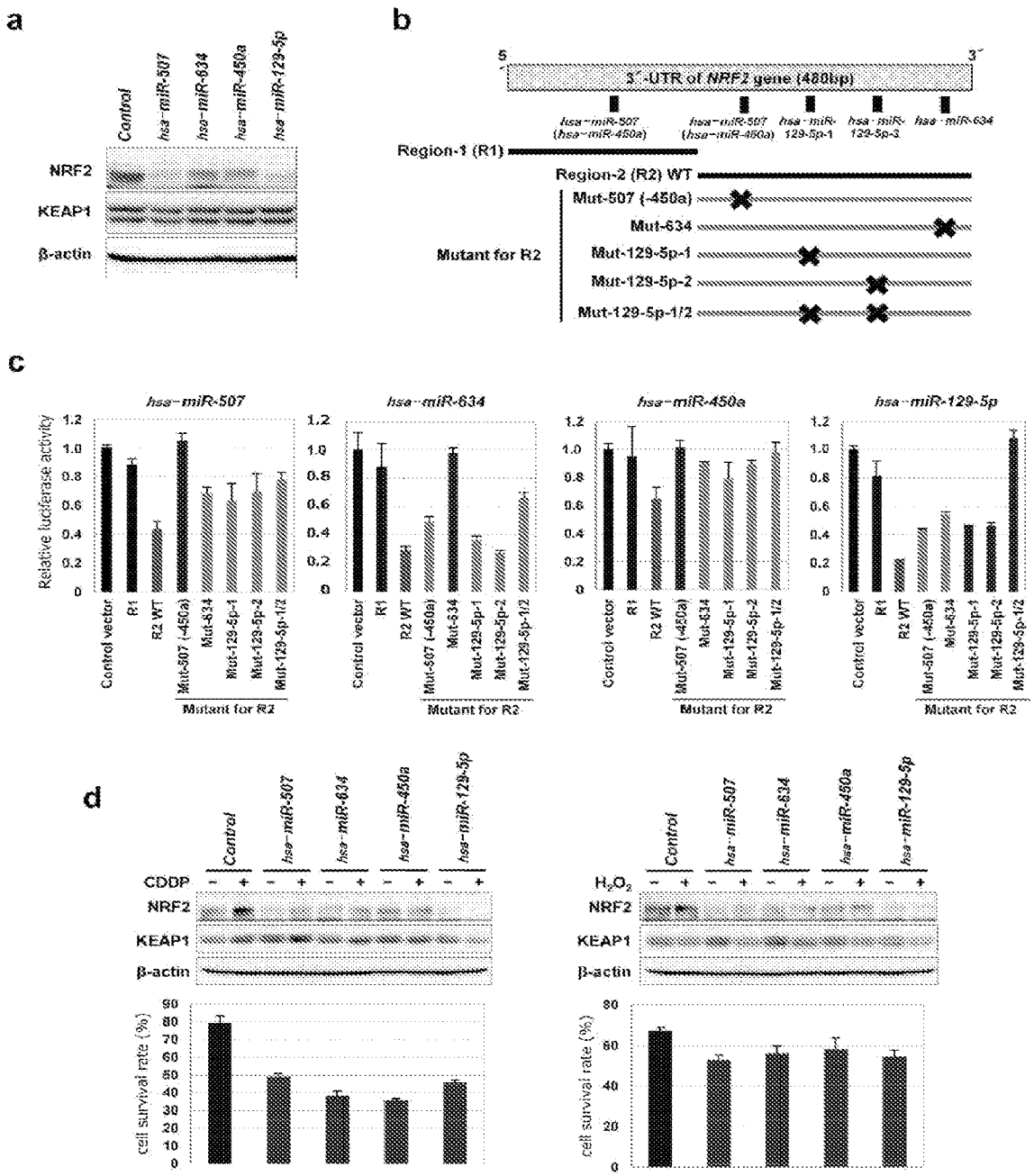

[Fig. 4]
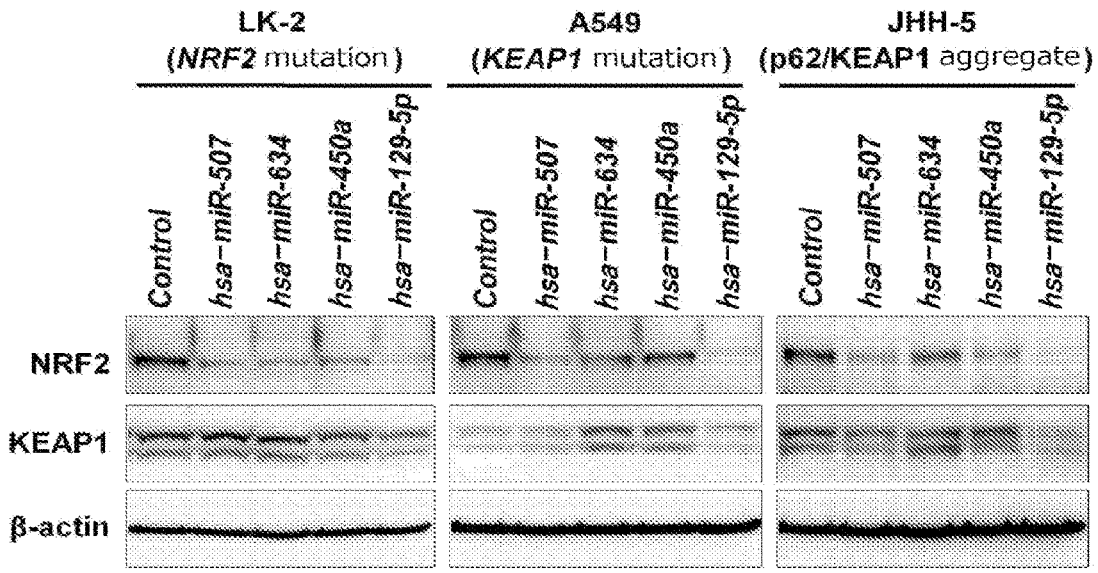
[Fig. 5-1]
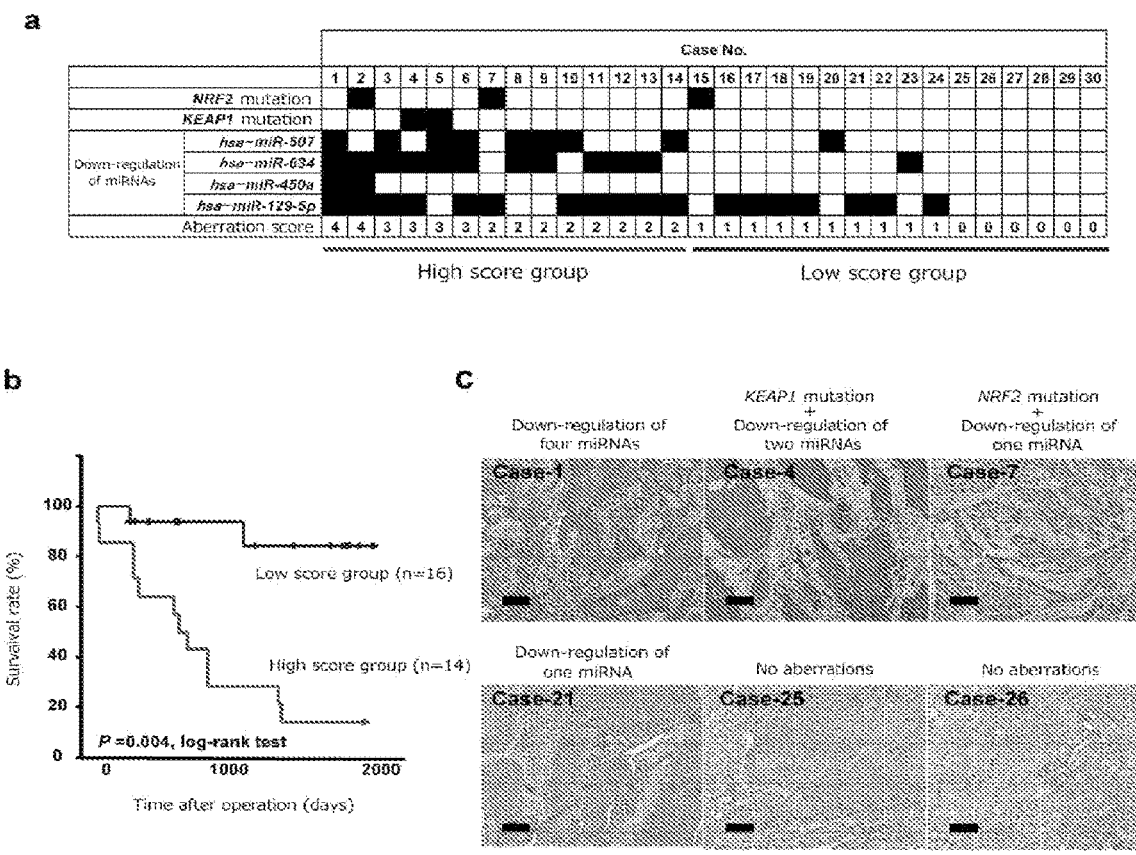

[Fig. 5-2]
a (KRF2)
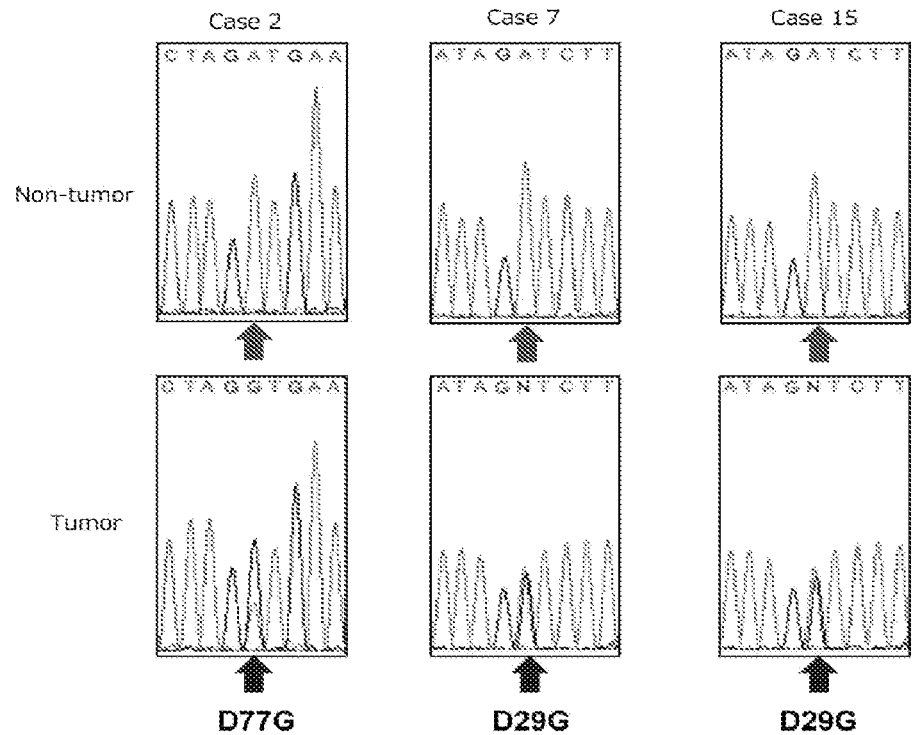
b (KEAP1)
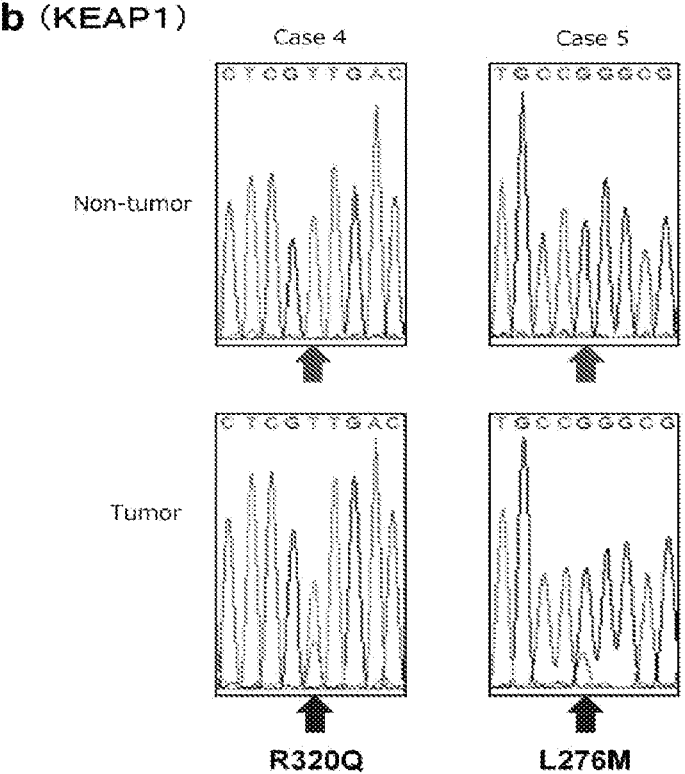

[Fig. 6]
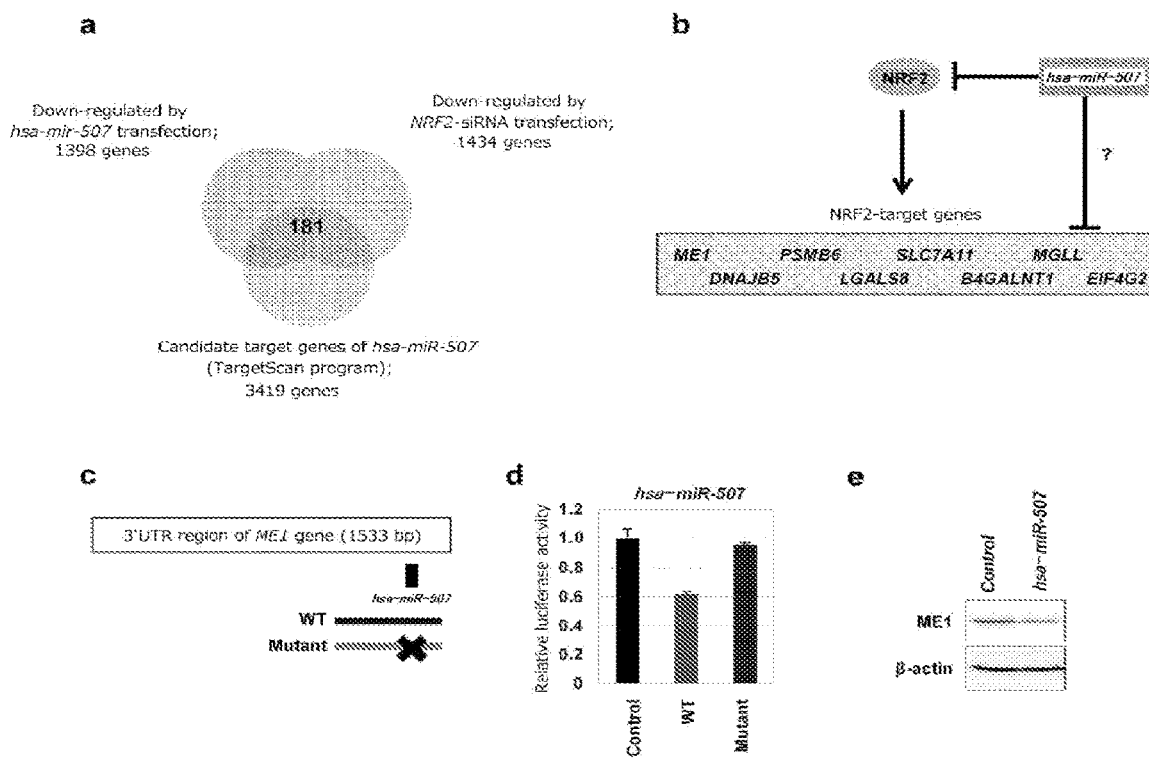

[Fig. 7]
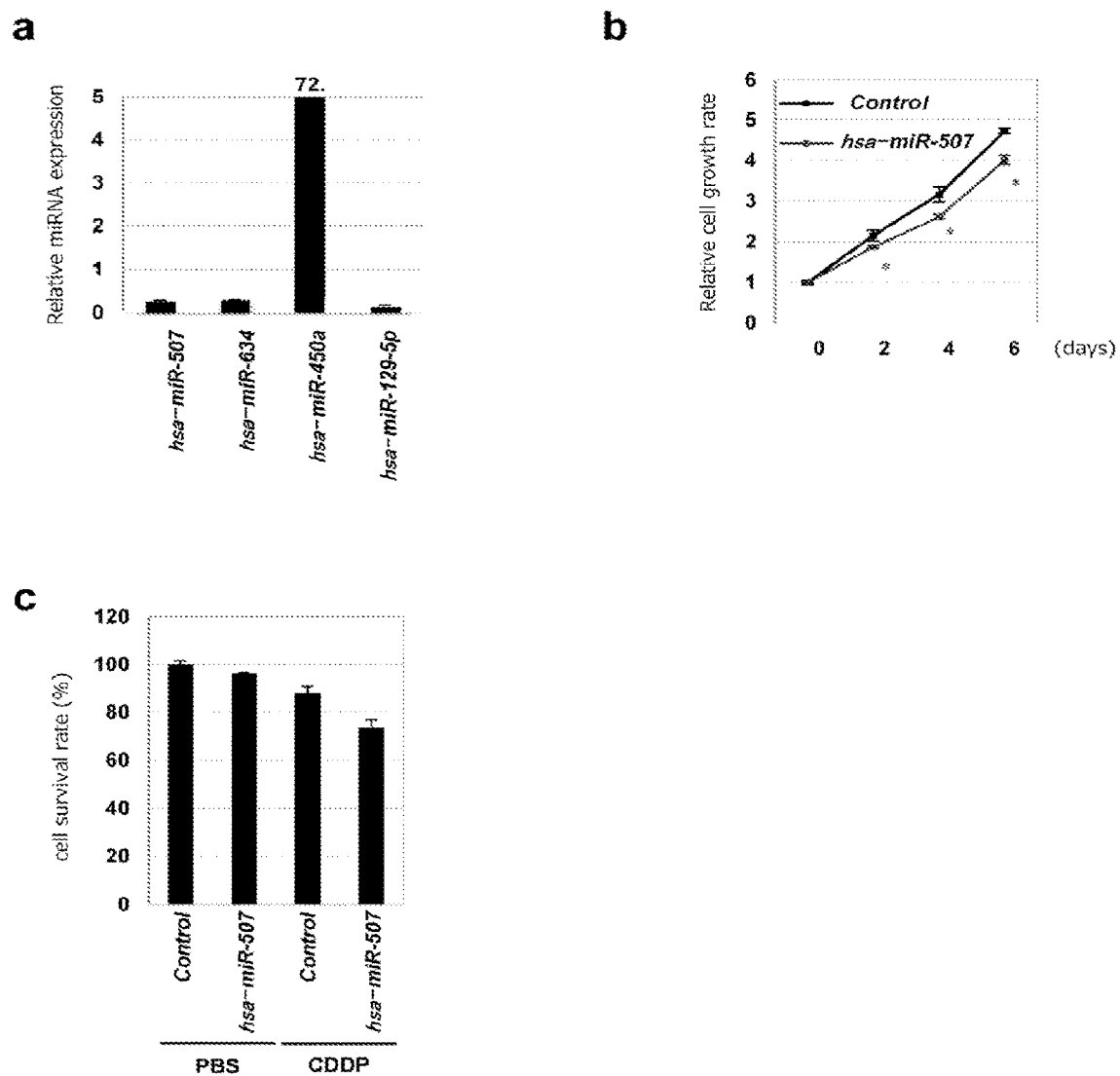

[Fig. 8]
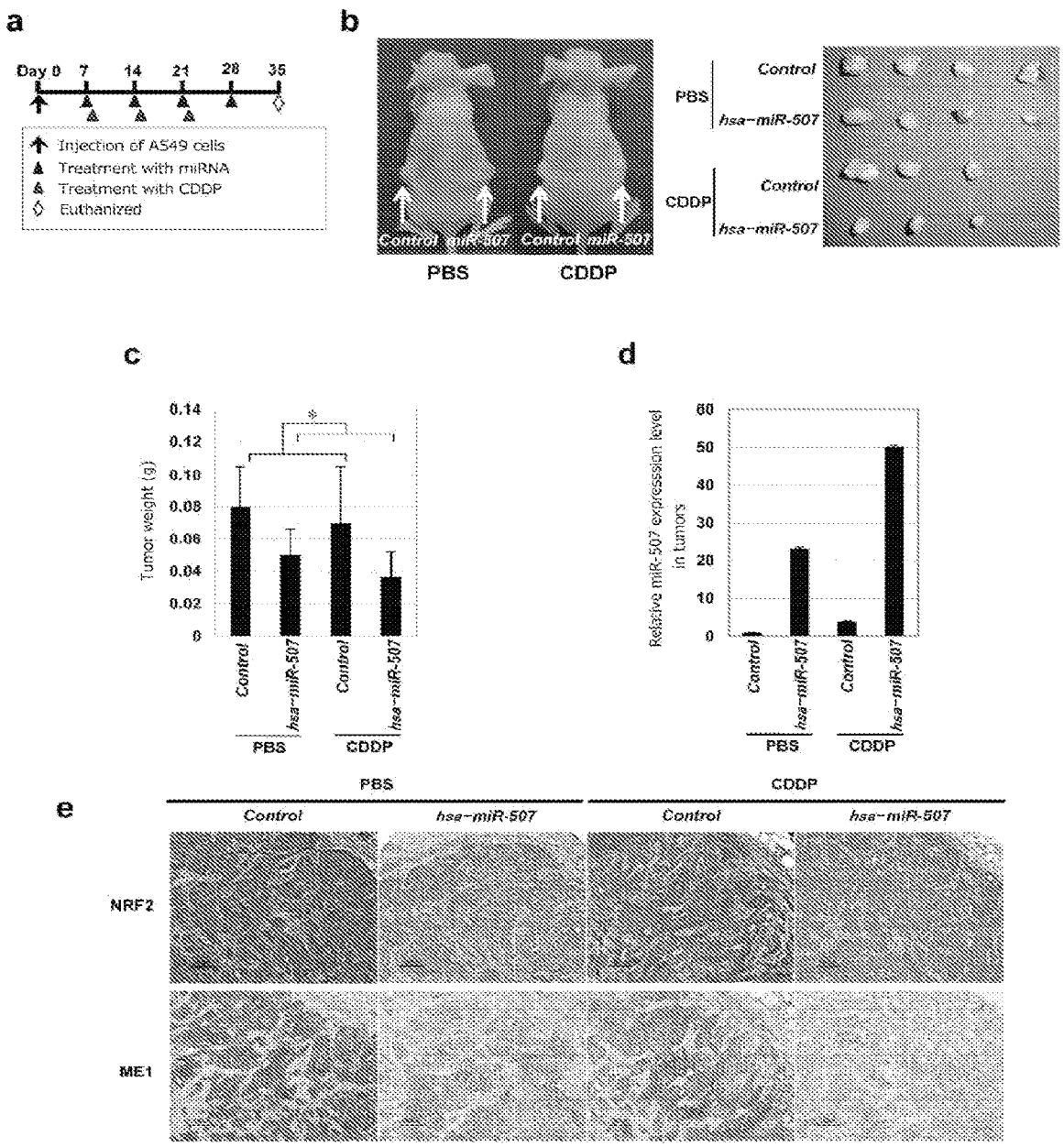

[Fig. 9]
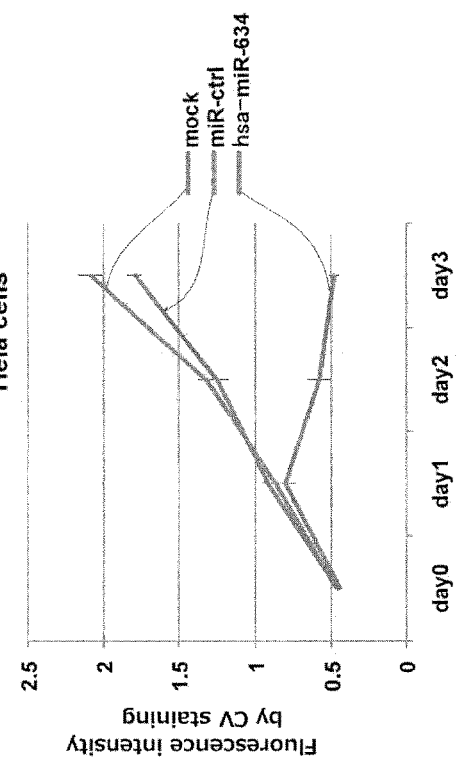
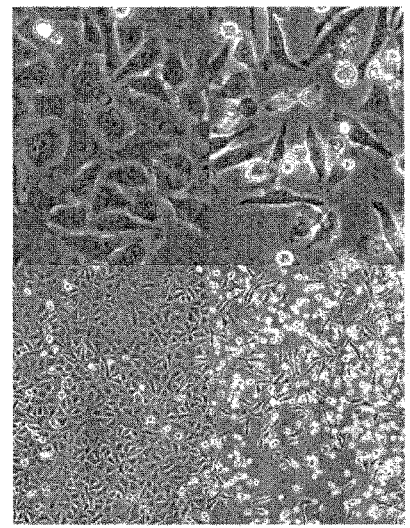
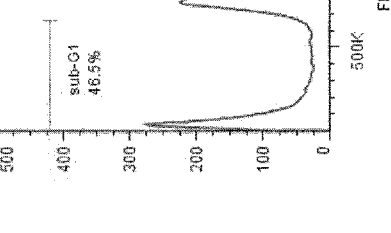
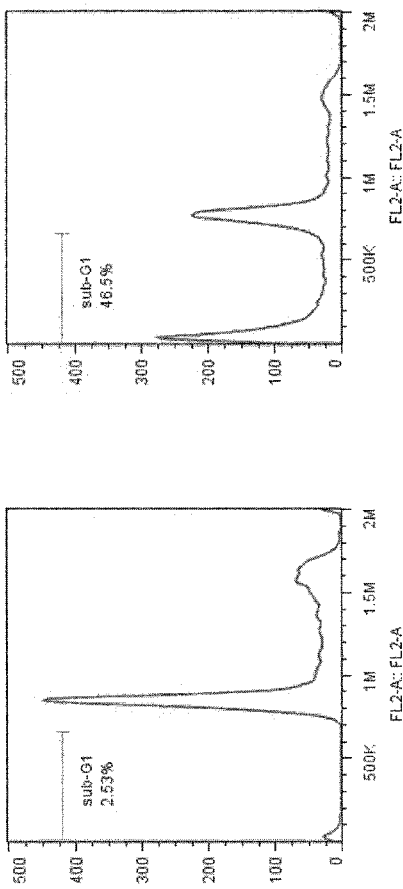

[Fig. 10]
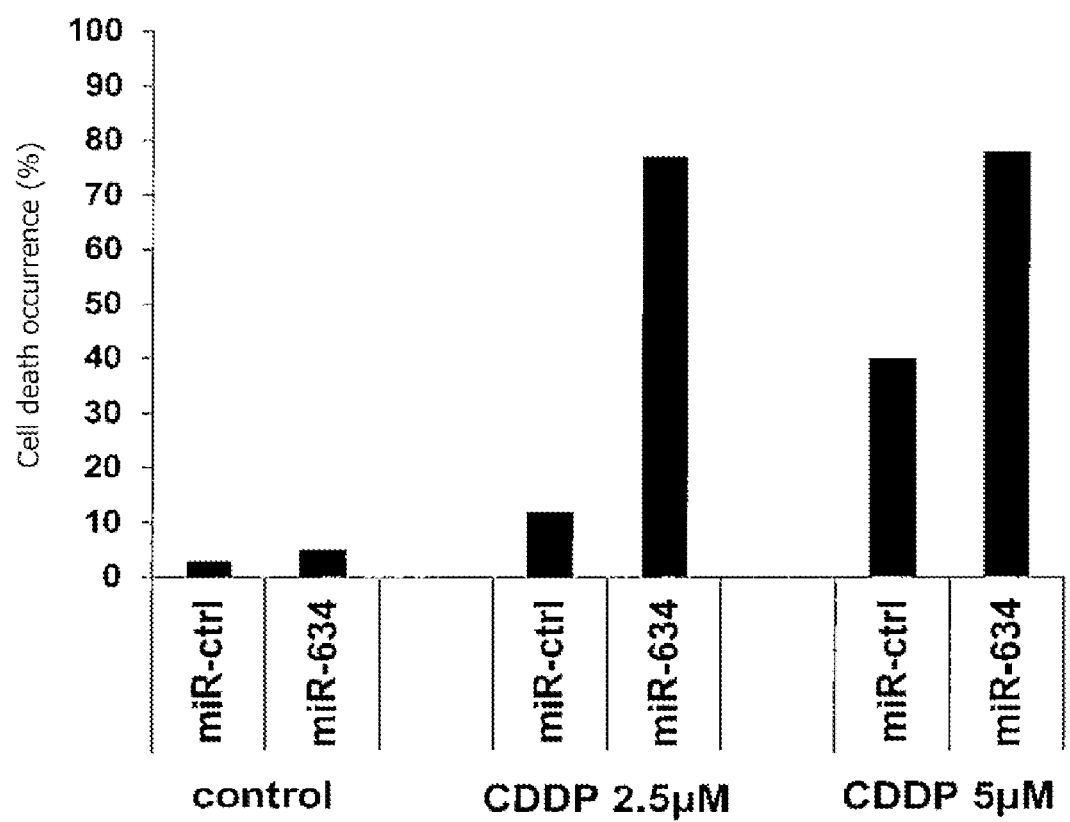

[Fig. 11]
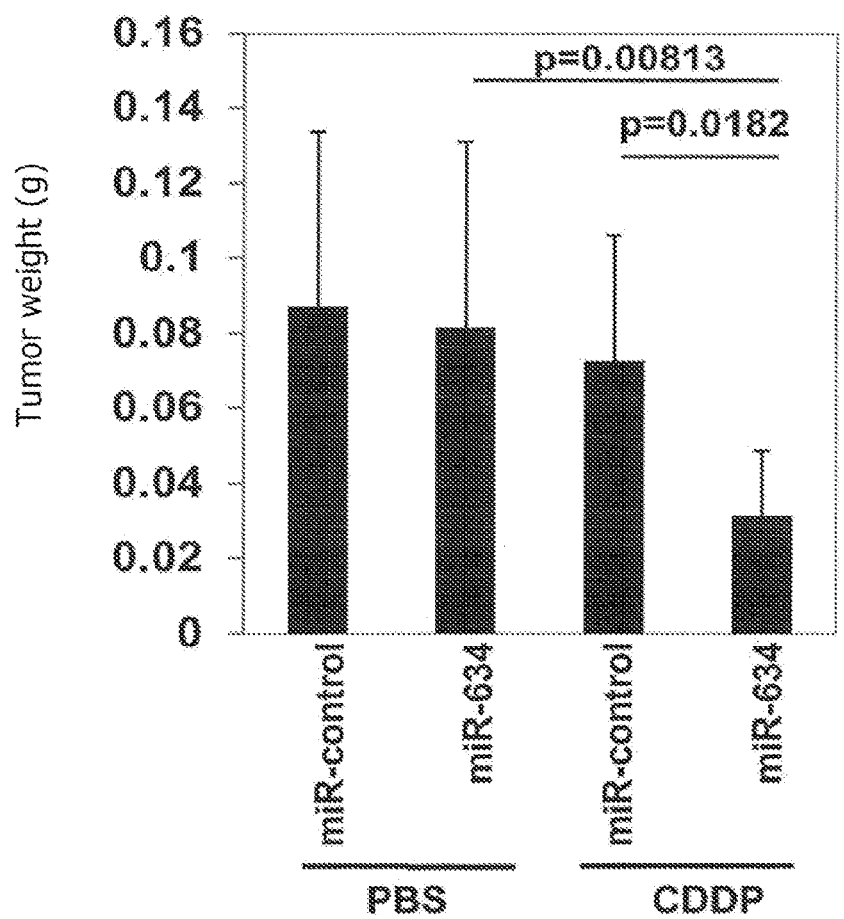

[Fig. 12-1]
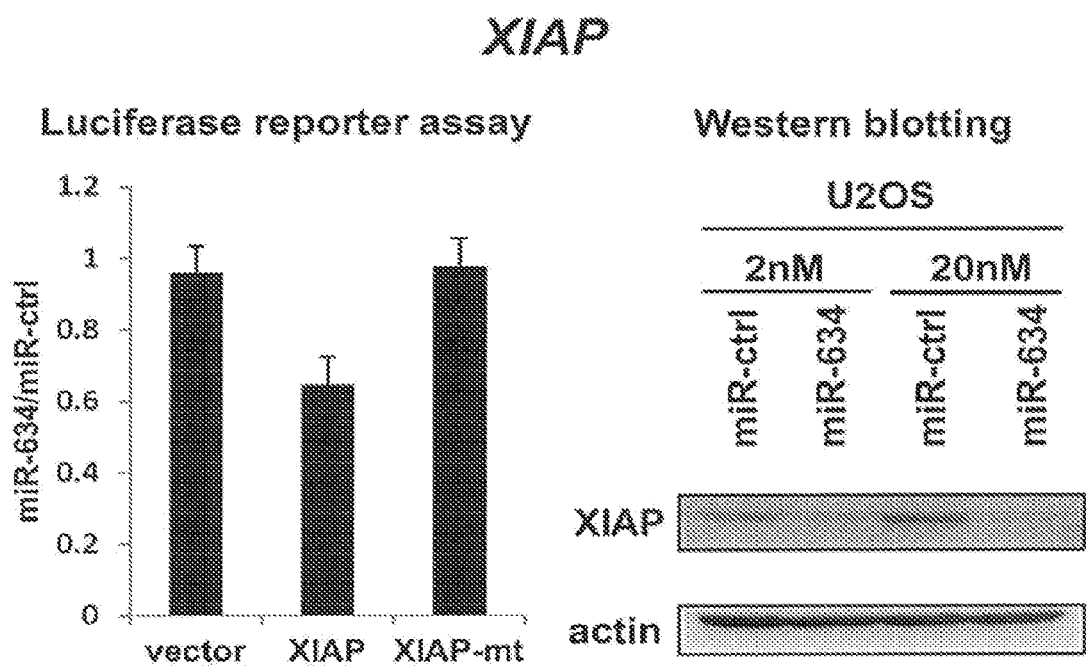
[Fig. 12-2]
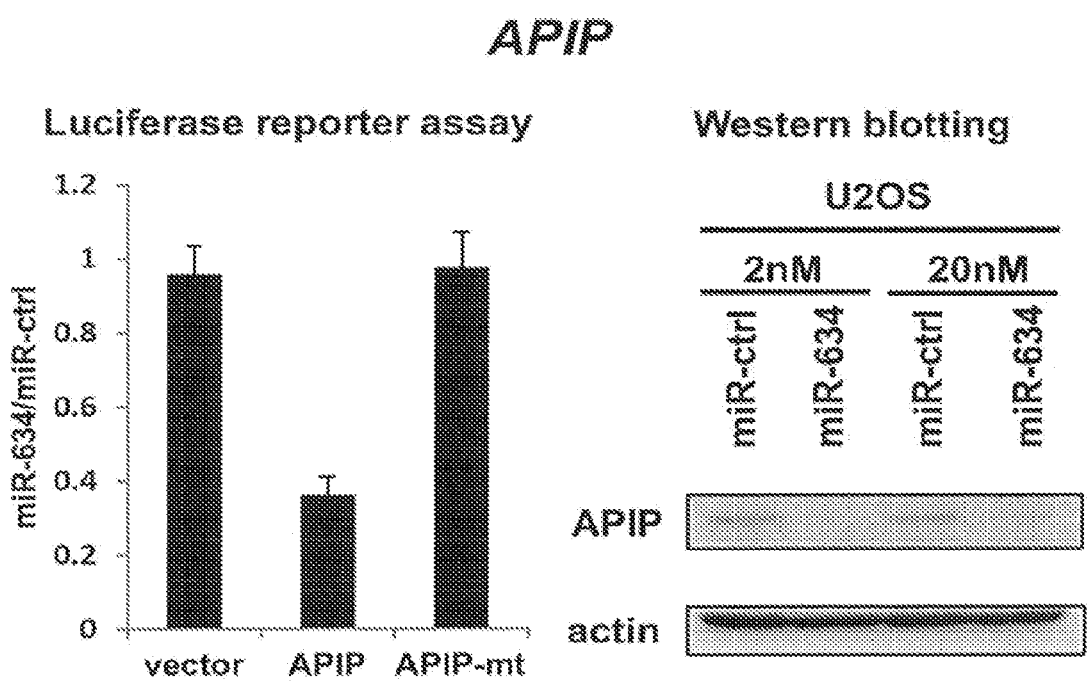

[Fig. 12-3]
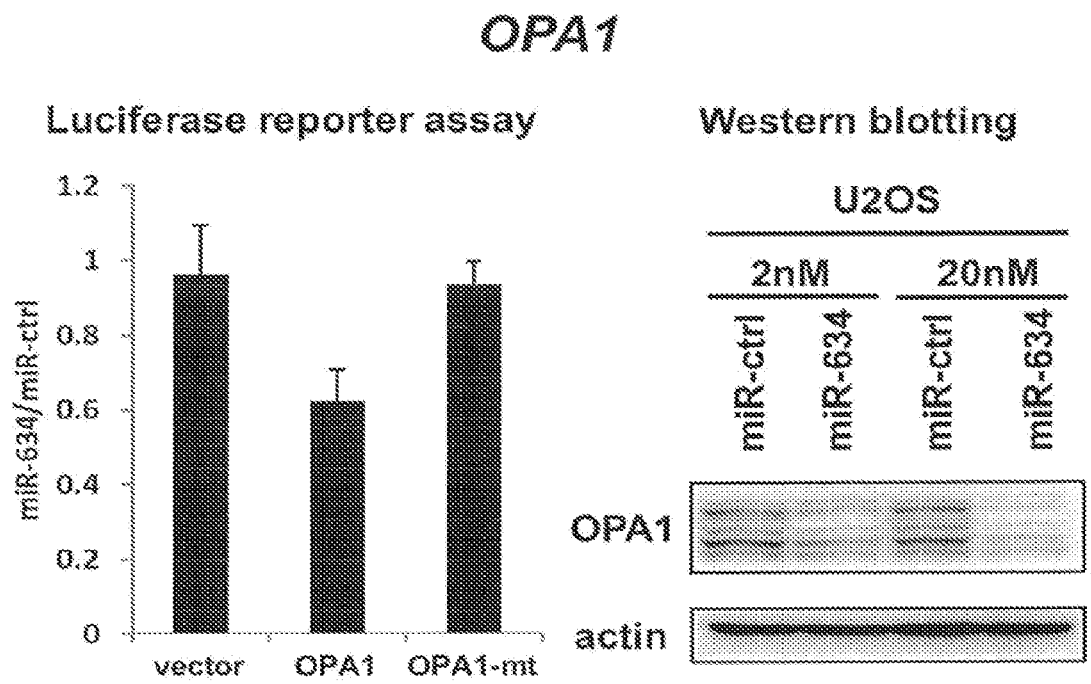
[Fig. 12-4]
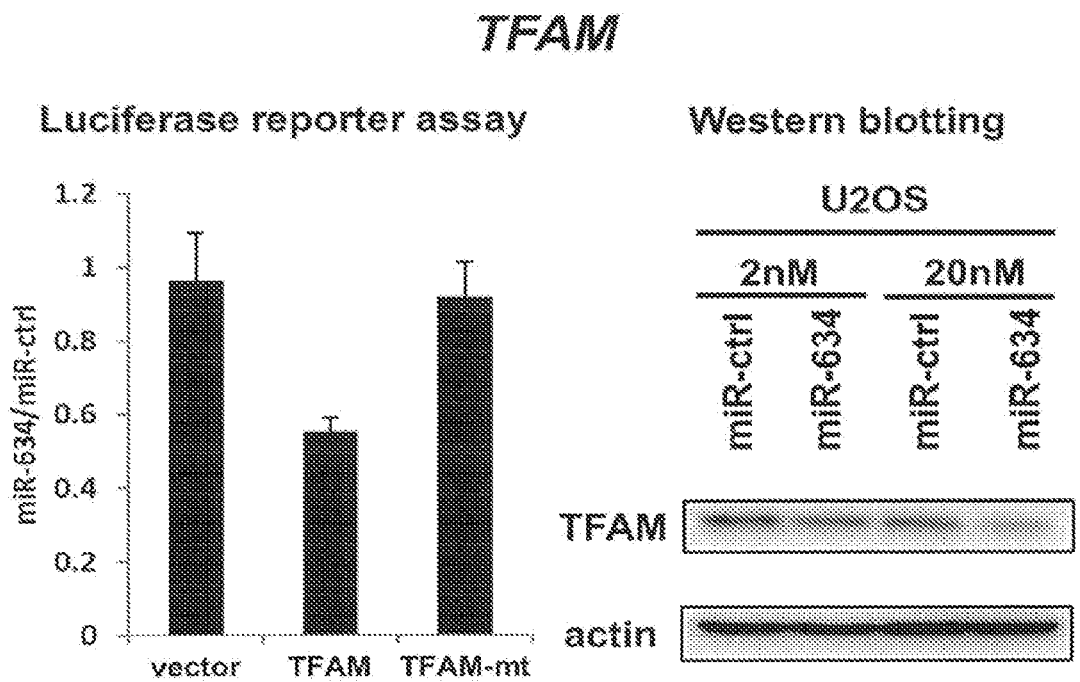

SEQUENCE LISTING

```
<160> NUMBER OF SEQ ID NOS: 55

<210> SEQ ID NO 1
<211> LENGTH: 21
<212> TYPE: RNA
<213> ORGANISM: Homo sapiens

<400> SEQUENCE: 1
uuuugcaccu uuuggaguga a                                                  21

<210> SEQ ID NO 2
<211> LENGTH: 22
<212> TYPE: RNA
<213> ORGANISM: Homo sapiens

<400> SEQUENCE: 2
aaccagcacc ccaacuuugg ac                                                 22
```

-continued

```
<210> SEQ ID NO 3
<211> LENGTH: 22
<212> TYPE: RNA
<213> ORGANISM: Homo sapiens

<400> SEQUENCE: 3
uuuugcgaug uguuccuaau au                                                  22

<210> SEQ ID NO 4
<211> LENGTH: 21
<212> TYPE: RNA
<213> ORGANISM: Homo sapiens

<400> SEQUENCE: 4
cuuuuugcgg ucugggcuug c                                                   21

<210> SEQ ID NO 5
<211> LENGTH: 23
<212> TYPE: RNA
<213> ORGANISM: Homo sapiens

<400> SEQUENCE: 5
aucgcugcgg uugcgagcgc ugu                                                 23

<210> SEQ ID NO 6
<211> LENGTH: 21
<212> TYPE: RNA
<213> ORGANISM: Homo sapiens

<400> SEQUENCE: 6
gaacggcuuc auacaggagu u                                                   21

<210> SEQ ID NO 7
<211> LENGTH: 22
<212> TYPE: RNA
<213> ORGANISM: Homo sapiens

<400> SEQUENCE: 7
uugcauaguc acaaaaguga uc                                                  22

<210> SEQ ID NO 8
<211> LENGTH: 22
<212> TYPE: RNA
<213> ORGANISM: Homo sapiens

<400> SEQUENCE: 8
gaugagcuca uuguaauaug ag                                                  22

<210> SEQ ID NO 9
<211> LENGTH: 21
<212> TYPE: RNA
<213> ORGANISM: Homo sapiens

<400> SEQUENCE: 9
uucaaguaau ccaggauagg c                                                   21

<210> SEQ ID NO 10
<211> LENGTH: 20
<212> TYPE: RNA
<213> ORGANISM: Homo sapiens

<400> SEQUENCE: 10
acugcaguga aggcacuugu                                                     20
```

```
<210> SEQ ID NO 11
<211> LENGTH: 22
<212> TYPE: RNA
<213> ORGANISM: Homo sapiens

<400> SEQUENCE: 11
ugauauguuu gauauauuag gu                                          22

<210> SEQ ID NO 12
<211> LENGTH: 23
<212> TYPE: RNA
<213> ORGANISM: Homo sapiens

<400> SEQUENCE: 12
aguauguucu uccaggacag aac                                         23

<210> SEQ ID NO 13
<211> LENGTH: 22
<212> TYPE: RNA
<213> ORGANISM: Homo sapiens

<400> SEQUENCE: 13
ucccugagac ccuaacuugu ga                                          22

<210> SEQ ID NO 14
<211> LENGTH: 23
<212> TYPE: RNA
<213> ORGANISM: Homo sapiens

<400> SEQUENCE: 14
ucccugagac ccuuuaaccu gug                                         23

<210> SEQ ID NO 15
<211> LENGTH: 21
<212> TYPE: RNA
<213> ORGANISM: Homo sapiens

<400> SEQUENCE: 15
cuggauggcu ccuccauguc u                                           21

<210> SEQ ID NO 16
<211> LENGTH: 21
<212> TYPE: RNA
<213> ORGANISM: Homo sapiens

<400> SEQUENCE: 16
auguaugugu gcaugugcau g                                           21

<210> SEQ ID NO 17
<211> LENGTH: 2859
<212> TYPE: DNA
<213> ORGANISM: Homo sapiens

<400> SEQUENCE: 17
aaatcaggga ggcgcagctc ctacaccaac gcctttccgg ggctccgggt gtgtttgttc   60
caactgttta aactgtttca aagcgtccga actccagcga ccttcgcaaa caactctttc   120
tctcgcgggc gagagcgctg cccttatttg cgggggaggg caaactgaac gccggcaccg   180
gggagctaac ggagaccrcc tctaggtccc ccgcctgctg gaccccagc tggcagtccc    240 ttcccgcccc cggaccgcga gcttcttgcg tcagccccgg cgcgggtggg ggattttcgg   300
aagctcagcc cgcgcggccg gcggggggaag gaagggcccg gactcttgcc ccgcccttgt  360
```

```
ggggcgggag gcggagcggg gcagggaccc gccggcgtgt agccgattac cgagtgccgg    420
ggagcccgga ggagccgccg acgcagccgc caccgccgcc gccgccgcca ccagagccgc    480
cctgtccgcg ccgcgcctcg gcagccggaa cagggccgcc gtcggggagc cccaacacac    540
ggtccacagc tcatcatgat ggacttggag ctgccgccgc cgggactccc gtcccagcag    600
gacatggatt tgattgacat actttggagg caagatatag atcttggagt aagtcgagaa    660
gtatttgact tcagtcagcg acggaaagag tatgagctgg aaaaacagaa aaacttgaa     720 aaggaaagac aagaacaact ccaaaaggag caagagaaag ccttttttcgc tcagttacaa   780 ctagatgaag agacaggtga atttctccca attcagccag cccagcacat ccagtcagaa    840
accagtggat ctgccaacta ctcccaggtt gcccacattc caaatcaga tgctttgtac     900 tttgatgact gcatgcagct tttggcgcag acattcccgt ttgtagatga caatgaggtt    960
tcttcggcta cgtttcagtc acttgttcct gatattcccg gtcacatcga gagcccagtc   1020
ttcattgcta ctaatcaggc tcagtcacct gaaacttctg ttgctcaggt agcccctgtt   1080
gatttagacg gtatgcaaca ggacattgag caagtttggg aggagctatt atccattcct   1140
gagttacagt gtcttaatat tgaaaatgac aagctggttg agactaccat ggttccaagt   1200
ccagaagcca aactgacaga agttgacaat tatcattttt actcatctat accctcaatg   1260
gaaaaagaag taggtaactg tagtccacat tttcttaatg cttttgagga ttccttcagc   1320
agcatcctct ccacagaaga ccccaaccag ttgacagtga actcattaaa ttcagatgcc   1380
acagtcaaca cagattttgg tgatgaattt tattctgctt tcatagctga gcccagtatc   1440
agcaacagca tgccctcacc tgctacttta agccattcac tctctgaact tctaaatggg   1500
cccattgatg tttctgatct atcactttgc aaagctttca accaaaacca ccctgaaagc   1560
acagcagaat tcaatgattc tgactccggc atttcactaa acacaagtcc cagtgtggca   1620
tcaccagaac actcagtgga atcttccagc tatggagaca cactacttgg cctcagtgat   1680
tctgaagtgg aagagctaga tagtgcccct ggaagtgtca acagaatgg tcctaaaaca    1740 ccagtacatt cttctgggga tatggtacaa cccttgtcac catctcaggg gcagagcact   1800
cacgtgcatg atgcccaatg tgagaacaca ccagagaaag aattgcctgt aagtcctggt   1860
catcggaaaa ccccattcac aaaagacaaa cattcaagcc gcttggaggc tcatctcaca   1920
agagatgaac ttagggcaaa agctctccat atcccattcc ctgtagaaaa aatcattaac   1980
ctccctgttg ttgacttcaa cgaaatgatg tccaaagagc agttcaatga agctcaactt   2040
gcattaattc gggatatacg taggaggggt aagaataaag tggctgctca gaattgcaga   2100 aaagaaaac tggaaaatat agtagaacta gagcaagatt tagatcattt gaaagatgaa    2160
aaagaaaaat tgctcaaaga aaaggagaa aatgacaaaa gccttcacct actgaaaaaa    2220
caactcagca ccttatatct cgaagttttc agcatgctac gtgatgaaga tggaaaacct   2280
tattctccta gtgaatactc cctgcagcaa acaagagatg gcaatgtttt ccttgttccc   2340
aaaagtaaga agccagatgt taagaaaaac tagatttagg aggatttgac cttttctgag   2400 ctagttttt tgtactatta tactaaaagc tcctactgtg atgtgaaatg ctcatacttt    2460
ataagtaatt ctatgcaaaa tcatagccaa aactagtata gaaaataata cgaaacttta   2520
aaaagcattg gagtgtcagt atgttgaatc agtagtttca cttaactgt aaacaatttc    2580 ttaggacacc atttgggcta gtttctgtgt aagtgtaaat actacaaaaa cttatttata   2640
ctgttcttat gtcatttgtt atattcatag atttatatga tgatatgaca tctggctaaa   2700
```

| | |
|---|---:|
| aagaaattat tgcaaaacta accactatgt actttttat aaatactgta tggacaaaaa | 2760 |
| atggcatttt ttatattaaa ttgtttagct ctggcaaaaa aaaaaaattt taagagctgg | 2820 |
| tactaataaa ggattattat gactgttaaa ttattaaaa | 2859 |

<210> SEQ ID NO 18
<211> LENGTH: 2577
<212> TYPE: DNA
<213> ORGANISM: Homo sapiens

<400> SEQUENCE: 18

| | |
|---|---:|
| tctgcttagt catggtgacc tgcgcgcgct ccgcgcctcc cccacgcgca gcgatggagg | 60 |
| cgccggggct cgggcggtgg aggcggagcc ggagcgcggc catggcgggg tccctgagtg | 120 |
| ccagaggtgg tggtgttgct tatcttctgg aaccccatgc agccagatcc caggcctagc | 180 |
| ggggctgggg cctgctgccg attcctgccc ctgcagtcac agtgcccctga gggggcaggg | 240 |
| gacgcggtga tgtacgcctc cactgagtgc aaggcggagg tgacgccctc ccagcatggc | 300 |
| aaccgcacct tcagctacac cctggaggat cataccaagc aggcctttgg catcatgaac | 360 |
| gagctgcggc tcagccagca gctgtgtgac gtcacactgc aggtcaagta ccaggatgca | 420 |
| ccggccgccc agttcatggc ccacaaggtg gtgctggcct catccagccc tgtcttcaag | 480 |
| gccatgttca ccaacgggct gcgggagcag ggcatggagg tggtgtccat tgagggtatc | 540 |
| cacccccaagg tcatggagcg cctcattgaa ttcgcctaca cggcctccat ctccatgggc | 600 |
| gagaagtgtg tcctccacgt catgaacggt gctgtcatgt accagatcga cagcgttgtc | 660 |
| cgtgcctgca gtgacttcct ggtgcagcag ctggaccca gcaatgccat cggcatcgcc | 720 |
| aacttcgctg agcagattgg ctgtgtggag ttgcaccagc gtgcccggga gtacatctac | 780 |
| atgcattttg gggaggtggc caagcaagag gagttcttca acctgtccca ctgccaactg | 840 |
| gtgaccctca tcagccggga cgacctgaac gtgcgctgcg agtccgaggt cttccacgcc | 900 |
| tgcatcaact gggtcaagta cgactgcgaa cagcgacggt tctacgtcca ggcgctgctg | 960 |
| cgggccgtgc gctgccactc gttgacgccg aacttcctgc agatgcagct gcagaagtgc | 1020 |
| gagatcctgc agtccgactc ccgctgcaag gactacctgg tcaagatctt cgaggagctc | 1080 |
| accctgcaca gcccacgca ggtgatgccc tgccgggcgc caaggtgggg ccgcctgatc | 1140 |
| tacaccgcgg gcggctactt ccgacagtcg ctcagctacc tggaggctta caaccccagt | 1200 |
| gacggcacct ggctccggtt ggcggacctg caggtgccgc ggagcggcct ggccggctgc | 1260 |
| gtggtgggcg gctgttgta cgccgtgggc ggcaggaaca actcgcccga cggcaacacc | 1320 |
| gactccagcg ccctggactg ttacaacccc atgaccaatc agtggtcgcc ctgcgccccc | 1380 |
| atgagcgtgc cccgtaaccg catcggggtg ggggtcatcg atggccacat ctatgccgtc | 1440 |
| ggcggctccc acgctgcat ccaccacaac agtgtggaga ggtatgagcc agagcgggat | 1500 |
| gagtggcact tggtggcccc aatgctgaca cgaaggatcg gggtgggcgt ggctgtcctc | 1560 |
| aatcgtctcc tttatgccgt gggggctt gacgggacaa accgccttaa ttcagctgag | 1620 |
| tgttactacc cagagaggaa cgagtggcga atgatcacag caatgaacac catccgaagc | 1680 |
| ggggcaggcg tctgcgtcct gcacaactgt atctatgctg ctgggggcta tgatggtcag | 1740 |
| gaccagctga acagcgtgga gcgctacgat gtggaaacag agacgtggac tttcgtagcc | 1800 |
| cccatgaagc accggcgaag tgccctgggg atcactgtcc accaggggag aatctacgtc | 1860 |
| cttggaggct atgatggtca cacgttcctg gacagtgtgg agtgttacga cccagataca | 1920 |
| gacacctgga gcgaggtgac ccgaatgaca tcgggccgga gtggggtggg cgtggctgtc | 1980 |

```
accatggagc cctgccggaa gcagattgac cagcagaact gtacctgttg aggcactttt    2040
gtttcttggg caaaaataca gtccaatggg gagtatcatt gttttgtac aaaaaccggg     2100 actaaaagaa aagacagcac tgcaaataac ccatcttccg ggaagggagg ccaggatgcc    2160
tcagtgttaa aatgacatct caaaagaagt ccaaagcggg aatcatgtgc ccctcagcgg    2220
agccccggga gtgtccaaga cagcctggct gggaaggggg gtgtggaaag agcaggcttc    2280
caggagagag gccccaaac cctctggccg ggtaataggc ctgggtccca ctcacccatg     2340
ccggcagctg tcaccatgtg atttattctt ggatacctgg gaggggggcca atgggggcct  2400 caggggagg ccccctctgg aaatgtggtt cccaggatg ggcctgtaca tagaagccac     2460
cggatggcac ttccccaccg gatggacagt tattttgttg ataagtaacc ctgtaatttt   2520
ccaaggaaaa taagaacag actaactagt gtctttcacc ctgaaaaaaa aaaaaaa       2577
```

<210> SEQ ID NO 19
<211> LENGTH: 41
<212> TYPE: DNA
<213> ORGANISM: Homo sapiens

<400> SEQUENCE: 19

```
ctcagccttc aaatcgcag tcacagtgac tcagcagaat c                         41
```

<210> SEQ ID NO 20
<211> LENGTH: 58
<212> TYPE: DNA
<213> ORGANISM: Homo sapiens

<400> SEQUENCE: 20

```
cgacgcgtct cagccttcca aatcgcagtc acagtgactc agcagaatcc tcgagcgg      58
```

<210> SEQ ID NO 21
<211> LENGTH: 58
<212> TYPE: DNA
<213> ORGANISM: Homo sapiens

<400> SEQUENCE: 21

```
ccgctcgagg attctgctga gtcactgtga ctgcgatttg gaaggctgag acgcgtcg      58
```

<210> SEQ ID NO 22
<211> LENGTH: 23
<212> TYPE: DNA
<213> ORGANISM: Artificial
<220> FEATURE:
<223> OTHER INFORMATION: Primer

<400> SEQUENCE: 22

```
accatcaaca gtggcataat gtg                                            23
```

<210> SEQ ID NO 23
<211> LENGTH: 26
<212> TYPE: DNA
<213> ORGANISM: Artificial
<220> FEATURE:
<223> OTHER INFORMATION: Primer

<400> SEQUENCE: 23

```
gcaaatggat tctgcttcac ctactt                                         26
```

<210> SEQ ID NO 24
<211> LENGTH: 26
<212> TYPE: DNA

```
<213> ORGANISM: Artificial
<220> FEATURE:
<223> OTHER INFORMATION: Primer

<400> SEQUENCE: 24
catcacaatg tacgcggttc ctatta                                          26

<210> SEQ ID NO 25
<211> LENGTH: 26
<212> TYPE: DNA
<213> ORGANISM: Artificial
<220> FEATURE:
<223> OTHER INFORMATION: Primer

<400> SEQUENCE: 25
gatgaacctg tctctttaag ggggaa                                          26

<210> SEQ ID NO 26
<211> LENGTH: 30
<212> TYPE: DNA
<213> ORGANISM: Artificial
<220> FEATURE:
<223> OTHER INFORMATION: Primer

<400> SEQUENCE: 26
gtgagaaggg agaggagaga ggaaaggtct                                      30

<210> SEQ ID NO 27
<211> LENGTH: 26
<212> TYPE: DNA
<213> ORGANISM: Artificial
<220> FEATURE:
<223> OTHER INFORMATION: Primer

<400> SEQUENCE: 27
aagagactaa ggttttgcta tgttgc                                          26

<210> SEQ ID NO 28
<211> LENGTH: 20
<212> TYPE: DNA
<213> ORGANISM: Artificial
<220> FEATURE:
<223> OTHER INFORMATION: Primer

<400> SEQUENCE: 28
cattctgaaa ggctggtttg                                                 20

<210> SEQ ID NO 29
<211> LENGTH: 20
<212> TYPE: DNA
<213> ORGANISM: Artificial
<220> FEATURE:
<223> OTHER INFORMATION: Primer

<400> SEQUENCE: 29
gctacctggg tgacctgtct                                                 20

<210> SEQ ID NO 30
<211> LENGTH: 22
<212> TYPE: DNA
<213> ORGANISM: Artificial
<220> FEATURE:
<223> OTHER INFORMATION: Primer

<400> SEQUENCE: 30
ggctttcatt gccaagtcct tc                                              22
```

<210> SEQ ID NO 31
<211> LENGTH: 24
<212> TYPE: DNA
<213> ORGANISM: Artificial
<220> FEATURE:
<223> OTHER INFORMATION: Primer

<400> SEQUENCE: 31 cttttcatt cctgctactc tacc                                              24

<210> SEQ ID NO 32
<211> LENGTH: 24
<212> TYPE: DNA
<213> ORGANISM: Artificial
<220> FEATURE:
<223> OTHER INFORMATION: Primer

<400> SEQUENCE: 32
cggagtcaac ggatttggtc gtat                                             24

<210> SEQ ID NO 33
<211> LENGTH: 24
<212> TYPE: DNA
<213> ORGANISM: Artificial
<220> FEATURE:
<223> OTHER INFORMATION: Primer

<400> SEQUENCE: 33
ggcaaagctg gaactcaaat ccag                                             24

<210> SEQ ID NO 34
<211> LENGTH: 26
<212> TYPE: DNA
<213> ORGANISM: Artificial
<220> FEATURE:
<223> OTHER INFORMATION: Primer

<400> SEQUENCE: 34
tcaaactgtg gagactacac caccat                                           26

<210> SEQ ID NO 35
<211> LENGTH: 26
<212> TYPE: DNA
<213> ORGANISM: Artificial
<220> FEATURE:
<223> OTHER INFORMATION: Primer

<400> SEQUENCE: 35
ggcacagaat caaaggtcac tgacta                                           26

<210> SEQ ID NO 36
<211> LENGTH: 30
<212> TYPE: DNA
<213> ORGANISM: Artificial
<220> FEATURE:
<223> OTHER INFORMATION: Primer

<400> SEQUENCE: 36
ggagagagag aagcttggac tctatcagaa                                       30

<210> SEQ ID NO 37
<211> LENGTH: 31
<212> TYPE: DNA
<213> ORGANISM: Artificial
<220> FEATURE:

<223> OTHER INFORMATION: Primer

<400> SEQUENCE: 37
tccagctggg caacagagcg agaccttgtt t                               31

<210> SEQ ID NO 38
<211> LENGTH: 26
<212> TYPE: DNA
<213> ORGANISM: Artificial
<220> FEATURE:
<223> OTHER INFORMATION: Primer

<400> SEQUENCE: 38
agctgaaact gaaggacaac tgtgtg                                     26

<210> SEQ ID NO 39
<211> LENGTH: 20
<212> TYPE: DNA
<213> ORGANISM: Artificial
<220> FEATURE:
<223> OTHER INFORMATION: Primer

<400> SEQUENCE: 39
ggctgcttgg agcaaaatac                                            20

<210> SEQ ID NO 40
<211> LENGTH: 20
<212> TYPE: DNA
<213> ORGANISM: Artificial
<220> FEATURE:
<223> OTHER INFORMATION: Primer

<400> SEQUENCE: 40
gggcagaatc ttgcactttg                                            20

<210> SEQ ID NO 41
<211> LENGTH: 25
<212> TYPE: DNA
<213> ORGANISM: Artificial
<220> FEATURE:
<223> OTHER INFORMATION: Primer

<400> SEQUENCE: 41
ctatatggca actttaagga ggcgc                                      25

<210> SEQ ID NO 42
<211> LENGTH: 21
<212> TYPE: DNA
<213> ORGANISM: Artificial
<220> FEATURE:
<223> OTHER INFORMATION: Primer

<400> SEQUENCE: 42
ctctctcctt ttccctttc c                                           21

<210> SEQ ID NO 43
<211> LENGTH: 24
<212> TYPE: DNA
<213> ORGANISM: Artificial
<220> FEATURE:
<223> OTHER INFORMATION: Primer

<400> SEQUENCE: 43
agccttctcc atggtggtga agac                                       24

```
<210> SEQ ID NO 44
<211> LENGTH: 21
<212> TYPE: RNA
<213> ORGANISM: Artificial
<220> FEATURE:
<223> OTHER INFORMATION: Probe

<400> SEQUENCE: 44
uuuugcaccu uuuggaguga a                                              21

<210> SEQ ID NO 45
<211> LENGTH: 22
<212> TYPE: RNA
<213> ORGANISM: Artificial
<220> FEATURE:
<223> OTHER INFORMATION: Probe

<400> SEQUENCE: 45
aaccagcacc ccaacuuugg ac                                             22

<210> SEQ ID NO 46
<211> LENGTH: 22
<212> TYPE: RNA
<213> ORGANISM: Artificial
<220> FEATURE:
<223> OTHER INFORMATION: Probe

<400> SEQUENCE: 46
uuuugcgaug uguuccuaau au                                             22

<210> SEQ ID NO 47
<211> LENGTH: 21
<212> TYPE: RNA
<213> ORGANISM: Artificial
<220> FEATURE:
<223> OTHER INFORMATION: Probe

<400> SEQUENCE: 47
cuuuuugcgg ucugggcuug c                                              21

<210> SEQ ID NO 48
<211> LENGTH: 42
<212> TYPE: RNA
<213> ORGANISM: Artificial
<220> FEATURE:
<223> OTHER INFORMATION: Probe

<400> SEQUENCE: 48
cgcaaggaug acacgcaaau ucgugaagcg uuccauauuu uu                       42

<210> SEQ ID NO 49
<211> LENGTH: 486
<212> TYPE: DNA
<213> ORGANISM: Homo sapiens

<400> SEQUENCE: 49
atttaggagg atttgacctt ttctgagcta gtttttttgt actattatac taaaagctcc    60
tactgtgatg tgaaatgctc atactttata agtaattcta tgcaaaatca tagccaaaac   120
tagtatagaa aataatacga aactttaaaa agcattggag tgtcagtatg ttgaatcagt   180
agtttcactt taactgtaaa caattt ctta ggacaccatt tgggctagtt tctgtgtaag   240
tgtaaatact acaaaaactt атттататсtg tt cttatgtc attt gttata tt cатagатт   300

tatatgatga tatgacatct ggctaaaaag aattatt gc aaaactaacc actatgtact   360
```

| | |
|---|---|
| tttttataaa tactgtatgg acaaaaaatg gcattttta tattaaattg tttagctctg | 420 |
| gcaaaaaaaa aaaattttaa gagctggtac taataaagga ttattatgac tgttaaatta | 480 |
| ttaaaa | 486 |

<210> SEQ ID NO 50
<211> LENGTH: 1535
<212> TYPE: DNA
<213> ORGANISM: Homo sapiens

<400> SEQUENCE: 50

| | |
|---|---|
| gataatagca aacatttcta actctattaa tgaggtcttt aaacctttca taattttaa | 60 |
| aggttggaat cttttataat gattcataag acacttagat taagatttta ctttaacagt | 120 |
| ctaaaaattg atagaagaat atcgatataa attgggataa acatcacatg agacaatttt | 180 |
| gcttcacttt gccttctggt tatttatggt ttctgtctga attattctgc ctacgttctc | 240 |
| tttaaaagct gttgtacgta ctacggagaa actcatcatt tttatacagg acactaatgg | 300 |
| gaagaccaaa attactaata aattgacata accaacatta aaactcataa ttattttgtt | 360 |
| gaccattttg ttaaaatcta cttttcaaaa aaaaaaagct agaaatgaat ctaggcgtag | 420 |
| gtgaacttt gctaagcaga aataacacta ctttgttgcc tagagaaaga taacttctca | 480 |
| agtattttta ttccagtcct agatcatata tgttcttttg tgcaacggaa ttctaacagt | 540 |
| tctaagagaa agatcactgc tgtttacagc gccttgtgca gccttagatt ttaatattct | 600 |
| tttgtcattg ttacatctca tagagtaaag ctcttattac cttgatcctg agtcagaaat | 660 |
| cccacctgaa atcacctttt ttcccccttg atcaaacatc ccatccttca gctaccatac | 720 |
| tgttgctaca gggattttgt ggactgtggc ccctgtcccg aggttggcac cttcagttca | 780 |
| gcacagcctg agcagtgaga aggtctgaaa ggagagtata tagttaagat ccttgagaaa | 840 |
| gggctgcctg aggaactgac ctcttaaaga tctcaggatc tttaagacaa caagttaggt | 900 |
| tcctactgga gttacctgcc agaatggcct cttaattaac tcaggtaatg aagagctaac | 960 |
| tgtgttataa tcatcttgct tttgcctgaa tttggagaaa gtattataat taagttccca | 1020 |
| gtatcagaaa tgtccttaca taagattaaa atatcttgat gactaatacc attctatgag | 1080 |
| aaagagtagt tatatgccca gactgtatta atttacttta gaaactaatg tttgaagtaa | 1140 |
| tggaaaaaat tttaaattat aaagctaagg tgcaataaca tttgctactt atttatagaa | 1200 |
| ttatttgaag aattttgttt tgaagtaat gctttaagga gtataagata ttcaagataa | 1260 |
| attatactat aaaatgattt tattgaaagt tgaaggttac acaaattgtt ttaggtatga | 1320 |
| gcagaagagg ttaaggtatt tctaaaggta acatatagtc aagagtttcc tcaaaatagt | 1380 |
| tatttggaga agaatcagaa tgtctgtgta tttcttgtct gtttctatgt tgtcttatag | 1440 |
| ctctgactaa atgtgtttac ctatgcaaaa gatttattaa agcatagaaa aggtgaatga | 1500 |
| ataaaaatat aaaataattg tccttttct taaaa | 1535 |

<210> SEQ ID NO 51
<211> LENGTH: 1585
<212> TYPE: DNA
<213> ORGANISM: Homo sapiens

<400> SEQUENCE: 51

| | |
|---|---|
| gattccttag cctggatttc cttctaacat gttatcaaat ctgggtatct ttccaggctt | 60 |
| ccctgacttg ctttagtttt taagatttgt gttttctttt ttccacaagg aataaatgag | 120 |
| agggaatcga ctgtattcgt gcattttttgg atcatttta actgattctt atgattacta | 180 |

-continued

| | |
|---|---|
| tcatggcata taaccaaaat ccgactgggc tcaagaggcc acttagggaa agatgtagaa | 240 |
| agatgctaga aaaatgttct ttaaaggcat ctacacaatt taattcctct ttttagggct | 300 |
| aaagttttag ggtacagttt ggctaggtat cattcaactc tccaatgttc tattaatcac | 360 |
| ctctctgtag tttatggcag aagggaattg ctcagagaag gaaaagactg aatctacctg | 420 |
| ccctaaggga cttaacttgt ttggtagtta gccatctaat gcttgtttat gatatttctt | 480 |
| gctttcaatt acaaagcagt tactaatatg cctagcacaa gtaccactct tggtcagctt | 540 |
| ttgttgttta tatacagtac acagatacct tgaaaggaag agctaataaa tctcttcttt | 600 |
| gctgcagtca tctacttttt ttttaattaa aaaaaatttt tttttgaagc agtcttgctc | 660 |
| tgttacccag gctggagtgc agtggtgtga tctcggctca ctgcaacctc tgcctcccag | 720 |
| gttccagcaa ttctcctgcc tcagcctccc tagtagctgg gatgacaggc gcctgccatc | 780 |
| atgcctgact aattttttgta ttttttagtag agacggcgtt tcaccatgtt ggccaggctg | 840 |
| gtctcaaact cctgacctca ggtgatccgc ctacctcagc ctcccaaagt gctgggatta | 900 |
| caggcgtgat ccaccacacc tggcccttgc aatcttctac tttaaggtttt gcagagataa | 960 |
| accaataaat ccacaccgta catctgcaat atgaattcaa gaaaggaaat agtaccttca | 1020 |
| atacttaaaa atagtcttcc acaaaaaata ctttatttct gatctataca aattttcaga | 1080 |
| aggttatttt ctttatcatt gctaaactga tgacttacta tgggatgggg tccagtccca | 1140 |
| tgaccttggg gtacaattgt aaacctagag ttttatcaac tttggtgaac agttttggca | 1200 |
| taatagtcaa tttctacttc tggaagtcat ctcattccac tgttggtatt atataattca | 1260 |
| aggagaatat gataaaacac tgccctcttg tggtgcattg aaagaagaga tgagaaatga | 1320 |
| tgaaaaggtt gcctgaaaaa tgggagacag cctcttactt gccaagaaaa tgaagggatt | 1380 |
| ggaccgagct ggaaaacctc ctttaccaga tgctgactgg cactggtggt ttttgctctc | 1440 |
| gacagtatcc acaatagctg acggctgggt gtttcagttt gaaaatattt tgttgccttc | 1500 |
| atcttcactg caattttgtg taaatttctc aaagatctga attaaataaa taaaattcat | 1560 |
| ttctacagac ccacaaaaaa aaaaa | 1585 |

<210> SEQ ID NO 52
<211> LENGTH: 6807
<212> TYPE: DNA
<213> ORGANISM: Homo sapiens

<400> SEQUENCE: 52

| | |
|---|---|
| tctaactcta tagtaggcat gttatgttgt tcttattacc ctgattgaat gtgtgatgtg | 60 |
| aactgacttt aagtaatcag gattgaattc cattagcatt tgctaccaag taggaaaaaa | 120 |
| aatgtacatg gcagtgtttt agttggcaat ataatctttg aatttcttga ttttccaggg | 180 |
| tattagctgt attatccatt ttttttactg ttatttaatt gaaaccatag actaagaata | 240 |
| agaagcatca tactataact gaacacaatg tgtattcata gtatactgat ttaatttcta | 300 |
| agtgtaagtg aattaatcat ctggattttt tattctttttc agataggctt aacaaatgga | 360 |
| gctttctgta tataaatgtg gagattagag ttaatctccc caatcacata atttgttttg | 420 |
| tgtgaaaaag gaataaattg ttccatgctg gtggaaagat agagattgtt tttagaggtt | 480 |
| ggttgttgtg ttttaggatt ctgtccattt tctttttaaag ttataaacac gtacttgtgc | 540 |
| gaattatttt tttaaagtga tttgccattt ttgaaagcgt atttaatgat agaatactat | 600 |
| cgagccaaca tgtactgaca tggaaagatg tcaaagatat gttaagtgta aaatgcaagt | 660 |

```
ggcaaaacac tatgtatagt ctgagccaga tcaaagtatg tatgttttta atatgcatag    720
aacaaaagat ttggaaagat atacaccaaa ctgttaaatg tggtttctct tcggggaggg    780
ggggattggg ggaggggccc cagaggggtt ttataggggc cttttcactt tctactttt     840 tcattttgtt ctgttcgaat ttttataag tatgtattac ttttgtaatc agaattttta    900
gaaagtattt tgctgattta aaggcttagg catgttcaaa cgcctgcaaa actacttatc    960
actcagcttt agttttcta atccaagaag gcagggcagt taaccttttt ggtgccaatg    1020
tgaaatgtaa atgattttat gttttcctg ctttgtggat gaaaaatatt tctgagtggt    1080
agttttttga caggtagacc atgtcttatc ttgtttcaaa ataagtatt ctgattttgt     1140 aaaatgaaat ataaaatatg tctcagatct tccaattaat tagtaaggat tcatccttaa    1200
tccttgctag tttaagcctg cctaagtcac tttactaaaa gatctttgtt aactcagtat    1260
tttaaacatc tgtcagctta tgtaggtaaa agtagaagca tgtttgtaca ctgcttgtag    1320
ttatagtgac agcttccat gttgagattc tcatatcatc ttgtatctta aagtttcatg     1380 tgagtttta ccgttaggat gattaagatg tatataggac aaaatgttaa gtcttcctc      1440 tacctacatt tgttttcttg gctagtaata gtagtagata cttctgaaat aaatgttctc    1500
tcaagatcct taaaacctct tggaaattat aaaaatattg gcaagaaaag aagaatagtt    1560
gtttaaatat tttttaaaaa acacttgaat aagaatcagt agggtataaa ctagaagttt    1620
aaaaatgctt catagaacgt ccagggttta cattacaaga ttctcacaac aaacctattg    1680
tagaggtgag taaggcatgt tactacagag gaaagtttga gagtaaaact gtaaaaaatt    1740 atattttgt tgtactttct aagagaaaga gtattgttat gttctcctaa cttctgttga     1800
ttactacttt aagtgatatt catttaaaac attgcaaatt tattttattt atttaattt     1860 cttttgaga tggagtcttg cttgtcaccc aggctggagt gcagtggagt gatctctgct    1920
cactgcaacc tccgccttct gggttcaagc gattctcgtg cctcagcttc ctgagtagct    1980
ggaattacag gcaggtgcca ccatgcccga ctaattttt tttattttta gtagagacgg     2040
ggtttcacca tgttggccag gctggtatca aactcctgac ctcaagagat ccactcgcct    2100 tgcccctccca aagtgctggg attacaggct tgagccacca cgcccggcta aaacattgca    2160
aatttaaatg agagttttaa aaattaaata atgactgccc tgtttctgtt ttagtatgta    2220
aatcctcagt tcttcacctt tgcactgtct gccactagt ttggttatat agtcattaac     2280
ttgaatttgg tctgtatagt ctagacttta aatttaaagt tttctacaag gggagaaaag    2340
tgttaaaatt tttaaaatat gttttccagg acacttcact tccaagtcag gtaggtagtt    2400
caatctagtt gttagccaag gactcaagga ctgaattgtt ttaacataag gcttttcctg    2460
ttctgggagc cgcacttcat taaaattctt ctaaaacttg tatgtttaga gttaagcaag    2520 acttttttc ttcctctcca tgagttgtga aatttaatgc acaacgctga tgtggctaac     2580
aagtttattt taagaattgt ttagaaatgc tgttgcttca ggttcttaaa atcactcagc    2640
actccaactt ctaatcaaat ttttggagac ttaacagcat ttgtctgtgt ttgaactata    2700
aaaagcaccg gatctttcc atctaattcc gcaaaattg atcatttgca aagtcaaaac       2760
tatagccata tccaaatctt ttccccctcc caagagttct cagtgtctac atgtagacta    2820
ttccttttct gtataaagtt cactctagga tttcaagtca ccacttattt tacatttag     2880 tcatgcaaag attcaagtag ttttgcaata agtacttatc tttatttgta ataatttagt    2940
ctgctgatca aaagcattgt cttaattttt gagaactggt tttagcattt acaaactaaa    3000
ttccagttaa ttaattaata gctttatatt gcctttcctg ctacatttgg ttttttcccc    3060
```

```
tgtcccttttg attacgggct aaggtagggt agagtgggtg tagtgagtgt atataatgtg    3120
atttggccct gtgtattatg atatttttgtt attttttgttg ttatattatt tacatttcag    3180
tagttgtttt ttgtgtttcc attttagtgg ataaaatttg tattttgaac tatgaatgga    3240
gactaccgcc ccagcattag tttcacatga atacccttt aaacccgaat cattgtttta    3300
tttcctgatt acacaggtgt tgaatgggga aaggggctag tatatcagta ggatatacta    3360
tgggatgtat atatatcatt gctgttagag aaatgaaata aaatgggct gggctcagtg    3420
gctcacgcct gtaatcccag cactttggga ggctgaggca ggtggatcac gaggtcagga    3480
gatcgagacc atcctggcta acacggtgaa accccgtctc tactaaaaaa cagaaaatta    3540
gccgggcgtg gtggcgggcg cctgtagtcc cagctactcg ggaggctgag gcaggagaat    3600
ggtgtgaacc cgggaggcag agcttgcagt gagccgagat ctcgccactg cactccagcc    3660
tgggcaacag agcaagactc tgtctcaaaa aaaaaaaaa aagaaataag aaaatgggaa    3720
gcaatatttg acatagttct ttttagtcaa atctacttgt taaaaaaagg gtagcagttt    3780
attcatctgt gaaaggaaaa taatacttat cttacaaggt tgcaagagct caaggagacc    3840
atgtatgtaa agttcctgct gtaaatatga actcccatcc taatacccct ttacctctct    3900
gtgggtttgt cttgacctgg aaatttgggc taaaacttag aaaaaattct tacatgataa    3960
ctcagtgatg cttactcata gttttttggtg tttctcatag ataagatata aatcagctgg    4020
gcgcggtggc tcatgcctgt aatcccagca ctttgggagg ccgaggcggg cagatcacct    4080
gaggtcggga ggtcgagacc agcctgacca acatggagaa accccgtctc tactaaaaat    4140
acaaaattag ctgggcgtgg tggctcatgc ctgtaatccc agctacttgg gaggctgagg    4200
caggagaatc gcttgaaccc aggaggcgga ggttgtggtg agcgaagatc gtgccattgc    4260
actccagcct gggcaacaag agcaaaactc tgtctcaaaa aaaaaaaag atataaatca    4320
caataaataa ataggtcaat acaaatgtta gccaggcgtg gtggcacatg cccatagtcg    4380
cagctactct ggaggcagag gcaggaggat cacttgagcc catgaatttg aggcagcagt    4440
gagctatgat tgtgccactg tactccagtc tgggtgacag agtgagaccc catctctaaa    4500
taaataggtc aaacccttaa aaatatttaa attcttaaaa aattgaaaag attattcttc    4560
tcaaatttag ttgagctttc taagagaagc aattggcttt ttcccacttc aataatcatt    4620
ttcagtttga ctcatacagt taacacaatg tgaatttctt cctcagcata acagagttat    4680
agaatgacag ggctggaagt gaccttagag agtatccagt tctttcattt tacaggtgag    4740
gcaactgaga ctcaaaggtg atgtaatttg tgcaaagatt atagctaatt agtagcagag    4800
ccctgactgg gacatagttt gaaggtgaaa aacttcacca agctacccttt cttgaaaggt    4860
ccaaatgttt atgttttcaa ctactctttc cactgtacca taactttcac tacatattaa    4920
atgacacttt ataactaata taataggaca atcatcaatg catatatagc cagcccttca    4980
tatctgtggg ttttgcatcc atggattcaa ccaaggagga attgaaaaca ctgagaaaaa    5040
aaaaaaagac cacacaataa aaaaaaaaaa tacaaaataa tacaaagaaa aagccaaaat    5100
tgtcatactg ttgttaagca acagtataac aactatttac atagcattaa ggttggtgca    5160
aaaatgcaaa aaaaaaaaaa gcaattattt ttaaaccaac ctaatatatt gtattaggta    5220
ttaaagtcat ctggacatga attaaagtat atgatgccag cctggacaaa aggcaaaacc    5280
ctgtctctac aaaaaataca aaattagct gggcatggtg gtgtgtgcct gtagtcctgg    5340
ctactccgga gcctgaggtg ggaggatcgc ttgagtctgg gaggcagagg ctgcattgag    5400
```

```
ctatgatcat ggcactgcat tccagcctgg gtgacagtgc aagaccttgt ctcagaataa      5460
ataaagtatg tgatgaagat gtgcatacat tatatgcaaa tactgttttt tttttttta       5520 atttaaacag tctcactgtg ttcccagga tggagtgcaa tggcacaatc ttggctcatg       5580
gcaaactctg cctcgcaagc agctgggact acaggcatgc ccacggtgc ccagttaatt      5640 tttttttgtat tcttagtaga gacagggttt caccatgttg gccaggctag tcttgaattt     5700
ctgacctcaa gtgattcatc tcccaaagtg ctgggattac aggcgtgagc caccacggcc     5760
ggctaatttt tgtattttt agtagtgact ggtttcgcgg tgttgaccag gctggtctcg      5820
aactcctgat ctcaggtgat ctgcctgcct cggcctcaca aagtgctggg attacaggtg      5880
tgaaccactg ctcccggcct tgtgtgattt tatctaaggg acttaagcgt cctcaggtcc      5940
tagggggtcg tgaaaccaaa accccaggga tagcaaggga caattgtatc ttcaaagtag      6000
acaaatggcg ccgggcacgg tggctcacgc ctgtaatccc agcagtttcc gaggctgagg      6060
caggcggctc acctgaggtc aggagttgga gaccagcctg ccaacatgc tgaaaccctg       6120 tctgtacaaa aatacaaaaa tagctgggca tggtggcgca tgcctgtagt cccagctact      6180
agagcgactg aggcaggaga attgcttgaa cctgggaggc ggaggttgca gggagccaag      6240
atggcgccac cgcactccag cctaggtgat agagtgagac tccctctcaa aaacaaaaca      6300
aaacaaaaaa attagacaaa tgctacatta atgtttgggt ggtcagattc tactttgaat      6360
ctgaagtttg cagatatgcc tatagatttt tggagtttac cactttctta ttctgtatca     6420
ttaatgtaat attttaaatt actatatatg ttaccatttt tctggattta gtaagaaatt     6480
tgcagttttg gttgatgta acaagggttt taatgtaatt tatgttagat tttgcatttt      6540
tttcattact gttatatttt aacctgactg actgatctaa ttgtattagt attgtgaata     6600
atcatgtgaa atgttttgag acagagtact atatttgtga atataatttt atggtttttt    6660
tcacttagaa cctttctgtg tggaaaacta agaaaattgc tttctgctgt ataatctggc     6720
attcattgta gattaaagct tattttctg tgaataaaac gtattcaata aaatactatt      6780
ctttaaaatt atatcataaa aaaaaaa                                         6807

<210> SEQ ID NO 53
<211> LENGTH: 429
<212> TYPE: DNA
<213> ORGANISM: Homo sapiens

<400> SEQUENCE: 53
gccaaaagaa agtctaatta tatacagaga taaagctaaa cgtaattatt atttaaatga       60
aagctatttt tttaaatgaa ttgaaatttt tcatgatgct actaatttgc cactaaatac      120
tgcaaatggt caccctgaat ctcttctgac attggatgtt atttgctat attcttataa      180 tttttaaatga gggcacagtg aaatgaaaat tttatactct atgtttctgt ttatttttaa     240
atccttaaca gcaaaatatt tgcctttaat ttcttttta tatatactct cagagaattc       300 ctcttaatttt ttaaagatgc tggtgataat aaaattcatt agaaaatttc ctcattgtgg    360
aatgagcatt ctcttgtttt aatgttggtg tcagaaaata aatatgaaac attaagtcca      420
aaaaaaaaa                                                             429

<210> SEQ ID NO 54
<211> LENGTH: 3228
<212> TYPE: DNA
<213> ORGANISM: Homo sapiens

<400> SEQUENCE: 54
```

```
attaaaatcg tactcataat cagctctgca tacatctgaa gaacaaaaac atcaacgtct    60
tttgtccagc ctcttttct tctgctgttc cacctttcta acatacaat aaagtcatgg    120 gataaaaata atcgatgtat gttacgggcg cttaaccat cagctgcctc tcgaatggaa    180
gaacagtggt aatggattaa catcctattt tgttgtacta aagtgacaaa tcggaataat    240
ataattggta tggccattag gttcagtcct tgaagataag aaacttgttc tctgtttgtt    300
gtcttatttg tggtggcact cgtttaatgg attaactgag gttgctcaat gttcagtttc    360
ttttccagaa atacaatgct aggtgttttg aaataaaact tatatagcaa ttgtttaaag    420
ttatcaattg tatataaaat cacagtagcc tgctaaatca ttgtatgtgt ctgtagtatt    480
ctattcccag aaactatttg accatgataa ttcagtttat attcaccaca tgaaagaaaa    540
atgggtaaca gaagaacct taaacaggt taatttggat tgtaacgttc agtgaaagaa    600
atttcaaccc ttcatagcca gcgaagaaat ttgccttgga agccaagtca gtaccagctt    660
acctatttga ttcagttgct gttttctcac tctctatatc catttgaaat tgatttattt    720
tagatgttgt atacttacgt taggcttct gttaatagtg gttttctcc tgttgacaga    780 gccaccggat tatgacacag gatgaggaag attaaggata atcaattgac taatttcatt    840
tagaatatta tcaaacattt caactaggta tcagaaaaag gctttctttc ataagactat    900
tttaaataga aattatttca acaattaaag taatgttgac catcccctc tcagctgaat    960 aaagaaaaat ttagttcaat ttattgcaat ttaattacaa tactaccttc acaacatttt    1020
catgtgtttt aaataaatat tttttaattg gctaaaggac attcaagcaa agaaatgctt    1080
tctttactta aaatgtctat ctcatttgct gccttttcac taagcctta ctttgttaat    1140 aaaagtgtcc attgtgtgat gttttgatt ttacagtttg ctaaatctta ttttcttgga    1200 gttgctttt ggtaacagcc ccattgctac tccccatttt attgttttac atcaatgcat    1260
gcttcgttgt gatccctcaa gatgtaacac ttggtatgct cggttgagga tatgaaaaaa    1320
tacttccgaa accaggaatt caatgtatgt ttgttttata ctgtttgata agaaaagtag    1380
gtccagcctt aagcagcaca gatgcgctgg tagatgcata gtcaggaact ttttttattt    1440
cttttaggtc tagggacagg agtgaataga aagggaggag agctctatta tgttctatac    1500
acagattagg agatgacctt actgggtaca cccctctaac cagtgcttac aggttaatgc    1560
atgttaatga atatttttgc agttgtaaag cataacaatt acaactacac atctatttct    1620
aaagaataaa acaggaccat atttatttac ttctgtcaac tatagaaaga aagaccttca    1680
gctgtatttc cacagatttc tcccaaggaa aaggctaata ttagtcacta ctgttatcac    1740
atccctttgt ataagtttta aaagagatg gagggagatc ttcatttctt tgaggagatc    1800
agtattgtaa cgtatgtgaa tagatgataa caattaatat tactaaaagt cccacatgag    1860
agtcctgacg ccctctccat gccccacagt aatgtggctt ctttcatggg tttttttttc    1920 ttcttttag ctgatctcat cctaagcatg ctttattttt ccttgaaagc taggtattta    1980
tcaactgcag atgttattga agaaaataa aattcagtct caagagtaaa ccctgtgtct    2040
tgtgtctgta gttcaaaagt cagaaatgat tctaatttaa acaaaaagat actaaatata    2100
cagaagttaa attcgaacta gccacagaat catttgtttt tatgtcagaa tttgcaaaga    2160
gtggagtgga caaagctctg tatggaagac tgaacaactg taaatagatg atatccaaac    2220
ttaatttggc taggacttca atttaaaaa tcagtgtacc taggcagtgc acagcacgaa    2280
ataagtggcc cttgcagctt ccccgtttaa cccactgtgc tatagttgcg ggtggaacag    2340
```

| | |
|---|---|
| tcaacctttc tagtagttta tgatattgcc ctctttgtat tcccattttc tacagttttt | 2400 |
| tccgcagact tctttctgca aattattcag cctccaaatg caaatgaatg atataaaaat | 2460 |
| aagtagggaa catggcagag agtggtgctt cccagcctca caatgtggga atttgacata | 2520 |
| ggatgagagt cagagtatag gtttaaaaga taaaatcttt agttaataat tttgtattta | 2580 |
| tttattctag atgtatgtat ctgaggaaag aaatctggta ttttgctttt ccaataaagg | 2640 |
| ggatcaaagt aatggttttt ctctcagttc tctaagctgg tctatgttat agctctagca | 2700 |
| gtatggaaat gtgctttaaa atatgcttac cttttgaatg atcatggcta tatgttgttg | 2760 |
| agatatttga aacttacctt gttttcactt gtgcactgtg aatgaacttt gtattatttt | 2820 |
| tttaaaacct tcacattacg tgtagatatt attgcaactt atattttgcc tgagcttgat | 2880 |
| caaaggtcat ttgtgtagat gagtaattaa aaaatattta aatcacatta taattctatt | 2940 |
| attggagagc atcttttaaa ttttttttctg ttttaacgag ggaaagagaa acctgtatac | 3000 |
| ctagggtcat tatttgaccc catagtataa ccagattcat ggtctaacaa gctctcagtg | 3060 |
| tggcttttct ctgaatgctt gaatttcaca tgccttgcat ttcacagttg tactccatgg | 3120 |
| tcaaccggtg cttttttttca catcgtggta cttgtcaaaa catttttgtta ttttccttgg | 3180 |
| taaaatatat aaaaaaggtt ttctaatttc aaaaaaaaaa aaaaaaaa | 3228 |

<210> SEQ ID NO 55
<211> LENGTH: 4173
<212> TYPE: DNA
<213> ORGANISM: Homo sapiens

<400> SEQUENCE: 55

| | |
|---|---|
| aagtagaaga ttgagatgtg ttcacaatgg ataggcacag gaaaccagtt aggtctcaat | 60 |
| acctgaagct atcgtaaaat taagaaagga taaagttggt aaacctttta tatttagtat | 120 |
| cttttttattc agctcatgga cttctgccag cataatactt gctttggaaa acccagataa | 180 |
| aggttcatgc aaactttatt ttgtgtttag gaactactga ggatcagagt aatccaagca | 240 |
| aatgtgaatc atttttacctt tgacaaaggt aaatcagact atgaagtttt ttttatacag | 300 |
| gatgatgact atggaaagag tactcttgtt tccttatatt atggaggcag gagtttcgtt | 360 |
| ttcaaaattg ttacaaattg tagaagccac ggtgttctgt gatataagtg tgtgtttttc | 420 |
| ataaagcagg cagaactcat ctaggtaaat tacagttcct aggtataatt cacattgtat | 480 |
| tcagagttga tggttgtaca tataagtgat tgctggtttt agttgcaact ttgtataaaa | 540 |
| gggactgaga aatttataaa ctttttttctt actgtctttt ttctaaagta aaaacaaaga | 600 |
| aattatgtgc cagatttatg catattattt tatgttgcat agaataaaat ttttaatctt | 660 |
| taattttaca tttcctaaat atattttaag acgaaacatt tgttctatag cttttccctt | 720 |
| tttttaagta aggaattttta ttttttttctg aattattttc tctcgtgagt atattgatcc | 780 |
| agaaagaaaa cttgtattat gtgtgttttta aaatgagaaa tctaaaaaac gaaagtctc | 840 |
| caaagtctct ggaatttgaa acactttgca taacgtataa aagcctgttt aagagacagc | 900 |
| caactatggc ctgtggatca aatccagcct gctgcctgct ttttatggcc tgtgagctag | 960 |
| gaattgtgtt tataatttta aatgtttttt tttaaagact tttatgatac ttgaaaatta | 1020 |
| acatgaatat ttagtgttca taaataaagt ttgttgaaac acaaccaaga tcattctttt | 1080 |
| acttgtctat ggctgctttt ctgtggcaga gtagctgcca cagaaactat agcccacaaa | 1140 |
| gcctgatatt tactgtctgt ctgtttatgg aaaaaattta tcaacccatg gtctatagta | 1200 |
| tagtgtgata tgactactgt tccaatgtat tgaagtgttg ggatagtttt ttcaaatgtt | 1260 |

```
ttcagatgtt cttgttttag aatcattgtc acctttaaga ggaaaaaggt catcactaga    1320
taatctaaac aaattgttgc ttctcagtgt tagcaaggaa aataatctag tttcaaatta    1380
cattgcagta taatgaaaaa gatccatata ctgtggaatg atattctttt aaaattattt    1440
gctatggctt ggtaaaaatg tactttttcc agtagcacat atcacaagaa cctcactgta    1500
gttgaaagcc atctttcttt agtatttgtt tatcctttta ggagagtcaa gcaaaggttt    1560
tcaccacctg tttgagcaga ataattctca tcagttcaca gatataggat aactcaattt    1620
atatgcactt tatgcgttat gcaaaatatt tagaaattgt agattctaga tctccagaaa    1680
gactttgaag actttgatgt cacaaaaaga tgacttgtta tatgctgagc ttgacaaagg    1740
taggaatggg agagaaaaat agtagcttat gaggaaatat gaggctttaa atatataaag    1800
ttggatattt taaaataact tttccctgtg ggagcttctc actctgggtg cagacaggac    1860
agtgttggcc attggtgaaa tagataggat gggtttgagg ccagagcagt ctgggagtag    1920
ggggaaagag aaggaggtgt gctagtgtct atcacaggct ttctcaatta ggtttgcagg    1980
agaaaaagcc ctaagtccct gtgtcatcta gaatggtact aattatgtac agtccctagg    2040
agaatggaga aaatcataac tcaaatcatc gactcaattc tgttctcttc agatgagctc    2100
agagagcaca taggagtgtt tgtaatgagg ggtatgtaat gattgagata gaggaatgag    2160
ttacataaac atctcgggac aaatgcagca tagaaaacat ctttgtagtt accctgcggg    2220
gaaatttcct ctgagttctt ttaacattaa ctacccgtat tattttatac ttaacattca    2280
tatcatacct tcccaaatat attgggaagt tcagtgttaa gtacgtttct caagtactta    2340
acaacttaat atagggagga aaggtgtaaa cagtgaaaaa agagcaaaac tattttatgg    2400
taattttatg gtagtatcag cttgtatttg gttctctgtt tctaaaataa tgtaattttt    2460
aatattttaa ataataggat aacctggttt ccaagccttt ttttcccccg acatccagaa    2520
tacacactgg atccaagcct ttcttaaaca tcagtacatg tggaagactg gcatgccata    2580
taccaaatgc cattcagctg taacagtata cacagatttt ctcttataaa gaataagaac    2640
atcataacca atgaccactc atataaagtc ttatttgtgt gtgtgtgtgt gtgtgtgtgc    2700
acgtgtgtgt gttagagtct cattatattg ctcaggctgg agggcatggt gtgatcttgg    2760
ctcactgcag ccttgacctc ctgggctcaa gtgatccttc cgagtcgttg ggactacagt    2820
aggtgaacac caccatgcct ggctaatttt tgtatttttt ttttaatcaa gatgggatct    2880
tgctatgttg cccaggctgg tctcaaactc ctggcatcaa gcgttcctcc ttccttggcc    2940
tccttaagtg ctgggattat aggtgtgagc caccatgctt gaccataaag ccttactatt    3000
tcttttggag acacagtctt gctctgtcca agctggaatg cagtgatgtg atcatggctc    3060
actgcagcct tgaactccca ggcttaagag atcctcccat ctcagcctcc tgagtagctg    3120
ggattatagg tgcagaccat caagccttgc tattattttt tagactttc ttaatttcat    3180 ccaacaaagt agttgctgta ggagctgagt gttagaagga aagatgctga agaaatgaaa    3240
tcaagcaggg tgtatactgt catgaatagg catacagtag tttttatact tttgttcttt    3300
ggagtaccaa tgttaggttt tacaaaagta atttgatgag gggaaggagg gttgtgtatt    3360
tattttactt tctgatgttt gcttaaataa tactgtgtac gtattcagct tgctgtaatt    3420
ctgtaattac gctattgcgt ttggctaact ccttttttgga aatgtctttt tttttgtaca    3480
aggcatgtgt tagtttttac taattgctct gaatgtgtat atttagattt ctgaattgaa    3540
aaaaaatagc gtacaataag tagatttaaa gtaattagaa cactttattg atttttctga    3600
```

```
tgttttctgt atctaaaatt tatcaccacc aggttgtgct aaaacagcag gaagttttta    3660
tattgtgagt gacagtaccc attatttctc ttaattttac taacatttac tataagaata    3720
ttctctcgct cttttctcca ctcacagcca ttctccctcc ttctcttcat aacatcaagc    3780
tgtcacagac aaatctgaaa atgttacaag cacagactat gttgtatgtt ttgaaatttt    3840
agaacagtaa tgttcttttt aaaattgaac ttctgcagag taagaaaatg aatacattta    3900
ttactttaaa tttgtaaaat tttccaaagt aaaaccatac aaagctagtg tcagtctctc    3960
tcattgttca caaataaagg acttttgtta attgattaaa tcacttacta tattcgatat    4020
gaaatatata aaacatacaa ccattatcta atacatttca gaatgtttca ctggttacag    4080
gagccagtaa ataaagttga ctctaaacag gaattttaaa taaactaaac attttttcat    4140
caccaagcat catttaaaaa aaaaaaaaaa aaa                                 4173
```

METHOD FOR ASSAYING MICRORNA, CANCER THERAPEUTIC AGENT, AND MEDICAL COMPOSITION CONTAINING SAME FOR CANCER THERAPY

CROSS REFERENCE

This is a continuation application of U.S. Ser. No. 15/976,460 filed May 10, 2018, which is a divisional application of U.S. Ser. No. 14/767,372 filed Nov. 3, 2015, now U.S. Pat. No. 9,994,843 issued Jun. 12, 2018, which is a U.S. National Stage Entry of PCT/JP2014/053594 filed Feb. 17, 2014, which claims priority from JP Patent Application No. 2013-027399 filed Feb. 15, 2013, the contents of all of which are incorporated herein by reference.

TECHNICAL FIELD

The present invention firstly relates to an assay of biospecimens and, more particularly, to an assay of a microRNA in a tumor tissue for the differentiation of malignancy or the like of cancer. The invention also relates to an anticancer agent and, more particularly, to an anticancer agent and an anticancer pharmaceutical composition pertaining to a specific microRNA.

BACKGROUND ART

Cancer has become the top cause of death of Japanese for many years, accounting for about one-third of total deaths estimated in 2007. In the world, about 13% of deaths in 2005 were attributed to cancer, previously reported by the World Health Organization (WHO). Deaths by cancer are increasing continuously, and it is estimated that in 2030, 11,400,000 people worldwide will die due to cancer in a year.

Meanwhile, the progress in diagnosis and treatment of cancer is remarkable. In particular, when the relevant treatment can be initiated at a very early stage of the cancer, five-year survival rate quite often exceeds 90%. In addition, it is a current common sense that particularly in the case of elderly, even if their cancer is not completely cured, they can live out their lives if progress or metastasis of cancer can be suppressed.

The human genomic project, completed in 2003, and similar projects have accelerated gene-level or protein-molecule-level research of cancer and application of the results to diagnosis and treatment of cancer. As a result, various techniques supporting medical science and biology have been further developed, and methods in relation to early stage diagnosis and treatment of cancer have rapidly progressed.

Long ago, cancer notification was almost equivalent to "a death sentence," and thus notification of cancer to the patient was considered taboo. However, Japan's "Cancer Control Act" enforced in 2007 requests cancer patients and other interested parties to be actively involved in cancer control.

Under such circumstances, continuous efforts are currently made toward development of cancer therapeutic and diagnostic methods from a wider variety of aspects.

PRIOR ART DOCUMENTS

Non-Patent Documents

Non-Patent Document 1: Itoh, K. et al., Biochem. Bioph. Res Co. 236, 313-322 (1997)
Non-Patent Document 2: Uruno, A. & Motohashi, H., Nitric Oxide-Biol. Ch. 25, 153-160 (2011)
Non-Patent Document 3: Singh, A. et al., Plos. Med. 3, 1865-1876 (2006)
Non-Patent Document 4: Thimmulappa, R, K. et al., Cancer Research, 62, 5196-5203 (2002)
Non-Patent Document 5: Mituishi, Y. et al., Cancer Cell 22, 66-79 (2012)
Non-Patent Document 6: Kim, Y. R. et al., J. Pathol. 220, 446-451 (2010)
Non-Patent Document 7: Taguchi, K., Motohashi, H. & Yamamoto, Genes Cells 16, 123-140 (2011)
Non-Patent Document 8: Hammerman, P. S. et al., Neoplasia 13, 864-873 (2011)
Non-Patent Document 9: Shibata, T. et al., Neoplasia 13, 864-873 (2011)
Non-Patent Document 10: Inami, Y. et al., J. Cell Biol. 193, 275-284 (2011)
Non-Patent Document 11: Komatsu, M. et al., Nat. Cell Biol. 12, 213-U217 (2010)
Non-Patent Document 12: Taguchi, K. et al., P. Natl. Acad. Sci. USA 109, 13561-13566 (2012)
Non-Patent Document 13: Lau, A. et al., Mol. Cell Biol. 30, 3275-3285 (2010)
Non-Patent Document 14: Jiang, T. et al., Cancer Research 70, 5486-5496 (2010)
Non-Patent Document 15: Shibata, T. et al., P. Natl. Acad. Sci. USA 105, 13568-13573 (2008)
Non-Patent Document 16: Soils, L. M. et al., Clin. Cancer Res. 16, 3743-3753 (2010)
Non-Patent Document 17: Ambros, V., Nature 431, 350-355 (2004)
Non-Patent Document 18: Zhao, Y. & Srivastava, D., Trends Biochem. Sci. 32, 189-197 (2007)
Non-Patent Document 19: Kong, Y. W., Ferland-McCollough, D., Jackson. T. J. & Bushell, M. Lancet, Oncol. 13, E249-E258 (2012)
Non-Patent Document 20: Lu, J. et al., Nature 435, 834-838 (2005)
Non-Patent Document 21: Miska, E. A., Curr Opin. Genet. Dev. 15, 563-568 (2005)
Non-Patent Document 22: Shivdasani, R. S., Blood 108, 3646-3653 (2006)
Non-Patent Document 23: Zhang, B. H., Pan, X. P., Cobb, G. P. & Anderson, T. A., Dev. Biol. 302, 1-12 (2007)
Non-Patent Document 24: Lewis, B. P., Burge, C. B. & Bartel, D. P., Cell 120, 15-20 (2005)
Non-Patent Document 25: Tsuruta, T. et al., Cancer Research 71, 6575-5778 (2011)
Non-Patent Document 26: Takeshita, F. et al., Mol. Ther. 18, 181-187 (2010)
Non-Patent Document 27: Liu, C. et al., Nat. Med. 17, 211-215 (2011)

SUMMARY OF THE INVENTION

Problems to Solve the Invention

Under the aforementioned circumstances involving cancer, the present inventors have focused on an NF-E2-related factor 2 (NRF2) in relation to cancer. Thus, an object of the present invention is to provide means for the diagnosis and treatment of cancer based on a new concept.

NRF2 is a transcriptional regulator for cytoprotection against cellular damage from chemotherapy and oxidative stress (Non-Patent Documents 1 and 2). Under physiological conditions, NRF2 is ubiquitinated by KEAP1 (cullin 3

(CUL3)-Kelch-like ECH-associated protein) ubiquitin E3 ligase complex and is constantly degraded in proteasome, whereby the cellular NRF2 protein concentration can be maintained at low level. Under cellular stress, KEAP1 is inactivated, and NRF2 is stabilized in the nucleus, leading to cell survival through transcriptional activation of target genes [in which NRF2 binds directly to the antioxidative response element (ARE) within the promoter in each target gene] (Non-Patent Documents 3 and 4). In addition to general response to cellular stress, it has been reported that NRF2 can also contribute to tumor cell growth via modulation of metabolism (Non-Patent Document 5). Gene mutations lead to gain-of-function for NRF2 or loss-of-function for KEAP1 in various types of human cancers, whereby NRF2 is activated, resulting in cancer cell survival and growth by the mediation of NRR2 (Non-Patent Documents 6 to 9). Moreover, excess accumulation of p62 protein (i.e., a substrate for protein degradation via autophagy) forms an aggregate, which stabilizes NRF2 through competitive interaction with KEAP1 in hepatocellular carcinoma (HCC) (Non-Patent Documents 10 to 13). Thus, it is though that NRF2 exhibits an oncogenic function in cancer cells, and a high level of NRF2 protein is associated with poor prognosis (Non-Patent Documents 14 to 16). Consequently, therapeutic inhibition of NRF2-mediated oncogenic pathways may be particularly effective for cancers having resistance to various therapies due to stabilized NRF2. The inventors have also conceived that malignancy of cancer, which can directly estimate the prognosis of a patient, can be differentiated by finding an index which reflects the extent of stabilization of NRF2.

The present inventors have focused on the role of microRNA (miRNA) with respect to NRF2. miRNA is an endogenous small non-coding RNA molecule which regulates gene expression through interfering with translation or stabilization of target transcripts via binding to the 3'-untranslated region (UTR) (Non-Patent Documents 17 and 18). Some miRNAs can negatively regulate an oncogene, and down-regulation of tumor-suppressive miRNAs leads to activation of oncogenic pathways (Non-Patent Documents 19 to 22). Importantly, one transcript can be targeted by a plurality of miRNAs, whereas one miRNA can target a plurality of transcripts (Non-Patent Documents 23 and 24). This suggests that down-regulation of multiple miRNAs, which target an oncogene, activates oncogenic pathways, and that administration of miRNA which can target multiple genes in relation to one oncogenic pathway may be effective in cancer therapy.

Thus, a specific object of the present invention is to find miRNAs which are strongly associated with stabilization of NRF2 in tumors, and to provide means for utilizing such miRNAs for the diagnosis and treatment of cancer.

Means for Solving the Problems

In order to attain the above object, the present inventors conducted screening of 470 miRNAs in a microRNA library by use of an ARE reporter system. More specifically, HeLa cells were transfected with each of the 470 miRNAs, and luciferase activity of each case was determined, to thereby calculate ARE activity. As a result, 8 miRNAs (hsa-miR-507, hsa-miR-634, hsa-miR-450a, hsa-miR-129-5p, hsa-miR-639, hsa-miR-337, hsa-miR-153, and hsa-miR-556), each exhibiting a large decrease in ARE activity as compared with a control miRNA, and 8 miRNAs (hsa-miR-26a, hsa-miR-17-3p, hsa-miR-190, hsa-miR-567, hsa-miR-125b, hsa-miR-125a, hsa-miR-432*, and hsa-miR-29), each exhibiting a large increase in ARE activity as compared with a control miRNA, were identified. The inventors have found that the NRF2 activation in the living body, in particular tumor cells, can be detected by use of the thus-identified microRNAs, whereby malignancy of a tumor, or prognosis of a cancer patient can be differentiated. The inventors have also found that a nucleic acid(s) including a sequence(s) of the microRNAs associated with decrease in ARE activity as mentioned above can be used as a cancer therapeutic agent.

Accordingly, the present invention provides the following.

In a first aspect of the present invention, there is provided a method for assaying microRNA, characterized by comprising quantitating one or more microRNAs selected from the group consisting of hsa-miR-507, hsa-miR-634, hsa-miR-450a, hsa-miR-129-5p, hsa-miR-639, hsa-miR-337, hsa-miR-153, and hsa-miR-556 in a human specimen, and differentiating malignancy of a tumor, NRF2 activation, or prognosis of a cancer patient on the basis of a decrease in the quantitated value(s) as an index (hereinafter, the method may also be referred to as the low value determination method of the present invention). Among the 8 microRNAs to be assayed in the low value determination method of the present invention, 4 microRNAs; i.e., hsa-miR-507, hsa-miR-634, hsa-miR-450a, and hsa-miR-129-5p, in particular, exhibit a low quantitation value in the case of a malignant tumor.

In a second aspect of the present invention, there is provided a method for assaying microRNA, characterized by comprising quantitating one or more microRNAs selected from the group consisting of hsa-miR-26a, hsa-miR-17-3p, hsa-miR-190, hsa-miR-567, hsa-miR-125b, hsa-miR-125a, hsa-miR-432*, and hsa-miR-29 in a human specimen, and differentiating malignancy of a tumor, NRF2 activation, or prognosis of a patient on the basis of an increase in the quantitated value(s) as an index (hereinafter, the method may also be referred to as the high value determination method of the present invention).

In the low value determination method and high value determination method of the present invention, one to three elements selected from the group consisting of NRF2 gene mutation, KEAP1 gene mutation, and p62 protein accumulation in the tumor are detected, and the elements are added to the index, whereby accuracy in differentiation can be enhanced.

In the low value determination method and high value determination method of the present invention, preferably, the sum of the indices each indicating the tendency of increasing malignancy of a tumor, activating NRF2, or aggravating prognosis of a cancer patient is employed as a score index, to thereby differentiate malignancy of the tumor, NRF2 activation, or prognosis of the patient.

In the low value determination method and high value determination method of the present invention, no particular limitation is imposed on the tumor (cancer) whose malignancy or the like is to be differentiated, so long as activation of NRF2 is problematic in malignancy or the like of the tumor (cancer). The method of the present invention may be applied to any malignant tumors including esophageal cancer, lung cancer, breast cancer, oral cancer, stomach cancer, colorectal cancer, liver cancer, uterine cancer, osteosarcoma, and skin cancer.

In a third aspect of the present invention, there is provided a cancer therapeutic agent consisting of a nucleic acid(s) including one or more microRNAs selected from the group consisting of hsa-miR-507, hsa-miR-634, hsa-miR-450a, hsa-miR-129-5p, hsa-miR-639, hsa-miR-337, hsa-miR-153, and hsa-miR-556 (hereinafter may also be referred to as the cancer therapeutic agent of the present invention). Among 8 microRNAs forming the cancer therapeutic agent of the present invention, 4 microRNAs; i.e., hsa-miR-507, hsa-miR-634, hsa-miR-450a, and hsa-miR-129-5p, in particular, exhibit excellent non-specific anticancer effect.

Moreover, the cancer therapeutic agent of the present invention is suitably used in combination with means for imparting cancer cells with stress.

In a fourth aspect of the present invention, there is provided a pharmaceutical composition for treatment of cancer, the composition comprising the cancer therapeutic agent of the present invention (hereinafter may also be referred to as the pharmaceutical composition of the present invention).

No particular limitation is imposed on the tumor (cancer) to which the cancer therapeutic agent or pharmaceutical composition of the present invention is administered, so long as activation of NRF2 is problematic in malignancy or the like of the tumor (cancer). The agent or composition of the present invention may be applied to any malignant tumors including esophageal cancer, lung cancer, breast cancer, oral cancer, stomach cancer, colorectal cancer, liver cancer, uterine cancer, osteosarcoma, and skin cancer. Particularly, a cancer to which the agent or composition of the present invention can be topically administered is preferred.

The sequences of the miRNAs of the present invention are listed in the following tables. Table 1-1 shows 8 miRNAs to be assayed in the low value determination method of the present invention (hereinafter may be referred to as low-value miRNAs), and SEQ ID NOs of 1 to 8 are assigned to them from the top of Table 1-1. Table 1-2 shows 8 miRNAs to be assayed in the high value determination method of the present invention (hereinafter may be referred to as high-value miRNAs), and SEQ ID NOs: 9 to 16 are assigned to them from the top of Table 1-2.

TABLE 1-1

| miRNA | mature sequence |
| --- | --- |
| hsa-miR-507 | UUUUGCACCUUUUGGAGUGAA |
| hsa-miR-634 | AACCAGCACCCCAACUUUGGAC |
| hsa-miR-450a | UUUUGCGAUGUGUUCCUAAUAU |
| hsa-miR-129-5p | CUUUUUGCGGUCUGGGCUUGC |
| hsa-miR-639 | AUCGCUGCGGUUGCGAGCGCUGU |
| hsa-miR-337 | GAACGGCUUCAUACAGGAGUU |
| hsa-miR-153 | UUGCAUAGUCACAAAAGUGAUC |
| hsa-miR-556 | GAUGAGCUCAUUGUAAUAUGAG |

TABLE 1-2

| miRNA | mature sequence |
| --- | --- |
| hsa-miR-26a | UUCAAGUAAUCCAGGAUAGGC |
| hsa-miR-17-3p | ACUGCAGUGAAGGCACUUGU |
| hsa-miR-190 | UGAUAUGUUUGAUAUAUUAGGU |
| hsa-miR-567 | AGUAUGUUCUUCCAGGACAGAAC |
| hsa-miR-125b | UCCCUGAGACCCUAACUUGUGA |

TABLE 1-2-continued

| miRNA | mature sequence |
| --- | --- |
| hsa-miR-125a | UCCCUGAGACCCUUUAACCUGUG |
| hsa-miR-432* | CUGGAUGGCUCCUCCAUGUCU |
| hsa-miR-297 | AUGUAUGUGUGCAUGUGCAUG |

Effects of the Invention

The present invention provides an assay method which enables differentiation of NRF2 activation through determining a specific miRNA, as well as malignancy of a tumor and prognosis of a cancer patient. The invention also provides a cancer therapeutic agent which exhibits such an antitumor effect that activation and stabilization of NRF2 in a target tumor are inhibited by use of a nucleic acid including a specific miRNA, and a pharmaceutical composition for the treatment of cancer. In an effective manner, the cancer therapeutic agent and pharmaceutical composition of the present invention are employed with "stress to cancer cells." The stress is provided by various cancer treatment and examination procedures, such as cancer chemotherapy, cancer radiotherapy, surgery, and biopsy.

BRIEF DESCRIPTION OF THE DRAWINGS

FIG. 1 Test results of an ARE reporter system employing siRNA.

FIG. 2-1 Screening results of miRNAs which enable down-regulation of transcriptional activity of NRF2.

FIG. 2-2 Expression analysis results of NRF2-targeted gene.

FIG. 3 Results of confirmation of NRF2 as a direct target of 4 candidate miRNAs.

FIG. 4 Results of Western blotting regarding expression of NRF2 in miRNA-transfected cells.

FIG. 5-1 Relationship between clinical significance and down-regulation of miRNA in a primary tumor specimen derived from esophageal cancer (esophageal squamous cell carcinoma: ESCC).

FIG. 5-2 Results of mutation analysis of NRF2 and KEAP1 gene in a primary tumor specimen derived from esophageal cancer (esophageal squamous cell carcinoma: ESCC).

FIG. 6 Results of identification of a transcription target gene of NRF2 as a target of hsa-miR-507.

FIG. 7 Graphs showing expression analysis of 4 miRNAs, and the effect of transfection with hsa-miR-507 on survival of cells A549 under stress induced by cisplatin treatment.

FIG. 8 In vivo tumor inhibitory effects of hsa-miR-507.

FIG. 9 In vitro studies of apoptosis-inducing effect of hsa-miR-634 on tumor cells.

FIG. 10 In vitro tumor inhibitory effect of hsa-miR-634 on esophageal cancer cells KYSE170.

FIG. 11 In vivo tumor inhibitory effect of hsa-miR-634 on esophageal cancer cells KYSE170.

FIG. 12-1 Effects of inhibiting expression of target gene XIAP (X-linked inhibitor of apoptosis protein), through introduction of hsa-miR-634 into osteosarcoma U20S cells, with reference to luciferase assay and Western blotting.

FIG. 12-2 Effects of inhibiting expression of target gene APIP (APAF1 interacting protein), through introduction of hsa-miR-634 into osteosarcoma U2OS cells, with reference to luciferase assay and Western blotting.

FIG. 12-3 Effects of inhibiting expression of target OPA1 (optic atrophy 1), through introduction of hsa-miR-634 into osteosarcoma U2OS cells, with reference to luciferase assay and Western blotting.

FIG. 12-4 Effects of inhibiting expression of target TFAM (transcription factor A, mitochondrial), through introduction of hsa-miR-634 into osteosarcoma U2OS cells, with reference to luciferase assay and Western blotting.

MODES FOR CARRYING OUT THE INVENTION

<Assay Method of the Present Invention>
(1) Low Value Determination Method of the Present Invention As described above, the low value determination method of the present invention is directed to a "microRNA assay method, characterized by comprising quantitating "a low-value miRNA(s)" in a human specimen, and differentiating malignancy of a tumor, NRF2 activation, or prognosis of a cancer patient on the basis of a decrease in the quantitated value(s) as an index."

As described above, the low-value miRNA to be assayed is one or more microRNAs selected from the group consisting of hsa-miR-507, hsa-miR-634, hsa-miR-450a, hsa-miR-129-5p, hsa-miR-639, hsa-miR-337, hsa-miR-153, and hsa-miR-556. Among them, one or more microRNAs selected from the group consisting of hsa-miR-507, hsa-miR-634, hsa-miR-450a, and hsa-miR-129-5p, in particular, exhibit a low quantitation value in the case of a malignant tumor. Thus, preferably, the 4 microRNAs are preferentially selected as assay targets.

The human specimen is literally a specimen derived from a human. In many cases, donors of specimens are cancer patients. In the present invention, the donors of specimens may include patients whose cancers have been undiagnosed. No particular limitation is imposed on the type of specimens, so long as the change in low-value miRNAs in tumor cells can be detected. In the simplest case, the specimen is a tumor specimen (i.e., tumor itself), and specific examples thereof include tumor specimens and biopsy specimens which have been removed through surgery or under an endoscope. So long as the above requirement is satisfied, any human tissue may be used as the tissue specimen. Generally, blood specimens (e.g., serum, plasma, and whole blood), urine specimens, lung lavage fluid specimens, sputum specimens, lymph fluid specimens, cerebrospinal fluid specimens, etc. may be used in accordance with needs.

No particular limitation is imposed on the low-value miRNA quantitation means, and any known means and other means to be developed in the future may be employed. Typical examples of such means include RNA quantitation methods based on gene amplification methods such as RT-PCR. From the viewpoint of processing numerous samples at high speed, a real-time RT-PCR technique employing an automated detection device is a more preferred method. Other examples of such means include Northern plotting.

When the quantitated value of a low-value miRNA is relatively lower than that of an internal control at a threshold value, the quantitated value of the miRNA is considered to be decreased. The threshold value may be specifically predetermined for each miRNA. The threshold value is preferably set to a value corresponding to a decrease of at least 30%. More preferably, as disclosed in the below-described Examples, the threshold value is set to a value corresponding to a decrease of 250%.

Among 8 low-value miRNAs, a decrease in each quantitated value may be employed as an index. The greater the increase in the number of miRNAs which exhibit a "decrease in quantitated value," the stronger the malignancy of a tumor. In such a case, NRF2, in particular, in the tumor is activated, and the prognosis of the patient is aggravated.

That is, a decrease in a quantitated value or values of one or more microRNAs selected from the group consisting of hsa-miR-507, hsa-miR-634, hsa-miR-450a, hsa-miR-129-5p, hsa-miR-639, hsa-miR-337, hsa-miR-153, and hsa-miR-556 may be employed as an index for elevation in tumor malignancy, NRF2 activation, or aggravation of prognosis of a patient.

In a more preferred mode of the low value determination method of the present invention, among the above 8 low-value miRNAs, one or more microRNAs selected from the group consisting of 4 microRNAs "hsa-miR-507, hsa-miR-634, hsa-miR-450a, and hsa-miR-129-5p" are selected. The results of the case in which the tumor malignancy and the like were differentiated by use of the 4 microRNAs are disclosed in the below-described Examples.

In the low value determination method of the present invention, one to three gene mutations selected from the group consisting of NRF2 gene mutation, KEAP1 gene mutation, and p62 protein accumulation in the tumor may be detected, and the gene mutation(s) may be added to the index for tumor malignancy, activation of NRF2, in particular, in the tumor, and prognosis of a patient. Through addition of these elements to the index, differentiation accuracy of the low value determination method of the present invention can be further enhanced. The NRF2 gene mutation and/or KEAP1 gene mutation are(is) any of missense mutation including point mutation, nonsense mutation, and frameshift mutation. The amino acid substitution-mode mutation in the Examples is an example of missense mutation. No particular limitation is imposed on the method of detecting the gene mutations. Examples of the detection method include PCR-dependent typing methods such as pyrosequencing, MALDI-TOF MS, RFLP, SSCP, SSOP, RNase protection, RDA, RAPD, and AFLP; and non-PCR-dependent typing methods such as TaqMan PCR and Invader.

When one to three elements selected from the group consisting of NRF2 gene mutation, KEAP1 gene mutation, and p62 protein accumulation in the tumor are added to the index employed in the low value determination method of the present invention, "presence" among presence and absence of these gene mutations and protein accumulation may be added to the index for an increase in tumor malignancy, activation of NRF2, and aggravation of prognosis of a patient. In the below-described Examples, the number of "present" gene mutations (score) is added to the number of "decrease" in the quantitation values of the aforementioned 4 low-value miRNA (score), and the sum is employed as the final index for tumor malignancy, NRF2 activation, and prognosis of a patient. When the number (score) is 0 or 1, the group is called a "low-score group," whereas when the number (score) is 2 or greater, the group is called a "high-score group." A significant difference in patients' prognosis has been found between the two groups. Thus, in the low value determination method of the present invention, it is possible and preferable to assess whether aggravation of tumor malignancy, etc. is represented at each level of elements which are indexes, and to employ the number (score) of elements representing aggravation of tumor malignancy, etc. as an index for tumor malignancy, etc. The manner of setting the threshold value of the score varies depending on the type of the target cancer, the selected index, etc., and is not limited to the contents of the below-described Examples. The essential concept of the low value determination method of the present invention is based on the finding that, among others, a "decrease" in miRNA quantitated value serving as an index for differentiation closely relates to activation of NRF2 which leads to aggravation of cancer malignancy, whereby prognosis of the cancer can be appropriately differentiated. Thus, there is no essential meaning in other elements of design such as setting a threshold value. When a patient is diagnosed to have a high cancer risk by the low value determination method of the present invention, medical treatment such as administration of the below-described cancer therapeutic agent of the present invention may be executed.

(2) High Value Determination Method of the Present Invention

As described above, the high value determination method of the present invention is directed to a "microRNA assay method, characterized by comprising quantitating "high-value miRNA" in a human specimen, and differentiating malignancy of a tumor, NRF2 activation, or prognosis of a cancer patient on the basis of an increase in the quantitated value(s) as an index.

As described above, the high-value miRNA to be assayed is one or more microRNAs selected from the group consisting of hsa-miR-26a, hsa-miR-17-3p, hsa-miR-190, hsa-miR-567, hsa-miR-125b, hsa-miR-125a, hsa-miR-432*, and hsa-miR-29.

The "human specimen" and "means for quantitating high-value miRNA" are the same as those in relation to the aforementioned "low value determination method of the present invention."

When the quantitated value of a high-value miRNA is higher than that of an internal control at a threshold value, the quantitated value of the miRNA is considered to increase. The threshold value may be specifically predetermined for each miRNA. The threshold value is preferably set to a value corresponding to an increase of at least 30%. More preferably, as disclosed in the below-described Examples, the threshold value is set to a value corresponding to an increase of ≥50%.

Among 8 high-value miRNAs, an increase in each quantitated value may be employed as an index. The greater the increase in the number of miRNAs which exhibit an "increase in quantitated value," the stronger the malignancy of a tumor. In such a case, NRF2, in particular, in the tumor is activated, and the prognosis of the patient is aggravated.

That is, an increase in a quantitated value or values of one or more microRNAs selected from the group consisting of hsa-miR-26a, hsa-miR-17-3p, hsa-miR-190, hsa-miR-567, hsa-miR-125b, hsa-miR-125a, hsa-miR-432*, and hsa-miR-29 may be employed as an index for elevation in tumor malignancy, NRF2 activation, or aggravation of prognosis of a patient.

In the high value determination method of the present invention, one to three elements selected from the group consisting of NRF2 gene mutation, KEAP1 gene mutation, and p62 protein accumulation in the tumor may be detected, and the gene mutation(s) may be added to the index for tumor malignancy, activation of NRF2, in particular, in the tumor, and prognosis of a patient. The feature is the same as described in relation to the "low value determination method of the present invention."

When these gene mutations and protein accumulation are added to the index employed in the high value determination method of the present invention, "presence" among presence and absence of these gene mutations may be added to the index for an increase in tumor malignancy, activation of NRF2, and aggravation of prognosis of a patient.

Thus, in the high value determination method of the present invention, it is possible and preferable to assess whether aggravation of tumor malignancy, etc. is represented at each level of elements which are indexes, and to employ the number (score) of elements representing aggravation of tumor malignancy, etc. as an index for tumor malignancy, etc. The manner of setting the threshold value of the score varies depending on the type of the target cancer, the selected index, etc. The essential concept of the high value determination method of the present invention is based on the finding that, among others, an "increase" in miRNA quantitated value serving as an index for differentiation closely relates to activation of NRF2 which leads to aggravation of malignancy of a cancer, whereby prognosis of the cancer can be appropriately differentiated. Thus, there is no essential meaning in other elements of design such as setting a threshold value. When a patient is diagnosed to have a high cancer risk by the high value determination method of the present invention, medical treatment such as administration of an antagonistic cancer therapeutic agent may be executed. The antagonistic cancer therapeutic agent refers to, for example, a cancer therapeutic agent essentially containing a synthetic oligo that can antagonistically inhibit the function of an miRNA which exhibits promoted expression confirmed in the high value determination method of the present invention.

<Cancer Therapeutic Agent of the Present Invention>

(1) The Cancer Therapeutic Agent of the Present Invention

As described above, the cancer therapeutic agent of the present invention is a "cancer therapeutic agent consisting of a nucleic acid(s) including one or more nucleotide sequences selected from the group consisting of the nucleotide sequences of hsa-miR-507 (SEQ ID NO: 1), hsa-miR-634 (SEQ ID NO: 2), hsa-miR-450a (SEQ ID NO: 3), hsa-miR-129-5p (SEQ ID NO: 4), hsa-miR-639 (SEQ ID NO: 5), hsa-miR-337 (SEQ ID NO: 6), hsa-miR-153 (SEQ ID NO: 7), and hsa-miR-556 (SEQ ID NO: 8)."

As described above, regarding all the microRNAs having the aforementioned nucleotide sequences (SEQ ID NOs: 1 to 8), expression thereof is suppressed in cancer cells having promoted or stabilized NRF2 activity, high resistance to therapy, and high malignancy. The cancer therapeutic agent of the present invention provides medical treatment for such a cancer having resistance to therapy, and high malignancy through the following mechanism. Specifically, a nucleic acid serving as a microRNA whose expression is suppressed in cancer cells is administered to a cancer patient, to thereby inactivate the NRF2 to weaken the target cancer.

NRF2 activity is intrinsically high in some cancer cells. However, in many cases, NRF2 is activated through giving stress to cancer cells. One stress factor is a therapeutic action taken to cancer, and the specific examples include cancer chemotherapy, cancer radiotherapy, and surgery. These actions can be therapeutic actions to cancer, but kill the target cancer cells. Thus, stress by such actions is conceived to promote NRF2 activity in cancer cells. Therefore, in a preferred embodiment of use of the cancer therapeutic agent of the present invention, the cancer therapeutic agent is used in combination with stress-giving to cancer, through cancer chemotherapy, etc. as described above. Notably, similar to surgery, stimulation of cancer cells through biopsy is thought to give a physical stress to cancer cells. Thus, the cancer therapeutic agent may be used in combination with biopsy. The concept "combination" encompasses temporal concepts, "before," "during (simultaneous)," and "after." In other words, the cancer therapeutic agent of the present invention may be administered "before" a stress-giving action such as administration of another anticancer agent, surgery, or biopsy. Alternatively, the cancer therapeutic agent of the present invention may be taken "simultaneously" with another anticancer agent, or may be taken as a mixture (pharmaceutical composition) with another anticancer agent. Yet alternatively, the cancer therapeutic agent of the present invention may be administered "after" a stress-giving action such as administration of another anticancer agent, surgery, or biopsy.

No particular limitation is imposed on the "nucleic acid including the aforementioned 8 miRNA nucleotide sequences," serving as the essential components of the cancer therapeutic agent of the present invention, so long as the nucleic acid includes the sequence(s) and can exhibit functions of miRNA in cancer cells. Although the nucleic acid may be an "miRNA" present in the living body as a single-strand RNA, it is preferably a double-stranded nucleic acid, from the viewpoint of stability in the living body. Specific examples of the double-stranded nucleic acid include a "double-stranded RNA" composed of a pair of an miRNA sequence and a complementary RNA thereof, a "RNA-DNA complex double strand," a "RNA-PNA complex double strand," and a "RNA-LNA complex double strand." PNA (peptide nucleic acid) refers to a nucleic acid homologue having a skeleton in which a deoxyribose-phosphate skeleton (nucleic acid skeleton) is substituted by (2-aminoethyl)glycine. LNA (locked nucleic acid) (also called BNA: bridged nucleic acid) refers to an artificial nucleic acid having enhanced stability by virtue of 2'-position and 4'-position of the sugar moiety being linked to each other via a carbon chain (D. A. Braasch, D. R. Corey, Chem. Biol., 8, 1 (2001)). In the below-described Examples, a "double-stranded RNA" is used.

A nucleic acid of interest may be synthesized through a known RNA synthesis method or a similar technique. Examples of the RNA synthesis method include a phosphoramidite method and an improved method thereof (M. Kataoka, Y. Hayakawa, J. Org. Chem., 64, 6087 (1999)), an H-phosphonate method and an improved method thereof (T. Wada, F. Handa, Y. Sato, S. Kawahara, M. Sekine, Nucleic Acids Symp. Ser., 37, 19 (1997)), and an enzymatic synthesis method (in vitro transcription method). In accordance with needs, there may be performed mono-modification of α-oxygen of the phosphate moiety of nucleic acid (e.g., S-oligo modification), modification of the phosphate ester moiety, modification of the phosphate skeleton with PNA or the like, modification of the sugar moiety with the aforementioned LNA or the like, and other modifications. Alternatively, any of commercial nucleic acid products and contract manufactured nucleic acid products may also be used in the present invention.

The thus-obtained nucleic acid including a specific miRNA nucleotide sequence(s) may be used as an essential component(s) of the cancer therapeutic agent of the present invention. When the cancer therapeutic agent of the present invention is administered to a human body, the agent is generally administrated as a pharmaceutical composition of the present invention, as described below. The daily dose of the cancer therapeutic agent of the present invention in the case of administration to a human body is about 0.01 μg to about 10 mg for an adult. A single or divided (2 to 5 times) administration per day, or repetition of such administration with intervals of several days may be applicable.

As described above, the cancer to which the cancer therapeutic agent of the present invention can be applied is not determined by the type thereof but rather preferentially satisfies the condition that expression of specific miRNAs (8 miRNAs: hsa-miR-507, hsa-miR-634, hsa-miR-450a, hsa-miR-129-5p, hsa-miR-639, hsa-miR-337, hsa-miR-153, and hsa-miR-556, and typically 4 miRNAs: hsa-miR-507, hsa-miR-634, hsa-miR-450a, and hsa-miR-129-5p) is suppressed, whereby NRF2 activity in target cancer cells is enhanced or stabilized. In other words, the cancer therapeutic agent of the present invention is actively planned to be administered to a cancer patient who is differentiated, by the low value determination of the present invention, to have suppressed NRF2 due to suppressed expression of the aforementioned specific microRNAs. In this regard, the combination of the nucleic acids including miRNA nucleotide sequences serving as the essential components of the cancer therapeutic agent of the present invention may be ready-made (typically, nucleic acids including the aforementioned 4 miRNA nucleotide sequences). Alternatively, the cancer therapeutic agent of the present invention may also be tailored such that the essential component thereof is a nucleic acid(s) including a nucleotide sequence(s) of miRNA(s) whose expression suppression is ascertained. Thus, the specific miRNAs, serving as essential components of the cancer therapeutic agent of the present invention, may be used singly or in combination of two or more species. No particular limitation is imposed on the cancer to which the cancer therapeutic agent of the present invention is applied, and examples of the target cancer include esophageal cancer, lung cancer, breast cancer, oral cancer, stomach cancer, colorectal cancer, liver cancer, uterine cancer, skin cancer, and osteosarcoma, as described above.

Examples of the anticancer agent serving as one stress means to cancer cells employed in combination with the cancer therapeutic agent of the present invention include alkylating agents such as ifosfamide, cyclophosphamide, dacarbazine, temozolomide, nimustine, busulfan, procarbazine, and melphalan; molecular target drugs such as ibritumomab tiuxetan, imatinib, everolimus, erlotinib, gefitinib, gemtuzumab ozogamicin, sunitinib, cetuximab, sorafenib, dasatinib, tamibarotene, trastuzumab, tretinoin, panitumumab, bevacizumab, bortezomib, lapatinib, and rituximab; antimetabolites such as enocitabine, capecitabine, carnofur, cladribine, gemcitabine, cytarabine, cytarabine ocfosfate, tegaful, tegaful/uracil, tegaful/gimeracil/oteracil potassium, doxifluridine, nelarabine, hydroxycarbamide, fluorouracil, fuludarabin, pemetrexed, pentostatin, mercaptopurine, and methotrexate; plant alkaloids such as irinotecan, etoposide, eribulin, sobuzoxane, docetaxel, nogitecan, paclitaxel, vinorelbine, vincristine, vindesine, and vinblastine; anticancer antibiotics such as actinomycin D, aclarubicin, amurubicin, idarubicine, epirubicin, zinostatin stimalamer, daunorubicin, doxorubicin, pirarubicin, bleomycine, pepleomycin, mytomycin C, mitoxantrone, liposomal doxorubicin; platinum agents such as oxaliplatin, carboplatin, cisplatin (CDDP), and nedaplatin; hormone drugs such as anastrozole, exemestane, estramustine, ethinylestradiol, chlormadione, tamoxifen, dexamethasone, toremifene, bicalutamide, flutamide, prednisolone, fosfestrol, mitotane, methyltestosterone, medroxyprogesterone, mepitiostane, leuprorelin, and letrozole; and biological response modifiers such as interferon-α, interferon-β, interferon-γ, interleukin, ubenimex, dried BCG vaccine, and lentinan. When activation of NRF2 is observed by treatment with any of these anticancer agents, the cancer can be found to be a suitable target of the cancer therapeutic agent of the present invention. Regarding cancer radiotherapy, ion radiotherapy and the like may be employed, in addition to conventional radiotherapy techniques. Also, surgery and biopsy may be employed as described above.

Separate from the consideration of stress-applied conditions of cancer, the cancer therapeutic agent of the present invention may also be applied to the case where complete treatment of cancer is abandoned and "co-existence with cancer" is allowed. In other words, the cancer therapeutic agent of the present invention is thought to be suitable for the case where aggravation of cancer is prevented through suppressing activation of NRF2 in cancer cells, leading to cancer patients living out their lives.

<Pharmaceutical Composition of the Present Invention>

As described above, the pharmaceutical composition is a "pharmaceutical composition for treatment of cancer, the composition comprising the aforementioned cancer therapeutic agent of the present invention."

As described above, the cancer therapeutic agent of the present invention itself and the "pharmaceutical composition" containing the therapeutic agent serving as an active ingredient are administered to a human body. In case where the cancer therapeutic agent itself is directly administered, an injection or the like is mixed with the agent when it is used. Thus, such a case is also encompassed in the pharmaceutical composition.

The pharmaceutical composition of the present invention is prepared by mixing the cancer therapeutic agent of the present invention with an appropriate pharmaceutical preparation carrier, into the form of pharmaceutical preparation composition. The pharmaceutical preparation carrier may be selected in accordance with the mode of use, and examples of the carrier which may be used in the invention include a vehicle or diluent such as a filler, an extender, a binder, a humidifier, a disintegrator, a surfactant, etc. No particular limitation is imposed on the form of the composition, so long as the composition can effectively contain the cancer therapeutic agent of the present invention. Examples of the composition form which may be employed in the invention include solids such as tablet, powder, granule, and pill, and ointment. Generally, the form is suitably injections such as liquid, suspension, and emulsion. The cancer therapeutic agent of the present invention may be formed into a dry product from which a liquid preparation can be prepared by adding an appropriate carrier when used. The effect of the cancer therapeutic agent of the present invention can be enhanced through employment of drug delivery systems such as nano-particles formed of cyclodextrin-containing polymer, polymer micelle, stabilized nucleic acid lipid particles (SNALP), and polyfunctional envelope-type nano device (MEND), in the pharmaceutical composition of the present invention.

The thus obtained pharmaceutical composition is administered to a patient via an appropriate administration route suited for the form thereof. The pharmaceutical composition in the injection form may be administered intravenously, intramuscularly, hypodermally, intradermally, or intraperitoneally. The pharmaceutical composition in the solid form may be administered perorally or enterically. The amount of the therapeutic agent of the present invention in the pharmaceutical composition is selected appropriately according to administration route of the composition, mode of administration, purpose of use, conditions of the target patient, etc., and is not constant. Generally, the cancer therapeutic agent of the present invention is prepared into a corresponding pharmaceutical composition having an agent content of about 0.1 to about 95 mass %. Preferably, the above daily dose (about 0.01 µg to about 10 mg for an adult) is administered singly or in a divided (2 to 5 times) manner, or repetition of such administration with intervals of several days may be applicable.

EXAMPLES

The present invention will next be described by way of examples.

1. Materials and Methods

Before providing the results of the Examples, the materials and test methods employed therein will be described.

(1) Cell Culture Media and Primary Tumor Samples

HeLa, Lk-2, A549, and JHH-5 cells were purchased from the American Culture Collection (USA). The cells were cultured in Dulbecco's modified Eagle's medium (for HeLa and Lk-2 cells), in RPMI 1640 medium (for A549 cells), or in Williams' E medium (for JHH-5 cells), supplemented with 10% fetal bovine serum, penicillin, and streptomycin, at 37° C. with 5% $CO_2$.

Primary esophageal squamous cell carcinoma (ESCC) samples (30 samples in total) and the corresponding non-cancerous esophageal mucosa had been obtained from patients treated at the Tokyo Medical and Dental University Hospital between April 2005 and June 2007. The samples were immediately frozen in liquid nitrogen and stored at −80° C. until genomic DNA and RNA were extracted. Written consent was always obtained in the formal style. The collection and analysis of patient samples were approved by the Tokyo Medical and Dental University Institutional Review Board (approval #2010-5-2). Tumor samples fixed with formalin and embedded in paraffin were subjected to immunohistochemical analysis. Relevant clinical and survival data were obtained from all patients. None of the patients had received chemotherapy or radiation before surgery. Disease stage was defined in accordance with the tumor-lymph node-metastases classification of esophageal cancer. Patients who were treated by non-curative resection or who died of other diseases were not included in this study. The median follow-up period for the survival patients was 35 months (4 to 69 months).

(2) Antibodies and Reagents

There were used rabbit polyclonal anti-NRF2 antibody (Santa Cruz Biotechnology) (for Western blotting), rabbit polyclonal anti-NRF2 antibody (Santa Cruz Biotechnology) (for immunohistochemistry), rabbit polyclonal anti-KEAP1 antibody (Proteintech), mouse monoclonal anti-ME-1 antibody (Santa Cruz Biotechnology), rabbit anti-XIAP antibody (Cell Signaling), rabbit anti-APIP antibody (Abcam), rabbit anti-OPA1 antibody (Abcam), rabbit anti-TFAM antibody (Sigma), and mouse monoclonal anti-β-actin antibody (Sigma). For the treatment of cultured cells, hydrogen peroxide (Wako) or cisplatin (Wako) was used.

(3) Cell Survival Assay

Cell survival was assessed by the crystal violet (CV) staining assay. Specifically, the cells were washed in PBS and fixed with 0.2% CV in 10% formaldehyde in PBS for 3 minutes. After removal of excess CV solution and complete drying in air, the stained cells were lysed with 2% SDS solution, by shaking the plate for one hour. Optical density (OD) absorbance was measured at 560 nm by means of a microplate reader (ARVOmx; Perkinelmer), and percent absorbance of each well was determined. The OD absorbance values of cells in control wells were arbitrarily set to 100% so as to determine the percentage of viable cells.

(4) Screening System Using ARE-Luciferase Reporter

The luciferase reporter plasmid was prepared by inserting a human NQO-1 promoter region 5'-CTCAGCCTTC-CAAATCGCAGTCACAGTGACTCAGCAGAATC-3' (SEQ ID NO: 19) including an antioxidant response element (ARE) into an MluI/XhoI site in pGL3 vector (Promega). Specifically, a pair of synthetic oligonucleotides complementary with each other shown in Table 2 (upper; SEQ ID NO: 20, lower; SEQ ID NO: 21) were annealed, to thereby form a double-stranded DNA, and a double-stranded DNA having cohesive ends complementary to the MluI/XhoI site was prepared by use of MluI and XhoI. The thus-produced double-stranded DNA fragment was inserted into the MluI/XhoI site, to thereby yield a recombinant pGL3 (reporter plasmid) of interest.

TABLE 2

| Name | Sequence (5'-3') |
|---|---|
| NQO1-ARE-MluI/XhoI | CGACGCGTCTCAGCCTTCCAAATCGCAGTCACAGT GACTCAGCAGAATCCTCGAGCGG |
| NQO1-ARE-XhoI/MluI | CCGCTCGAGGATTCTGCTGAGTCACTGTGACTGCG ATTTGGAAGGCTGAGACGCGTCG |

Firstly, the reporter plasmid was transiently transfected into HeLa cells (1×10⁷ cells/dish) in a 10 cm dish. 24 hours after transfection, the cells (1×10⁴ cells/well) were seeded on a 96-well plate, and the next day, 20 nmol/L of each of the 470 double-stranded RNA fragments, derived from Pre-miRNA precursor library-Human V3 (Ambion) or control miRNA was transfected. After two days, firefly luciferase activity was measured by means of a microplate reader (ARVOmx; Perkinelmer) using Bright-Glo Luciferase Assay System (Promega). At the same time, living cells were detected through CV staining assay. ARE activity was calculated from the luciferase activity per living cell.

(5) MicroRNAs (miRNAs) and Small Interference RNAs (siRNAs)

miRNAs or siRNAs (20 nmol/L) were transfected individually into cells using Lipofectamin RNAiMAX (Invitrogen) according to the manufactures' instructions. Double-stranded RNAs mimicking human mature miRNA (hsa-miR-507 (PM10509), hsa-miR-129-5p (PM10195), hsa-miR-450a (PM11192), and hsa-miR-634 (PM11538)), and control miRNA (negative control #1) were obtained from Ambion. The siRNA to NRF2 (siGENOME SMARTpool; M-003755-02-0005) and siRNA to KEAP1 (siGENOME SMARTpool; M-012453-00-0005) were obtained from Thermo Scientific Dharmacon.

(6) Conventional Luciferase Assay

Luciferase reporter plasmids were made by inserting the 3'-untranslated region of NRF2, ME1, or NQO1 (UTR: SEQ ID NOs: 49 to 51) at a downstream site of the luciferase gene within the pmirGlO Dual-Luciferase miRNA Target Expression Vector (Promega). All site-specific mutations were generated using the GeneTailor site-directed mutagenesis system (Invitrogen) or KOD mutagenesis kit (TOYOBO). Luciferase reporter plasmids and pTK plasmids serving as the internal control were co-transfected in HeLa cells, and the next day, the double-stranded RNA mimicking human mature miRNA or control miRNA was transfected. After 2 days, firefly and renilla luciferase activities were measured using the Dual-Luciferase Reporter Assay System (Promega), and relative luciferase activity was calculated by normalizing the firefly luciferase reading with its corresponding internal renilla luciferase control.

(7) Western Blotting

Whole cell lysates were subjected to SDS-PAGE, and proteins were transferred onto PVDF membranes (GE Healthcare) After blocking with TBS containing 0.05% Tween 20 and 5% non-fat dry milk for 1 hour, each membrane was reacted with an antibody overnight. Dilution factors for primary antibodies were as follows: rabbit anti-NRF2 (1/1,000), rabbit anti-KEAP1 (1/1,000), mouse anti-ME1 (1/1,000), and mouse anti-R-actin (1/5,000). The membrane was washed and exposed to HRP-conjugated anti-mouse or rabbit IgG antibodies (both at 1/2,000) for 2 hours. The bound antibodies were visualized with HRP staining solution or with an ECL Western blotting kit (Cell Signaling Technology) according to the manufacturer's instructions.

(8) Quantitative RT-PCR

Total RNA was isolated using a TRIzol (registered trademark) reagent (Invitrogen) according to standard procedures. Single-stranded cDNA obtained from the total RNA was amplified with a primer set specific for each gene. Quantitative real-time RT-PCR (qRT-PCR) was performed using the KAPA SYBR system (Kapa Biosystems) and an ABI PRISM 7500 sequence detection System (Applied Biosystems) according to the manufacturer's instructions. Gene expression values are given as ratios (differences between the Ct values) between the genes of interest and an internal control (GAPDH) or U6, and subsequently normalized with the value in the control cells (relative expression level). Tables 3 and 4 provide information on the primers and TaqMan probes employed. In Table 3, SEQ ID NOs 22 to 32 were assigned to the left-column nucleotide sequences showing forward primers, sequentially downward from the top, and likewise, SEQ ID NOs 33 to 43 were assigned to the right-column nucleotide sequences showing reverse primers. Similarly in Table 4, sequentially downward from the top, SEQ ID NOs 44 to 48 were assigned to the nucleotide sequences of TaqMan probes.

TABLE 3

| Gene | Forward PCR Primer | Reverse PCR Primer |
|---|---|---|
| NRF2 | | |
| Exon2 | ACCATCAACAGTGGCATAATGTG | GGCAAAGCTGGAACTCAAATCCAG |
| KEAP1 | | |
| Exon2 | GCAAATGGATTCTGCTTCACCTACTT | TCAAACTGTGGAGACTACACCACCAT |
| Exon3 | CATCACAATGTACGCGGTTCCTATTA | GGCACAGAATCAAAGGTCACTGACTA |
| Exon4 | GATGAACCTGTCTCTTTAAGGGGGAA | GGAGAGAGAGAAGCTTGGACTCTATCAGAA |
| Exon5 | GTGAGAAGGGAGAGGAGAGAGGAAAGGTCT | TCCAGCTGGGCAACAGAGCGAGACCTTGTTT |
| Exon6 | AAGAGACTAAGGTTTTGCTATGTTGC | AGCTGAAACTGAAGGACAACTGTGTG |

TABLE 3-continued

| Gene | Forward PCR Primer | Reverse PCR Primer |
|---|---|---|
| NQO1 | CATTCTGAAAGGCTGGTTTG | GGCTGCTTGGAGCAAAATAC |
| HO1 | GCTACCTGGGTGACCTGTCT | GGGCAGAATCTTGCACTTTG |
| GPX2 | GGCTTTCATTGCCAAGTCCTTC | CTATATGGCAACTTTAAGGAGGCGC |
| TXNRD1 | CTTTTTCATTCCTGCTACTCTACC | CTCTCTCCTTTTCCCTTTTCC |
| GAPDH | CGGAGTCAACGGATTTGGTCGTAT | AGCCTTCTCCATGGTGGTGAAGAC |

TABLE 4

| miRNA | Target Sequence |
|---|---|
| hsa-miR-507 | UUUUGCACCUUUUGGAGUGAA |
| hsa-miR-634 | AACCAGCACCCCAACUUUGGAC |
| hsa-miR-450a | UUUUGCGAUGUGUUCCUAAUAU |
| hsa-miR-129-5p | CUUUUUGCGGUCUGGGCUUGC |
| RNU6B | CGCAAGGAUGACACGCAAAUUCGUGAAGCGUUCC AUAUUUUU |

For miRNAs, real-time reverse transcription PCR (RT-PCR) was performed using an ABI Prism 7500 Fast Real-time PCR System (Applied Biosystems), Taqman Universal PCR Master Mix (Applied Biosystems), Taqman Reverse Transcription kit (Applied Biosystems), and Taqman MicroRNA Assays (Applied Biosystems), according to the manufacturers' instructions. Expression levels of miRNA genes were based on the amount of the target message which relates to that of the RNU6B transcript serving as a control to normalize the initial input of total RNA.

(9) Immunohistochemistry

Tumor samples were fixed with 10% formaldehyde in PBS, embedded in paraffin, sectioned into 4-μm-thick slices, and subjected to immunohistochemical staining of NRF2 or ME1 with the avidin-biotin-peroxidase method. Sections from paraffin-embedded tumor samples were deparaffinized with xylene, and rehydrated in ethanol. After retrieval of antigens by boiling in 10 mM citrate buffer (pH 6.0), the sections were treated with 0.3% hydrogen peroxide in methanol to inactivate the endogenous peroxidase. Subsequently, the sections were incubated with an anti-NRF2 antibody (dilution: 1/1,000) or anti-ME1 antibody (dilution: 1/500) at 4° C. overnight. The bound antibody was visualized using diaminobenzidine (VECTASTAIN_Elute ABC kit, Vector Laboratories) serving as a chromogen, and the sections were lightly counterstained with hematoxylin.

(10) Mutation Analysis of NRF2 and KEAP1

The genomic regions containing exon 2 of NRF2 or all coding regions of KEAP1 were amplified by PCR using KOD-plus (TOYOBO). PCR products were purified using ExoSAP-IT (GE Healthcare) and subjected to sequence analysis. Information on primers is given in Table 3.

(11) Expression Array Analysis and Pathway Analysis Using IPA

For the gene expression array analysis, the Agilent 4×44K gene expression array (Agilent Technologies) was used according to the manufacturer's instructions. Each gene array experiment was performed in duplicate and the data were analyzed using GeneSpring (Agilent Technologies).

The expression data and data from the TargetScan program were subjected to an ingenuity pathway analysis (IPA) (Ingenuity Systems).

(12) In Vivo Tumor Growth Assay and Administration of miRNAs

Seven-week-old female BALB/c nude mice were purchased from Oriental Yeast Co., Ltd. and maintained under pathogen-free conditions. 200 μL of PBS containing $1.0 \times 10^7$ cells were subcutaneously injected into the flank of mice. A mixture of 1-nmol double-stranded RNA (Ambion) and 200 μL of AteroGene (Koken) was administered into the space between the tumor and skin. The mice were treated with cisplatin at a dose of 5 mg/kg body weight by way of intraperitoneal administration. On day 35 after injection of cells, the mice were euthanized and tumors were resected. All experimental protocols conducted on the mice were approved by the Tokyo Medical and Dental University Animal Care and Use Committee.

(13) Statistical Analysis

Differences between subgroups were studied by the Student's t-test. Clinicopathologic variables pertaining to the corresponding patients were analyzed by the $\chi^2$ test or Fisher's exact test. For the analysis of survival, Kaplan-Meier curves were constructed for groups based on univariate predictors, and differences between groups were studied using the log-rank test. Results of in vivo experiments and the cell survival assay in A549 cells were analyzed for statistical significance using a two-way ANOVA (a two-way analysis of variance). A calculated P value of <0.05 was considered to mean statistically significant.

2. Examples

[Example 1] Screening of miRNAs Negatively Regulating the Transcriptional Activity of NRF2

In order to identify miRNA negatively regulating the transcriptional activity of NRF2, we screened a miRNA library using the luciferase reporter system. The system enables the measurement of luciferase gene expression by activating the ARE (antioxidative responsible element). With this reporter system, we confirmed that the ARE activity changed according to the level of NRF2 protein in HeLa cells (FIG. 1). FIG. 1 shows the validation results of the ARE reporter system using siRNA. Specifically, Hela cells were co-transfected with an ARE-luciferase reporter plasmid and an internal control vector, and 24 hours later, transfected with control siRNA, or NRF2-siRNA (a) or KEAP1-siRNA (b). After 48 hours of transfection with siRNA, the cell lysate was subjected to SDS-PAGE, and immunoreacted with the indicated antibodies (upper panel). Separately, firefly or renilla luciferase activity was measured, and the ARE activity relative to that in Mock is shown on the vertical axis (lower panel). Bars indicate standard deviation (SD).

FIG. 2-1 shows the results of screening of miRNAs negatively regulating the transcriptional activity of NRF2.

FIG. 2-1 (a) shows an miRNA library screening method using an ARE reporter system. For the screening of 470 double-stranded RNAs, HeLa cells were sequentially transfected with each miRNA together with the reporter plasmid, and then the ARE activity in each transfected cell was calculated as the luciferase activity per living cell, as measured by the crystal violet (CV) staining assay. Briefly, the ARE-luciferase reporter plasmid and each miRNA from the library were sequentially transfected into HeLa cells, and after 48 hours, luciferase activity or the number of living cells was measured using the Bright-Glo Luciferase Assay System or crystal violet (CV) staining assay, respectively. The ARE activity for each miRNA-transfected cell was calculated as the luciferase activity per living cell.

FIG. 2-1 (b) shows a summary of the results for ARE activity in miRNA-transfected cells. The ARE activity relative to that in control-miRNA-transfected cells is indicated on the vertical axis. Eight miRNAs with a relative ratio of 0.5 or less were identified as candidates by this screening system. Also, eight miRNAs with a relative ratio of 1.5 or more were similarly identified as candidates by this screening system.

FIG. 2-1 (c) shows the results of the validation of four candidate miRNAs by luciferase assay. HeLa cells were co-transfected with an ARE-luciferase reporter plasmid and an internal control vector, and after 24 hours, hsa-miR-507, -634, -450a, or -129-5p, or control miRNA was transfected. After 48 hours of transfection with miRNAs, firefly or renilla luciferase activity was measured. The ARE activity relative to that in control-miRNA-transfected cells is indicated on the vertical axis. Bars indicate standard deviation (SD).

FIG. 2-1 (d) shows the results of expression analysis of NQO1 mRNA in miRNA-transfected cells. HeLa cells were transfected with hsa-miR-507, -634, -450a, or -129-5p, or control miRNA. After 48 hours of transfection, the mRNA level of the NQO1 gene was measured by qRT-PCR. The expression of the GAPDH gene was used as the internal control. The expression level relative to that in control-miRNA-transfected cells is indicated on the vertical axis. Bars indicate standard deviation (SD).

FIG. 2-2 shows the results of expression analysis of NRF2 target genes. HeLa cells were transfected with siRNA (control, NRF2, or KEAP1) (a), or miRNA (control miRNA, hsa-miR-507, -634, -450a, or -129-5p) (b). After 48 hours of transfection, the mRNA expression level of four NRF2 target genes, NQO1, GPX2 and TXRND1, were measured by qRT-PCR. The expression of the GAPDH gene was used as the internal control. The expression level relative to that in control-siRNA- or control-miRNA-transfected cells is indicated on the vertical axis. Bars indicate standard deviation (SD). The results of Western blotting and the results for NQO1 expression shown in (b) are also shown in FIG. 3. a, and FIG. 2-1 (d).

We focused on the top four miRNAs (hsa-miR-507, -634, -450a, and -129-5p), and from FIGS. 2-1 (c), 2-1 (d) d, and 2-2, it was confirmed that their transfection actually reduced ARE activity and also down-regulated transcriptional activity of known NRF2 target genes (NQO1, HO1, GPX2, and TXRND1).

These results suggest that the screening system for known target genes could successfully identify at least four candidate miRNAs negatively regulating the transcriptional activity of NRF2. Also, as shown in FIG. 2-1 (b), eight miRNAs (hsa-miR-26a, has-miR-17-3p, hsa-miR-190, hsa-miR-567, hsa-miR-125b, hsa-miR-125a, hsa-miR-432*, and hsa-miR-29) were confirmed to have a relative ratio of ARE activity of 1.5 or more, as compared with control-miRNA-transfected cells.

[Example 2] Identification of NRF2 as a Functional Target of the Candidate miRNAs To identify the functional target for the four candidate miRNAs (hsa-miR-507, hsa-miR-634, hsa-miR-450a and hsa-miR-129-5p), we first investigated as to whether genes known to be associated with the NRF2 pathway exist among the targets predicted by the TargetScan program (http://www.targetscan.org) using the IPA (Ingenuity Systems Pathway Analysis, Redwood City, Calif.) (http://www.ingenuity.com). By this in silico analysis, we unexpectedly found that all four candidate miRNAs might functionally target NRF2 itself, because the seed sequences for three miRNAs, except hsa-miR-450a, were mapped within the 3'UTR of NRF2 (2 sites for hsa-miR-507, 1 site for hsa-miR-634, and 2 sites for hsa-miR-129-5p) (FIG. 3 (b)). FIG. 3 (b) shows homologous sequences of the seed sequences for four candidate miRNAs within the NRF2 3'UTR, and the design for reporter plasmids. The seed sequences for hsa-miR-507 (2 sites), hsa-miR-634 (1 site), and hsa-miR-129-5p (2 sites) were mapped within the 3'UTR of NRF2. Because the seed sequence for hsa-miR-450a is highly homologous to that for hsa-miR-507 (6 of 7 seed sequences), the sites for the seed sequence for hsa-miR-450a are indicated at the same sites as hsa-miR-507. Region 1 (R1), region 2 (R2), or the mutated R2 were used in the luciferase assay. Black symbol "x" shows a mutation site inserted for each seed sequence.

The seed sequence for hsa-miR-450a was highly homologous to that for hsa-miR-507 (6 of 7 seed sequences). Indeed, it was shown that the level of NRF2 protein was remarkably decreased in cells transfected with each miRNA, compared with control-miRNA-transfected cells (FIG. 3 (a)). FIG. 3 (a) shows the results of Western blotting analysis of NRF2 expression in miRNA-transfected cells. Hela cells were transfected with hsa-miR-507, -634, -450a, or -129-5p, or control miRNA. After 48 hours of transfection, Western blotting was performed using cell lysates, followed by immunoreaction with the indicated antibodies.

As shown in FIG. 4, the down-regulation of NRF2 by overexpression of the miRNAs shown in FIG. 3 (a) was also observed in NRF2-stabilized cancer cell lines, LK2 (NSCLC) having a NRF2 mutation, A549 (NSCLC) having a KEAP1 mutation, and JHH-5 (HCC) having p62 protein aggregation. FIG. 4 shows the results of Western blotting analysis regarding NRF2 expression in miRNA-transfected cells. Specifically, hsa-miR-507, -634, -450a, or -129-5p, or control miRNA was transfected into LK2 cells (lung squamous cell carcinoma cells), A549 cells (pulmonary adenocarcinoma cells), and JHH-5 cells (hepatocellular carcinoma cells). After 48 hours of transfection, cell lysates were subjected to SDS-PAGE, followed by immunoreaction with the indicated antibodies.

Therefore, to examine whether each miRNA could directly bind to the 3'-UTR of NRF2, luciferase assays were performed using reporter plasmid vectors having each of two fragments of the 3'-UTR, Region-1 (R1) and Region-2 (R2), or five different mutants of R2 (FIG. 3 (b)).

FIG. 3 (c) shows the results of luciferase assays using reporter plasmids having regions shown in FIG. 3 (b). HeLa cells were co-transfected with a reporter plasmid and an internal control vector, and after 24 hours, hsa-miR-507, -634, -450a, or -129-5p, or control miRNA was transfected. After 48 hours of transfection with miRNAs, firefly or renilla luciferase activity was measured. The luciferase activity relative to that in control-miRNA transfected cells is indicated on the vertical axis. The horizontal line segments below the graphs indicate relevant mutant plasmids in the miRNA-transfected cells. Bars indicate standard deviation (SD). As shown in FIG. 3 (c), the luciferase activity for the R2 vector was significantly reduced compared with that for the empty and R1 vectors in cells transfected with each miRNA, and completely restored with vectors having mutations within seed sequences of R2.

FIG. 3 (d) shows the results of investigation on the effect of transfection of miRNAs on cell survival under cellular stress caused by cisplatin (CDDP) (left) or oxidative stress (hydrogen peroxide) (right). Hela cells were transfected with hsa-miR-507, -634, -450a, or -129-5p, or control miRNA, and the next day, treated with cisplatin (15 µM) for 24 hours, or with hydrogen peroxide (100 µM) for 12 hours. The cell lysate was subjected to SDS-PAGE, and immunoreacted with the indicated antibodies. NRF2 expression was examined by Western blotting (upper panel). Untreated cells for control-miRNA- or miRNA-transfected cells were assessed through the crystal violet staining assay (lower panel). Bars indicate standard deviation (SD). From FIG. 3 (d), it is understood that transfection of each miRNA not only inhibited the expression of NRF2 protein but also significantly increased sensitivity to treatment with cisplatin or exposure to hydrogen peroxide.

The above-described results from Example 2 suggest that all four candidate miRNAs can functionally target NRF2 by directly binding to its 3'-UTR, leading to inhibition of NRF2-mediated cancer cell survival despite elevated cellular stress.

[Example 3] Clinical Significance of the Down-Regulation of the Four miRNAs to Primary Esophageal Squamous Cell Carcinoma (ESCC)

We examined the level of each miRNA by qRT-PCR analysis in 30 samples from patients with primary esophageal squamous cell carcinoma. FIG. 5 shows association between clinical significance and down-regulation of miRNA in primary tumor samples from esophageal carcinoma (esophageal squamous cell carcinoma (ESCC)).

FIG. 5-1 (a) summarizes the results of the expression analysis of four miRNAs (hsa-miR-507, -634, -450a, and -129-5p) and the mutation analysis of the NRF2 or KEAP1 gene in 30 primary tumor samples. Filled squares indicate the presence of a mutation in the NRF2 or KEAP1 gene, or the down-regulation of miRNA in each case. The number of aberrations in each case was shown as the aberrant score (0 to 4), and 30 cases were assigned into two groups based on the "aberration score"; a high score group (n=14; the aberration score ranges from 2 to 4) and a low score group (n=16; the aberration score is 0 or 1). FIG. 5 (b) shows Kaplan-Meier curves for overall survival rates of the 30 ESCC patients according to the aberrant score. The high score group was found to be significantly associated with a worse survival rate (p=0.004, log-rank test). FIG. 5 (c) shows representative images from immunostaining of the NRF2 protein in primary ESCC from the high score group (Case-1, Case-4, and Case-7) (upper panel) and the low score group (Case-21, Case-25, and Case-26) (lower panel). The black solid bars are scale bars, each indicating 100 µm.

FIG. 5-2 shows the results from mutation analysis of NRF2 and KEAP1 genes in esophageal carcinoma (esophageal squamous cell carcinoma: ESCC)-originating primary tumor samples. Among the tumor samples, 5 samples showed amino acid substitution mutations in NRF2 or KEAP1, and those mutations are shown in sequence chromatography profiles. The top three samples showed mutations in the NRF2 gene ("a"), whereas the bottom two samples showed mutations in the KEAP1 gene ("b"). The arrows at the top show wild-type sequences in the corresponding normal tissue, and those at the bottom show mutation sequence and changes in amino acid sequence in primary tumor tissue samples. Also, the term shown at the very bottom, for example, "D77G" means a mutation in which the 77th D (aspartic acid) coded by NRF2 gene in the wild-type amino acid sequence is substituted by G (glycine) (similar rules apply to other terms). Examples of one-letter codes for other amino acids are "R: arginine", "Q: glutamine", "L: leucine", and "M: methionine". Although DNA nucleotide sequences of the NRF2 and KEAP1 genes are known, these are shown as SEQ ID NO: 17 (NRF2: NCBI Reference Sequence: NM_006164.4) and SEQ ID NO: 18 (KEAP1: NCBI Reference Sequence: NM_012289.3).

In the above analyses, a 50% or more reduction in miRNA level in primary tumor tissue, as compared with corresponding non-cancerous tissue, was observed in nine cases (30.0%) for hsa-miR-507, 12 cases (40.0%) for hsa-miR-634, 2 cases (6.7%) for hsa-miR-450a, and 18 cases (60.0%) for hsa-miR-129-5p (FIG. 5-1 (a)). In addition, through mutation analysis, there were found a missense mutation of NRF2 in 3 cases (10%) and that of KEAP1 in 2 cases (6.7%) (FIGS. 5-1 (a) and 5-2). On the basis of an "aberration score" which is an index indicating the number corresponding to cases of decrease in the above four miR levels and missense mutation in the two genes, we studied NRF2 or KEAP1 and/or down-regulation of each miRNA, and assigned 30 cases into two groups; 14 primary ESCC cases with an aberration score of 2 to 4 to a "high score group", and 16 primary ESCC cases with an aberration score of 0 or 1 to a "low score group" (FIG. 5-1 (a)). Importantly, the "high score group" was significantly correlated to distant metastasis (pM categories, p=0.0394, Table 5), and associated with a worse survival rate as shown by the Kaplan-Meier survival estimates (log rank test: p=0.00[4]) (FIG. 5-1 (b)).

TABLE 5

| | | Aberration score | | |
| --- | --- | --- | --- | --- |
| | n | Low score group 0 or 1 | High score group 2, 3 or 4 | P-value[a] |
| Total | 30 | 16 | 14 | |
| Sex | | | | P = 0.4850 |
| Male | 28 | 14 | 14 | |
| Female | 2 | 2 | 0 | |
| Age (years) | | | | |
| median | 64.5 | | | P = 0.9804 |
| 65≤ | 16 | 9 | 7 | |
| 65> | 14 | 7 | 7 | |
| Histopathological grade | | | | P = 0.5229 |
| Well/Moderately | 21 | 12 | 9 | |
| Poorly | 9 | 4 | 5 | |
| pT | | | | P = 0.9197 |
| pT1 | 1 | 1 | 0 | |
| pT2/3 | 23 | 11 | 12 | |
| pT4 | 6 | 4 | 2 | |
| pN | | | | P = 0.8175 |
| pN0 | 7 | 4 | 3 | |
| pN1 | 23 | 12 | 11 | |
| pM category | | | | P = 0.0394 |
| pM0 | 22 | 14 | 8 | |

TABLE 5-continued

| | | Aberration score | | |
|---|---|---|---|---|
| | n | Low score group 0 or 1 | High score group 2, 3 or 4 | P-value[a] |
| pM1a/1b | 8 | 2 | 6 | |
| p stage | | | | P = 0.3940 |
| I/IIA/IIB | 8 | 4 | 2 | |
| III | 18 | 10 | 6 | |
| IVA/IVB | 8 | 2 | 6 | |

* In Table 5, bold letters indicate "statistical significance." The chi square test or Fisher's exact test was used to analyze the data, and a P value of <0.05 in two-tailed test was considered statistically significant.

Immunohistochemical analysis of primary ESCC samples, which were selected randomly, showed that levels of NRF2 protein were markedly higher in the "high score group" than "low score group" (FIG. 5-1 (c)). These findings suggest that the down-regulation of expression for these miRNAs in addition to the mutation of NRF2 or KEAP1 contributes to the NRF2 stabilization in primary ESCC tumors. Furthermore, by use of increase in the "aberration score" as an index, NRF2-stablized tumors may be clarified, and malignancy of the tumors or prognosis of cancer patients may be differentiated.

The 30 samples were subjected to gene amplification by PCR using their extracted DNAs as templates and primers shown in Table 3. The sequences of the PCR products were determined through Sanger's method. FIG. 5-2 shows charts of sequence chromatography results. As shown in FIG. 5-2, regarding NRF2 gene, in a total of three cases, gene mutations of the gain-of-function type with amino acid substitutions were detected (D77G; 1 case, D29G; 2 cases). Also, regarding KEAP1, in a total of two cases, gene mutations with known amino acid substitutions were detected, wherein one was a known gene mutation of the loss-of-function type (R320Q), and in case 4 with an aberration score of 3, a novel gene mutation (L276M) was detected.

[Example 4] In Vivo Tumor-Suppressive Effects by Administration of Hsa-miR-507

Since one miRNA can target multiple genes contributing to one oncogenic pathway, the miRNA may be effective against tumors with this oncogenic pathway. We focused on hsa-miR-507 among the four identified miRNAs and, using expression array and pathway analyses, examined whether it can functionally target genes regulated transcriptionally by NRF2. In these analyses, we found eight transcriptional target genes of NRF2 to be repressed by transfection of hsa-miR-507, and among them, we confirmed that ME1 is a direct target for hsa-miR-507 through binding to the 3'-UTR of NRF2 (FIG. 6). FIG. 6 shows the results of identification of transcriptional target genes of NRF2 serving as the target of hsa-miR-507. FIG. 6 (a) shows the results of validation of transcriptional target genes of NRF2 negatively regulated by hsa-miR-507. It shows that among the genes whose expression is down-regulated through transfection of hsa-miR-507 or NRF2-siRNA, 181 genes have been predicted as targets of hsa-miR-507 by the program TargetScan. FIG. 6 (b) shows that through use of IPA, among 181 genes, eight transcriptional targets of NRF2 (ME1, PSMB6, SLC7A11, MGLL, DNAJB5, LGALS8, B4GALNT1, EIF4G2) have been predicted as the targets of hsa-miR-507. FIG. 6 (c) shows the mapping of the seed sequences for hsa-miR-507 in the ME1 3'-UTR and the design for reporter plasmids. It shows the results of examination as to whether hsa-miR-507 can directly bind to ME1 3'-UTR by using a luciferase analysis. The seed sequence for hsa-miR-507 is mapped within the ME1 3'UTR. In luciferase assay, we used reporter plasmids having the genomic region of a seed sequence for hsa-miR-507 (wild type; WT) or its mutant. Black crosses indicate mutation sites. FIG. 6 (d) shows the results of the luciferase assay using the reporter plasmids. HeLa cells were cotransfected with a reporter plasmid and an internal control vector, and after 24 hours, hsa-miR-507 or control miRNA was transfected. After 48 hours of transfection with miRNA, firefly or renilla luciferase activity was measured. The luciferase activity relative to that in control-miRNA-transfected cells is indicated on the vertical axis. The luciferase activity for the vector having the WT region was weaker than that for the empty vector, but was completely restored by inserting a mutation within the seed sequence. Bars indicate standard deviation (SD). FIG. 6 (e) shows the results of Western blotting analysis of ME1 expression in miRNA-transfected cells. Hela cells were transfected with hsa-miR-507 or control miRNA. After 48 hours of transfection, the cell lysate was subjected to SDS-PAGE, followed by immunoreaction with the indicated antibodies, to thereby confirm that transfection with hsa-miR-507 actually reduces the expression level for ME1 protein.

These results in FIG. 6 suggest that hsa-miR-507 can inhibit the NRF2-mediated oncogenic pathway by directly targeting both NRF2 and its target gene(s)

Next, we examined the tumor-suppressive effect in vivo of the administration of double-stranded RNA mimicking hsa-miR-507 or control miRNA into subcutaneous spaces surrounding tumors formed by A549 cells. FIG. 7 shows expression analysis of 4 miRNAs, and the effect of transfection with hsa-miR-507 on survival of A549 cells under cellular stress induced by cisplatin (CDDP) treatment in A549 cells.

Furthermore, we examined the tumor-suppressive effect in vivo of the administration of double-stranded RNA mimicking hsa-miR-507 or control miRNA into subcutaneous spaces surrounding tumors formed by A549 cells. Combined treatment with carboplatin and NRF2-specific siRNA was reported, by Singh, et al., to be effective in inhibiting the growth of tumors formed from A549 cells, and this cell line was assigned to the "high score group" with the KEAP1 mutation and the down-regulation of three miRNAs; i.e., hsa-miR-507, hsa-miR-634, and hsa-miR-129-5p, except for hsa-miR450a (FIG. 7 (a)). FIG. 7 (a) shows the results of expression analysis, by qRT-PCR, of the four miRNAs; i.e., hsa-miR-507, -634, -450a, and -129-5p. The expression level of RNU6B was used as the internal control. The expression level in A549 cells relative to that in normal lung tissue is indicated on the vertical axis. Bars indicate standard deviation (SD).

Furthermore, we showed that the exogenous overexpression of hsa-miR-507 mildly inhibited cell growth and increased sensitivity to cellular stress caused by cisplatin in vivo (FIGS. 7 (b) and 7 (c)). FIG. 7 (b) shows the results of cell growth analysis in hsa-miR-507-transfected A549 cells. A549 cells were transfected with hsa-miR-507 or control miRNA, and on the days indicated, the number of living cells was measured through CV staining assay. The vertical axis shows relative cell growth rate. Bars indicate standard deviation (SD). Significant differences were analyzed by Student's t-test. The results were as follows: *p=0.0172 (day 2), p=0.0293 (day 4), and p=0.0067 (day 6). FIG. 7 (c) shows the effect of transfection with hsa-miR-507 on survival of A549 cells under cellular stress caused by cisplatin (CDDP) in the cells. Specifically, A549 cells were transfected with hsa-miR-507 or control miRNA and, on the following day, treated with PBS or cisplatin (2 μM) for 48 hours. The cell survival rate relative to that in untreated cells for the control-miRNA- or miRNA-transfected cells was assessed by CV staining. Bars indicate standard deviation (SD). Significant differences were analyzed by two-way ANOVA (two-factor analysis of variance). The results were as follows: *p=0.0002 (between control miRNA and hsa-miR-507), p=0.1844 (between PBS and CDDP). The interaction (hsa-miR-507×CDDP) was p=0.0049. $F_{miR-07}=43.2006$, $F_{CDDP}=11.2564$, $F_{miR-507 \times CDDP}=14.7665$.

FIG. 8 shows the in vivo tumor-suppressive effect of hsa-miR-507. FIG. 8 (a) shows the experimental schedule for the combined treatment with hsa-miR-507 and cisplatin (CDDP). Tumors were formed by subcutaneous injection of A549 cells in nude mice. Control miRNA or hsa-miR-507 was administered around tumors that were formed from A549 cells under the skin a total of four times (7, 14, 21 and 28 days after the injection of A549 cells). In addition, the mice were treated with PBS or cisplatin by intraperitoneal administration the next day a total of three times (8, 15 and 22 days after the injection of A549 cells). 35 days after the injection of A549 cells, the mice were euthanized and the tumors were resected. Tumor weight was significantly reduced by the supplemental use of PBS and cisplatin in combination with hsa-miR-507 (FIGS. 8 (b) and 8 (c)). FIG. 8 (b) shows representative images of tumor-bearing mice (left) and the resected tumors (right) 35 days after the injection of A549 cells. In the image of the left-side mouse, the outline letters "miR-507" (two occurrences) both indicate "hsa-miR-507". FIG. 8 (c) shows the weight of the resected tumors. Mice were euthanized 35 days after the injection of A549 cells, and the weight of each resected tumor sample was measured. The graph indicates "average±SD" in 4 PBS-treated mice or 3 cisplatin-treated mice. Significant differences were analyzed by two-way ANOVA (two-factor analysis of variance). p=0.0486 between the control miRNA group and the hsa-miR-507 group. p=0.5716 between the PBS group and the cisplatin group. The interaction (hsa-miR507×CDDP) was p=0.8757. $F_{miR-507}=170.667$, $F_{CDDP}=1304444$, and $F_{miR-507 \times CDDP}=0.026601$.

In addition, the enhanced expression of hsa-miR-507 together with the down-regulated expression of NRF2 and ME1 protein was confirmed in hsa-miR-507-treated tumors (FIGS. 8 (d) and 8 (e)). FIG. 8 (d) shows expression analysis of hsa-miR-507 in the resected tumors. The mRNA expression level of hsa-miR-507 was measured by qRT-PCR. The expression of RNU6B was used as the internal control. The expression level relative to that in the control-miRNA-administered mouse tumor in PBS-treated mice is indicated on the vertical axis. Bars indicate standard deviation (SD). FIG. 8 (e) shows representative images obtained from immunostaining of NRF2 and ME1 in the resected tumor samples. Each scale bar represents 100 μm.

Thus, these results suggest that hsa-miR-507 can inhibit tumor growth by targeting the NRF2-mediated oncogenic pathway. The above-described findings show utility of miRNA-based molecular diagnosis and its therapeutic efficacy in NRF2-stabilized tumors.

Also, our findings reveal that combined administration of hsa-miR-507 and cisplatin provides synergistic anti-cancer effect. Thus, the present invention provides a cancer therapeutic agent which is a combination of a cancer therapeutic agent consisting of a nucleic acid including the nucleotide sequence of hsa-miR-507 (SEQ ID NO: 1), and a platinum agent such as cisplatin. No particular limitation is imposed on the mode of combination of a cancer therapeutic agent consisting of a nucleic acid including the nucleotide sequence of hsa-miR-507 (SEQ ID NO: 1) and a platinum agent such as cisplatin. That is, both may be contained in a single composition, or the two may be individually and separately administered. As described hereinabove, one of the two may be administered before the other, and vice versa. Alternatively, the two agents may be administered at the same time. Modes of administration of the cancer therapeutic agent consisting of a nucleic acid including the nucleotide sequence of hsa-miR-507 (SEQ ID NO: 1) are already described herein above. For administration of cisplatin, for example, known modes may be employed. Specifically, cisplatin is administered to an adult at a dose of 70 to 80 $mg/m^2$ (body surface area) per day, for an administration period of 2 to 5 months, during which administration is performed once a day or so under a preset regimen of administration frequency (roughly between once a week and every 4 weeks) generally through drip infusion.

[Example 5] Anti-Tumor Effect Obtained by the Administration of hsa-miR-634

(1) In Vitro Apoptosis Inducing Effect on Tumors Through Administration of Hsa-miR-634 (1) (FIG. 9)

FIG. 9 shows the results of our in vitro study on the apoptosis inducing effect of hsa-miR-634 on tumor cells. In order to examine in vitro tumor-suppressive effect of hsa-miR-634, hsa-miR-634-mimicking double-stranded RNA or control miRNA was transfected into Hela cells, a cervical carcinoma cell line, through the lipofection method, followed by incubation for 3 days. After 1, 2, and 3 days of transfection, the cells were subjected to staining with PBS solution containing 1% crystal violet for 1 minute, washed with water, and then allowed to react in a PBS buffer containing 2% SDS for 1 hour. Subsequently, staining intensity was measured using a multiplate reader, to quantify the living cells. As a result, in cells in which hsa-miR-634 was expressed, significant cell growth inhibition and apoptosis induction were confirmed. FIG. 9 (A) shows microscopic images taken 2 days after transfection. Briefly, HeLa cells were transfected with hsa-miR-634, and then incubated in an atmosphere of 5% $CO_2$ at 37° C. for 48 hours. Morphological changes of the cells after incubation are seen in the micrographs. The upper images are from control-miR-transfected cells, and the lower ones are from hsa-miR-634-transfected cells. The images on the right side are enlarged ones of the left images. FIG. 9 (B) shows the results of cell-growth-inhibitory effect over time. Specifically, FIG. 9 (B) shows cell growth confirmed, after 1, 2, and 3 days under incubation described in relation to FIG. 9 (A), by the use of fluorescence intensity by CV staining as an index. The results are from cells of mock-transfected cells, control-miR-transfected cells, and miR-634-transfected cells.

After 2 days of transfection, cells were centrifugally recovered, and the pelletized cells were fixed with 70% ethanol-containing PBS at 4° C. for 30 minutes, followed by RNase treatment. The resultant cells were stained with PI solution (1 μg/ml). FACS analysis was performed using a flow cytometer (FIG. 9 (C)). The left chart shows the distribution of control-miR-transfected cells, and the right chart shows that of hsa-miR-634-transfected cells. These charts reveal that in hsa-miR-634-transfected cells, cells in the SubG1 phase (peak G1) indicating apoptosis markedly increased.

The above demonstrates that transfection of hsa-miR-634 into tumor cells can induce apoptosis-mediated cell death, proving a clear tumor inhibitory effect. This result substantiates prominent cancer therapeutic effect of the cancer therapeutic agent of the present invention.

(2) In Vitro Apoptosis Inducing Effect on Tumors Through Administration of Hsa-miR-634 and Cisplatin (2) (FIG. 10)

Cells of esophageal carcinoma cell line KYSE170 were transfected with hsa-miR-634-mimicking double-stranded RNA or control miRNA through the lipofection method. At the top of FIG. 10 is shown the in vitro assay schedule for the combined administration of hsa-miR-634 and cisplatin (CDDP). As shown in the schedule, the additive amount of hsa-miR-634-mimicking double-stranded RNA or control miRNA was 0.2 nM. 2.5 μM cisplatin adding groups and 5.0 μM cisplatin adding groups were subjected to incubation for 72 hours. The apoptosis inducing effect was assessed by the occurrence (%) of apoptosis relative to the number of all cells, wherein the dead cells were counted by trypan blue staining. The graph at the bottom of FIG. 10 shows the results. The vertical axis shows the above-mentioned occurrence of cell death. Notably, in cells to which hsa-miR-634 and cisplatin were administered simultaneously, apoptosis was induced at high incidence. Thus, synergistic anti-cancer effect can be obtained from co-administration of the therapeutic agent according to the present invention and cisplatin.

(3) In Vivo Apoptosis Inducing Effect on Tumors Through Administration of Hsa-miR-634 and Cisplatin (FIG. 11)

In vivo study was performed to assess co-administration of hsa-miR-634 and cisplatin using tumor-bearing nude mice, wherein tumors were formed by subcutaneous injection of KYSE170 cells. At the top of FIG. 11 is shown the in vivo test schedule for the combined treatment with hsa-miR-634-mimicking double-stranded RNA or control miRNA, and cisplatin (CDDP). The incubation period for forming tumors was 7 days. On day 7 of incubation, control miRNA or hsa-miR-634 was administered by injection around tumors subcutaneously formed from KYSE170 cells a total of five times. Each mouse was intraperitoneally administered PBS or cisplatin at the first and fourth administrations of miRNA, simultaneously with the miRNA administration (i.e., twice in total). After 21 days of KYSE170-cell injection, the mice were euthanized and tumors were resected. The graph at the bottom of FIG. 11 shows the weight of the resected tumors (vertical axis). The graph shows "average±SD" of the weight of tumors in 7 PBS-treated mice, and 8 cisplatin-treated mice. A t-test analysis reveals significant difference between the following two groups: p=0.0182 between the control miRNA group and the hsa-miR-634 administration group in cisplatin-treated mice, and p=0.00813 between PBS and cisplatin in hsa-miR-634-administered mice.

(4) Expression Inhibitory Effect of Hsa-miR-634 on a Target Gene in Osteosarcoma Cells FIG. 12 (FIGS. 12-1 to 12-4) shows expression inhibitory effect of hsa-miR-634 transfection on a target gene in osteosarcoma U2OS cells. The luciferase assay results shown on the left graphs in FIGS. 12-1 to 12-4 were obtained from the aforementioned "conventional luciferase assay" procedures. That is, luciferase reporter plasmids to be used in various assays were made by inserting the 3'-UTR of each target gene downstream of the luciferase gene within the pmirGLO Dual-Luciferase miRNA Target Expression Vector (Promega). The target genes are (a) XIAP (X-linked inhibitor of apoptosis protein: FIG. 12-1), (b) APIP (APAF1 interacting protein: FIG. 12-2), (c) OPA1(optic atrophy 1: FIG. 12-3), and (d) TFAM (transcription factor A, mitochondrial: FIG. 12-4). The UTR seed sequences of genes encoding these four proteins are shown by SEQ ID NO: 52 (XIAP), 53 (APIP), 54 (OPA1) and 55 (TFAM) in the sequence listing. All the site-specific mutations were detected using a KOD mutagenesis kit (TOYOBO). In the graphs, "mt" indicates mutation-introduced plasmid (mutant: mt).

Luciferase reporter plasmids, or mutation-introduced plasmids (mt), and pTK plasmids as the internal control were co-transfected in U2OS cells, and on the following day, the hsa-miR-634-mimicking double-stranded RNA or control miRNA was transfected. After 2 days, firefly and *renilla* luciferase activities were measured using Dual-Luciferase Reporter Assay System (Promega), and relative luciferase activity was calculated by normalizing the firefly luciferase reading with its corresponding internal *renilla* luciferase control.

The results of the above luciferase assay suggests that, through direct binding of hsa-miR-634 to the 3'UTR seed sequence of each of the above-mentioned target genes in tumor cells, hsa-miR-634 can inhibit expression of the genes. Also, it has been clarified that since enhanced expression of the target genes aggravates the malignancy of cancer cells, use of the expression of those genes as an index for performing the method of the present invention can further enhance the reliability of the measurement assay.

On the right side of each of FIGS. 12-1 to 12-4, electrophoresis results are shown. For western blotting, osteosarcoma U2OS cells were transfected with 2 nM or 20 nM hsa-miR-634-mimicking double-stranded RNA or control miRNA through the lipofection method. Each of lysates of the thus-prepared whole cells was subjected to SDS-PAGE, and proteins were transferred to PVDF membranes (GE Healthcare). After blocking with TBS containing 0.05% Tween 20 and 5% non-fat dry milk for 1 hour, each membrane was reacted with an antibody overnight. Dilution factors for primary antibodies were as follows: rabbit anti-XIAP (1/1,000), rabbit anti-APIP (1/1,000), rabbit anti-OPA1 (1/1,000), rabbit anti-TFAM (1/1,000), and mouse anti-β-actin (1/5,000). The membrane was washed and exposed to HRP-conjugated anti-mouse or rabbit IgG antibodies (both at 1/2,000) for 2 hours. The bound antibodies were visualized with HRP staining solution or with an ECL Western blotting kit (Cell Signaling Technology) according to the manufacturer's instructions.

The Western blotting results show that when tumor cells are transfected with hsa-miR-634, protein expression level of each target gene decreases.

Thus, the results from the luciferase assay and Western blotting described herein show excellent effect of hsa-miR-634 as a cancer therapeutic agent, and in particular, show hsa-miR-634 is useful not only against cancer cells in which gene expression of NRF2 is elevated or stabilized, but also against such cells in which gene expression of XIAP, APIP, OPA1 or TFAM is elevated or stabilized.

Moreover, our findings reveal that combined administration of hsa-miR-634 and cisplatin provides synergistic anti-cancer effect. Thus, the present invention provides a cancer therapeutic agent which is a combination of a cancer therapeutic agent consisting of a nucleic acid including the nucleotide sequence of hsa-miR-634 (SEQ ID NO: 2), and a platinum agent such as cisplatin. No particular limitation is imposed on the mode of combination of a cancer therapeutic agent consisting of a nucleic acid including the nucleotide sequence of hsa-miR-634 (SEQ ID NO: 2) and a platinum agent such as cisplatin. That is, both may be contained in a single composition, or the two may be individually and separately administered. As described hereinabove, one of the two may be administered before the other, and vice versa. Alternatively, the two agents may be administered at the same time. Modes of administration of the cancer therapeutic agent consisting of a nucleic acid including the nucleotide sequence of hsa-miR-634 (SEQ ID NO: 2) are already described herein above. For administration of cisplatin, for example, known modes may be employed. Modes of administration are already described herein above. For administration of cisplatin, for example, known modes may be employed. Specifically, cisplatin is administered to an adult at a dose of 70 to 80 mg/m$^2$ (body surface area) per day, for an administration period of 2 to 5 months, during which administration is performed once a day or so under a preset regimen of administration frequency (roughly between once a week and every 4 weeks) generally through drip infusion.

INDUSTRIAL APPLICABILITY

As described above, the present inventors have found that miRNAs that directly target the NRF2 gene can repress the NRF2-mediated oncogenic pathway, leading to the completion of the invention. NRF2 is constitutively stabilized in various types of human cancers by survival mechanisms including gain-of-function mutations of NRF2, loss-of-function mutations of KEAP1, and the functional deactivation of KEAP1 caused by the accumulation of p62 protein. Also the present inventors have shown that specific miRNAs are aberrantly down-regulated in cancer cases. Importantly, the aberrant down-regulation of one or more miRNAs which is coincident with the mutation of NRF2 or KEAP1 and in addition p62 protein accumulation is closely associated with NRF2 stabilization in tumors and the poor prognosis of cancer patients.

Furthermore, the present inventors studied the expression status of specific miRNAs that directly target NRF2, and have elucidated that the down-regulation of these miRNAs helps to increase the basal activity level of NRF2, and synergistically stabilizes the NRF2 protein with or without genetic aberrations of NRF2 or KEAP1 and p62 protein accumulation in tumors.

Based on the above findings, the present inventors provide the present assay method which can differentiate malignancy of tumors and prognosis of cancer patients.

Protein accumulation of NRF2, KEAP1, or p62, and elevation or stabilization of expression of gene XIAP, APIP, OPA1, or TFAM are useful as an index for screening NRF2-stabilized tumors. Also, the inhibition itself of NRF2 activity in tumors is a rational approach in the treatment of NRF2-stabilized tumors.

Previous studies have demonstrated that one miRNA can inhibit the expression of multiple targets by directly binding to the 3'-UTR of each gene (Non-Patent document 25). This suggests that one miRNA concurrently targets several genes related to one signaling pathway. Actually, miR-16 was reported to negatively regulate the cell cycle by directly targeting CDK1 and CDK2 (Non-Patent document 26).

Furthermore, miR-34a is known to act as a negative regulator of tumor development and metastasis by directly targeting multiple genes, CCND1, CDK4, CDK6, and MYC (Non-Patent Document 27). The present inventors have shown that administration of hsa-miR-507 is actually effective for inhibiting development of tumors formed from A549 cells in nude mice, by targeting NRF2 as well as ME1, a transcriptional target of NRF2. In vivo analysis performed by the present inventors revealed that the transfection of hsa-miR-507 led to an increase in the sensitivity of cell-growth suppression with a platinum agent such as cisplatin in A549 cells. In addition to acquisition of resistance against cellular stress from chemotherapy, NRF2 also promotes tumor cell growth by modulating metabolism. In this connection, the present inventors showed that tumor growth is inhibited by hsa-miR-507 both in vitro and in vivo. The growth inhibition by hsa-miR-507 may be attributed to changes in intracellular metabolism through repression of NRF2 and its target genes.

Furthermore, the present inventors have shown tumor suppressive effect of hsa-miR-634 both in vitro and in vivo. The tumor suppressive effect is obtained when tumor cells are forced to undergo apoptosis. Also, by use of hsa-miR-634 and a platinum agent, such as cisplatin, in combination, this effect can be markedly enhanced. This finding surely substantiates the usefulness of the cancer therapeutic agent of the present invention.

As described above, the present invention provides a miRNA-based molecular diagnosis and new means for the treatment of tumors in which NRF2, etc. is stabilized.

The invention claimed is:

1. A method for treating a cancer, wherein said method comprises administering, to a subject with a cancer, a therapeutically-effective amount of an miRNA molecule comprising hsa-miR-634,
and wherein cancer cells of said cancer exhibit elevated or stabilized expression of at least one of NRF2 (NF-E2-related factor 2), XIAP (X-linked inhibitor of apoptosis protein), APIP (APAF1 interacting protein), OPA1 (optic atrophy 1) or TFAM (transcription factor A, mitochondrial), as compared to a corresponding non-cancerous cell.

2. The method of claim 1, wherein said miRNA molecule comprises the nucleotide sequence of SEQ ID NO: 2.

3. The method of claim 1, wherein said miRNA molecule is a double-stranded RNA, an RNA-DNA complex double strand, an RNA-PNA complex double strand, or an RNA-LNA complex double strand.

4. The method of claim 1, wherein said therapeutically-effective amount is an amount effective to induce apoptosis of cancer cells of said cancer.

5. The method of claim 1, wherein said cancer is selected from the group consisting of esophageal cancer, lung cancer, breast cancer, oral cancer, stomach cancer, colorectal cancer, liver cancer, uterine cancer, osteosarcoma, and skin cancer.

6. The method of claim 1, wherein said cancer is skin cancer.

7. The method of claim 1, wherein said cancer cells contain a D77G or D29G mutation in the NRF2 gene.

8. The method of claim 1, wherein said method further comprises administering, to said subject, an anti-cancer agent.

9. The method of claim 8, wherein said anti-cancer agent is a platinum agent.

10. The method of claim 9, wherein said platinum agent is cisplatin.

11. A method for treating a cancer, wherein said method comprises administering, to a subject with a cancer, a therapeutically-effective amount of an miRNA molecule comprising hsa-miR-634, and
wherein cancer cells of said cancer exhibit an increase in ARE (antioxidant response element) activity as compared to a corresponding non-cancerous cell.

12. The method of claim 11, wherein said miRNA molecule comprises the nucleotide sequence of SEQ ID NO: 2.

13. The method of claim 11, wherein said miRNA molecule is a double-stranded RNA, an RNA-DNA complex double strand, an RNA-PNA complex double strand, or an RNA-LNA complex double strand.

14. The method of claim 11, wherein said miRNA molecule, after uptake by said cancer cells, has an activity of decreasing a relative ratio of the ARE activity to less than 0.5.

15. The method of claim 11, wherein said therapeutically-effective amount is an amount effective to induce apoptosis of cancer cells of said cancer.

16. The method of claim 11, wherein said cancer is selected from the group consisting of esophageal cancer, lung cancer, breast cancer, oral cancer, stomach cancer, colorectal cancer, liver cancer, uterine cancer, osteosarcoma, and skin cancer.

17. The method of claim 11, wherein said cancer is skin cancer.

18. The method of claim 11, wherein said method further comprises administering, to said subject, an anti-cancer agent.

19. The method of claim 18, wherein said anti-cancer agent is a platinum agent.

20. The method of claim 19, wherein said platinum agent is cisplatin.

* * * * *